United States Patent
Babich et al.

(10) Patent No.: US 9,388,144 B2
(45) Date of Patent: Jul. 12, 2016

(54) RADIOLABELED PROSTATE SPECIFIC MEMBRANE ANTIGEN INHIBITORS

(71) Applicant: Molecular Insight Pharmaceuticals, Inc., Tarrytown, NY (US)

(72) Inventors: John W. Babich, Tarrytown, NY (US); Craig Zimmerman, Topsfield, MA (US); John L. Joyal, Melrose, MA (US); Genliang Lu, Winchester, MA (US)

(73) Assignee: Molecular Insight Pharmaceuticals, Inc., Tarrytown, NY (US)

( * ) Notice: Subject to any disclaimer, the term of this patent is extended or adjusted under 35 U.S.C. 154(b) by 43 days.

(21) Appl. No.: 14/553,157

(22) Filed: Nov. 25, 2014

(65) Prior Publication Data

US 2015/0078998 A1 Mar. 19, 2015

Related U.S. Application Data

(62) Division of application No. 13/566,849, filed on Aug. 3, 2012, now Pat. No. 8,926,944.

(60) Provisional application No. 61/515,674, filed on Aug. 5, 2011.

(51) Int. Cl.
| | |
|---|---|
| *A61K 51/04* | (2006.01) |
| *A61K 49/00* | (2006.01) |
| *C07D 257/02* | (2006.01) |
| *C07D 255/02* | (2006.01) |
| *C07F 5/00* | (2006.01) |
| *C07D 403/14* | (2006.01) |

(52) U.S. Cl.
CPC .......... *C07D 257/02* (2013.01); *A61K 49/0002* (2013.01); *A61K 51/0478* (2013.01); *A61K 51/0482* (2013.01); *C07D 255/02* (2013.01); *C07D 403/14* (2013.01); *C07F 5/003* (2013.01)

(58) Field of Classification Search
CPC .......... A61K 9/00; A61K 49/00; A61K 51/04
See application file for complete search history.

(56) References Cited

U.S. PATENT DOCUMENTS

2011/0064657 A1 3/2011 Pomper et al.

FOREIGN PATENT DOCUMENTS

| WO | WO-2009/002529 | * 12/2008 |
| WO | WO 2009/002529 A2 | 12/2008 |
| WO | WO 2010/065902 A2 | 6/2010 |
| WO | WO 2010/108125 A2 | 9/2010 |

OTHER PUBLICATIONS

Greene et al., "Protective Groups in Organic Synthesis," *Third Edition, John Wiley & Sons, Inc.*, pp. xi-xii (1999).
International Search Report issued in International Application No. PCT/US12/49644 dated Oct. 17, 2012.
Non-Final Office Action issued in U.S. Appl. No. 13/566,849 dated Mar. 19, 2014.
Notice of Allowance issued in U.S. Appl. No. 13/566,849 dated Aug. 28, 2014.
Wermuth (editor), "The Practice of Medicinal Chemistry," *Academic Press Limited*, pp. 203-237 (1996).

* cited by examiner

*Primary Examiner* — Michael G Hartley
*Assistant Examiner* — Jagadishwar Samala
(74) *Attorney, Agent, or Firm* — Gilberto M. Villacorta; Jeffrey R. Lomprey; Foley & Lardner LLP

(57) ABSTRACT

Compounds according to Formula I and Formula II are potent inhibitors of PSMA activity:

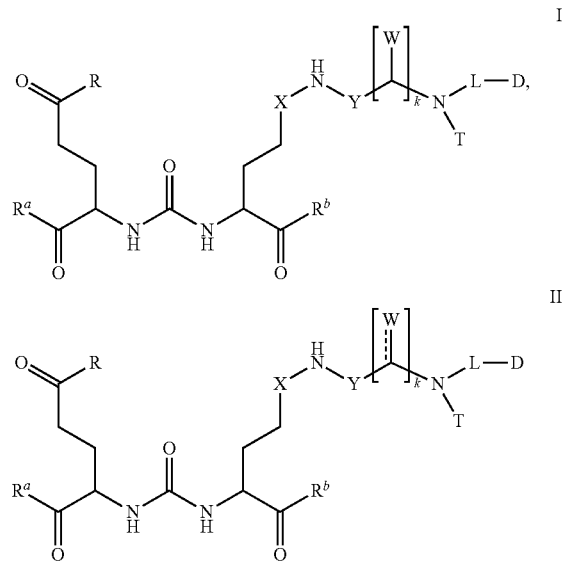

Pharmaceutical compositions may include a complex of a radionuclide and a compound of Formula I or Formula II.

29 Claims, 3 Drawing Sheets

Figure 1A *In Vivo*
Lu-MIP-1519:(11S,16S,20S)-11-(2-carboxyethyl)-10,13,18-trioxo-1-((4-((1,4,7,10-tetrakis(carboxymethyl)-1,4,7,10-tetraazacyclododecan-2-yl)methyl)phenyl)amino)-1-thioxo-2,9,12,17,19-pentaazadocosane-16,20,22-tricarboxylate Lu complex.
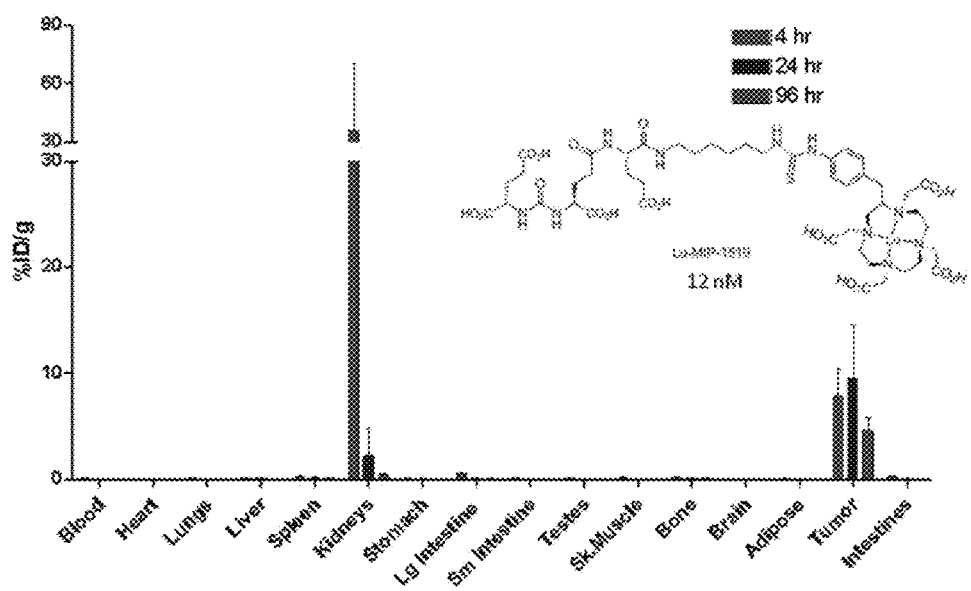

Figure 1B *In Vivo Data*
Lu-MIP-1545: (10S,17S,21S)-10-(naphthalen-2-ylmethyl)-8,11,19-trioxo-1-((4-((1,4,7,10-tetrakis(carboxymethyl)-1,4,7,10-tetraazacyclododecan-2-yl)methyl)phenyl)amino)-1-thioxo-2,9,12,18,20-pentaazatricosane-17,21,23-tricarboxylate Lu complex
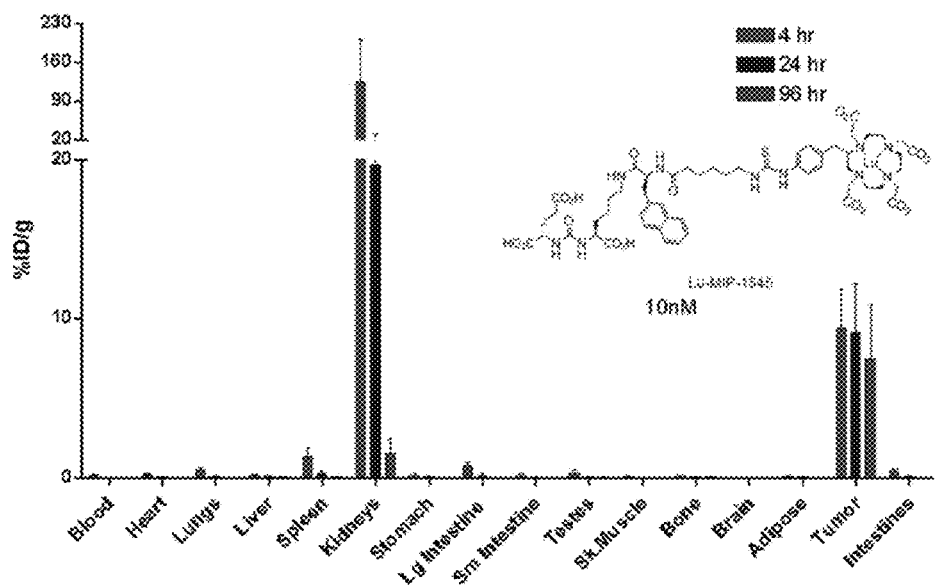

Figure 2. *In-Vivo* Data
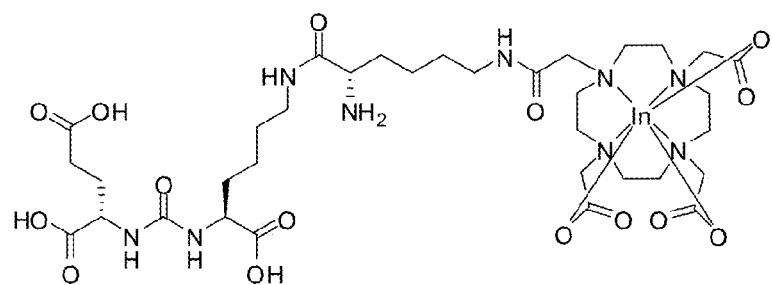
(Compound of Example 3)
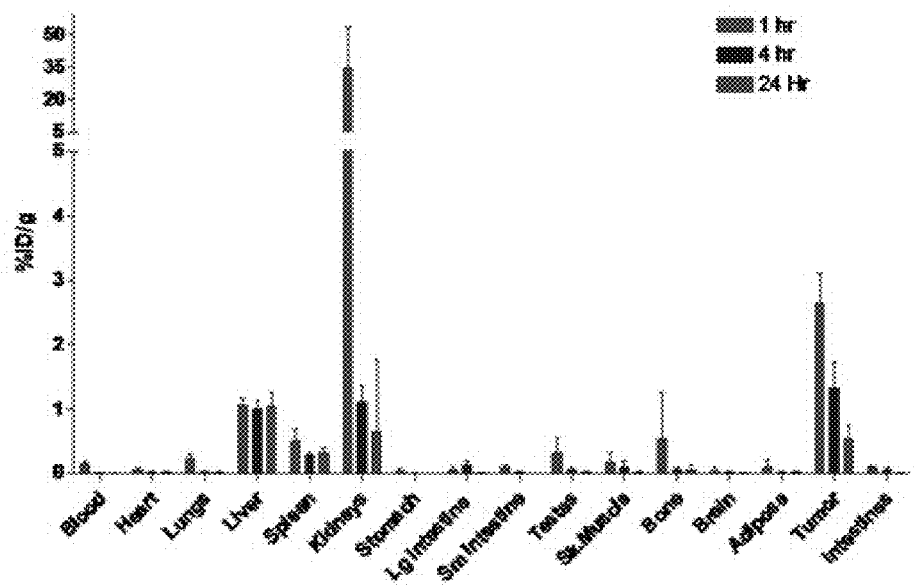

RADIOLABELED PROSTATE SPECIFIC MEMBRANE ANTIGEN INHIBITORS

CROSS-REFERENCE TO RELATED APPLICATIONS

This application is a divisional of U.S. patent application Ser. No. 13/566,849, filed Aug. 3, 2012, which in turn claims the benefit of U.S. Provisional Application Ser. No. 61/515,674, filed Aug. 5, 2011, the entire contents of which are incorporated by reference herein in their entirety.

TECHNICAL FIELD

The present technology generally relates to the field of radiopharmaceuticals and their use in nuclear medicine as tracers, imaging agents and for the treatment of various disease states.

BACKGROUND

It is well known that tumors may express unique proteins associated with their malignant phenotype or may over-express normal constituent proteins in greater number than normal cells. The expression of distinct proteins on the surface of tumor cells offers the opportunity to diagnose and characterize disease by probing the phenotypic identity and biochemical composition and activity of the tumor. Radioactive molecules that selectively bind to specific tumor cell surface proteins provide an attractive route for imaging and treating tumors under non-invasive conditions. In particular, the present inventors have found that radiolabeled ligands to the prostate-specific membrane antigen (PSMA) protein, often over expressed on many cancer cells provide an attractive route for non-invasive imaging and selective targeting of cancer cells.

At least 1 million men suffer from prostate cancer and it's estimated that the disease will strike one in six U.S. men between the ages of 60 and 80. There are more than 300,000 new cases of prostate cancer diagnosed each year. Prostate cancer will affect one in six men in the United States, and the mortality from the disease is second only to lung cancer. An estimated $2 billion is currently spent worldwide on surgical, radiation, drug therapy and minimally invasive treatments, $1 billion of the spending in the U.S. There is presently no effective therapy for relapsing, metastatic, androgen-independent prostate cancer. New agents that will enable rapid visualization of prostate cancer and specific targeting to allow radiotherapy present are needed.

N-acetylated alpha-linked acidic dipeptidase (NAALADase), also known as glutamate carboxypeptidase II (GCPII) is a neuropeptidase which cleaves N-acetylaspartylglutamate (NAAG) into N-acetylaspartate and glutamate in the nervous system, see below, depicting hydrolytic cleavage of NAAG by NAALDase through the tetrahedral intermediate. The enzyme is a type II protein of the co-catalytic class of metallopeptidases, containing two zinc atoms in the active site.

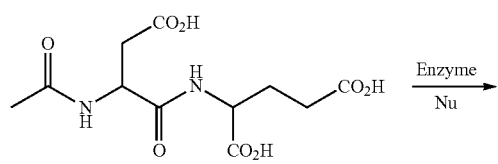

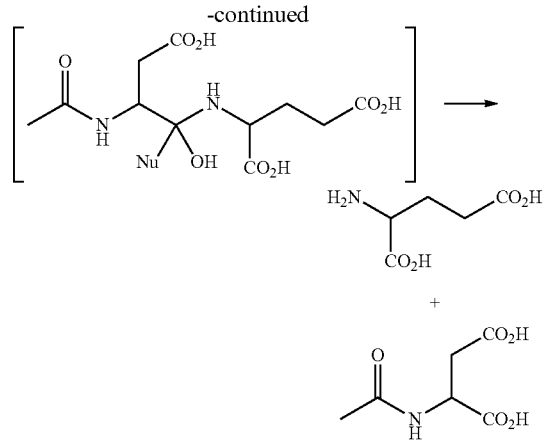

Independent of its characterization in the nervous system, one form of NAALADase was shown to be expressed at high levels in human prostatic adenocarcinomas and was designated the prostate-specific membrane antigen (PSMA). The NAALADase/PSMA gene is known to produce multiple mRNA splice forms and based on previous immunohistochemical evidence, it has been assumed that the human brain and prostate expressed different isoforms of the enzyme.

Human prostate-specific membrane antigen (PSMA), also known as folate hydrolase I (FOLH1), is a trans-membrane, 750 amino acid type II glycoprotein which is primarily expressed in normal human prostate epithelium but is upregulated in prostate cancer, including metastatic disease. PSMA is a unique exopeptidase with reactivity toward poly-gamma-glutamated folates, capable of sequentially removing the poly-gamma-glutamyl termini. Since PSMA is expressed by virtually all prostate cancers and its expression is further increased in poorly differentiated, metastatic and hormone-refractory carcinomas, it is a very attractive target for prostate imaging and therapy. Developing ligands that interact with PSMA and carry appropriate radionuclides may provide a promising and novel targeting option for the detection, treatment and management of prostate cancer.

The radio-immunoconjugate form of the anti-PSMA monoclonal antibody (mAb) 7E11, known as the PROSTASCINT scan, is currently being used to diagnose prostate cancer metastasis and recurrence. More recently, monoclonal antibodies have been developed that bind to the extracellular domain of PSMA and have been radiolabeled and shown to accumulate in PSMA-positive prostate tumor models in animals. However, diagnosis and tumor detection using monoclonal antibodies has been limited by the low permeability of the monoclonal antibody in solid tumor. Tumor detection using low molecular weight radiopharmaceutical compounds, therefore, hold promise and are being explored as potential diagnostic and radiopharmaceutical alternatives to radio-immunoconjugates of monoclonal antibodies.

The selective targeting of cancer cells with radiopharmaceuticals, either for imaging or therapeutic purposes is challenging. A variety of radionuclides are known to be useful for radio-imaging or cancer radiotherapy, including $^{111}$In, $^{90}$Y, $^{68}$Ga, $^{177}$Lu, $^{99m}$Tc, $^{123}$I and $^{131}$I. Recently it has been shown that some compounds containing a glutamate-urea-glutamate (GUG) or a glutamate-urea-lysine (GUL) recognition element linked to a radionuclide-ligand conjugate exhibit high affinity for PSMA. Importantly, the present inventors found that the avidity of the GUL-radionuclide conjugate and GUG-radionuclide conjugate depends at least in part on the nature and size of the linker or spacer joining the GUL or GUG moiety to the radionuclide group. The present invention focuses on exploring the relationship between binding affinity and linker length as well as the relationship between binding affinity and chemical nature of the linker group, as well as on the synthesis, characterization and methods for using the inventive GUL-radionuclide and GUG-radionuclide conjugates for the diagnosis and treatment of diseases.

SUMMARY

In one aspect, compounds are provided that fall within the scope of Formulae I or II, or their metal complexes. In another aspect, methods are provided for using pharmaceutically acceptable compositions of the Formulae I or II compounds and/or metal complexes to obtain radiographic images of one or more regions of a patient.

In one embodiment, a compound represented by Formula II is provided.

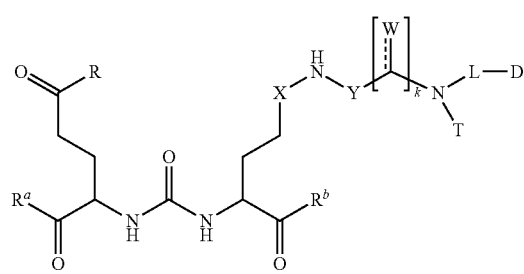

II

In Formula II, X and Y are each independently $(CHR^1)_m$ or $C(O)$, substituent W is H, O, $-(CHR^1)_m-(CH_2)_p-$, or $-(CH_2)_p-U$ and ═══ represents the option of having a double bond. Group L is $-C(O)-(C_1-C_{10})$alkylene, $-[C(O)-(CH(Z)_d)-NH]_jNR^2R^3$, $-C(O)-(CHR^1)-(CH_2)_p-U-$, $-(C_5-C_{14})$aryl-$(C_1-C_{10})$alkylene, $R^7$-benzylene, $-(C_5-C_{14})$heteroaryl-$(C_1-C_{10})$alkylene, $-C(O)-[(CH_2)_p-V]_n-(CH_2)_q-C(O)-U$, $[C(O)-CH(Z)_d-NH]_t-C(O)-(CHR^1)_m-(CH_2)_p-[U]_r$, $-C(S)-NH$-benzylene, $-C(O)-NH$-benzylene, $-[C(O)-(CH(Z)_d)-NH]_s$-benzylene-, or $-(C_1-C_{10})$alkylene-$NR^4R^5$.

In Formula II, T is H, $-(C_1-C_{10})$alkylene, $RC(O)-(C_1-C_{10})$alkylene, $NR^2R^3-(C_1-C_{10})$alkylene, $-(C_5-C_{14})$heteroaryl-$(C_1-C_{10})$alkylene, $-(C_5-C_{14})$aryl-$(C_1-C_{10})$alkylene or $R^6-(C_5-C_{14})$heteroarylene-$(C_1-C_{10})$alkylidene, with U being $-OR$, $-COR$, $-(C_5-C_{14})$arylene or $-NR^4R^5$. V, in Formula II, is $-NH-$, $-NR^2-$ or $-NR^2R^3$, and while Z is $-(CH_2)_p-COOH$, $-(CH_2)-(C_5-C_{14})$aryl, or $-(CH_2)_p-NR^2R^3$.

R, $R^a$ and $R^b$ in Formula II can each independently be $-H$, $-OH$, $-(C_1-C_{10})$alkyl, $-O(C_1-C_{10})$alkyl, $-NHR^2$, or $-NR^2R^3$; $R^1$ and $R'''$ are each independently $-H$, $-NH_2$, or $-(CH_2)_p-U$; and $R^2$, $R^3$, $R^4$, $R^5$ and $R^6$ are each independently H, bond, $(C_1-C_{10})$alkylene, F, Cl, Br, I, C(O), C(S), $-C(S)-NH$-benzyl-, $-C(O)-NH$-benzyl-, $-C(O)-(C_1-C_{10})$alkylene, $-(CH_2)_v-NR^4$, $-(CH_2)_p-NH-C(O)-(CH_2)_p-$, $-(CH_2-CH_2)_t-NH-C(O)-(CH_2)_p-$, $-(CH_2)_p-COR$, $-(CH_2)_p-C(O)NH-C[(CH_2)_p-COR]_3$, $-C[(CH_2)_p-COR]_3$, or $-(CH_2)_p-(C_5-C_{14})$heteroaryl. In Formula II, $R^7$ may be $-O(CH_2)_p-(C_5-C_{14})$heteroaryl-$(CH_2)_p-U$, and D is a chelator selected from

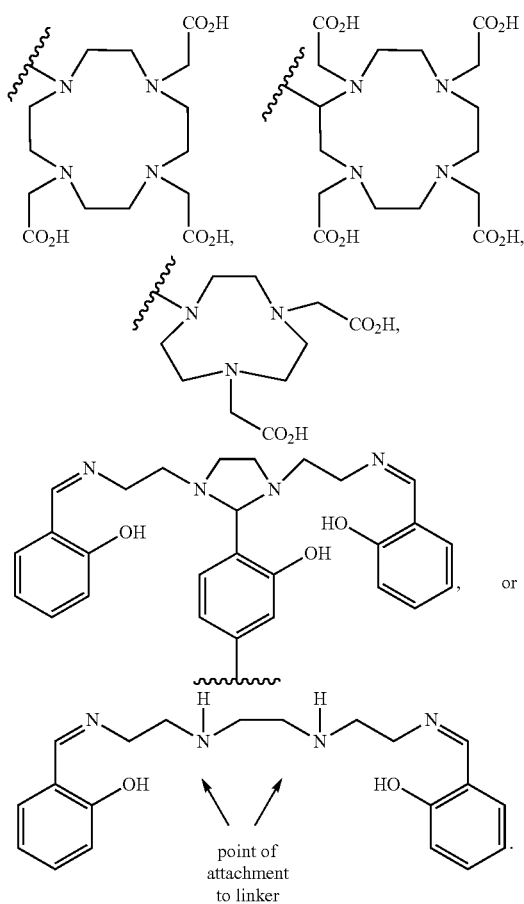

In Formula II, subscripts d, j, k, m, n, p, q, r, s, t and v are each independently 0, 1, 2, 3, 4, 5, 6, 7, 8, 9, or 10; and for compounds in accordance with this formula aryl, arylalkylene, benzyl, heteroaryl, or cycloalkyl is optionally substituted with 1, 2, or 3 substituent groups selected from the group consisting of $-(C_1-C_{10})$alkyl, halogen, $-(C_1-C_{10})$haloalkyl, $-(C_1-C_{10})$aminoalkyl, $-(C_1-C_{10})$hydroxyalkyl, $-(CH_2)_p-C(O)-U$ and $-(C_3-C_8)$cycloalkyl.

Formula II is subject to the proviso that where W is $-(CH_2)_5-$, L is not $-C(O)CH_2-$; or where W is $-CH(NH_2)-(CH_2)_4-$, L is not $-C(O)CH_2-$.

Metal complexes of any of the compounds of Formula II may also be provided. Specifically provided are radionuclide complexes of Formula II compounds. Illustrative radionuclides are moieties selected from the group consisting of $^{111}In$, $^{90}Y$, $^{68}Ga$, $^{64}Cu$, $^{153}Gd$, $^{155}Gd$, $^{157}Gd$, Fe and $^{177}Lu$. In one aspect, a compound of Formula I is provided or a pharmaceutically acceptable salt, ester or solvate thereof.

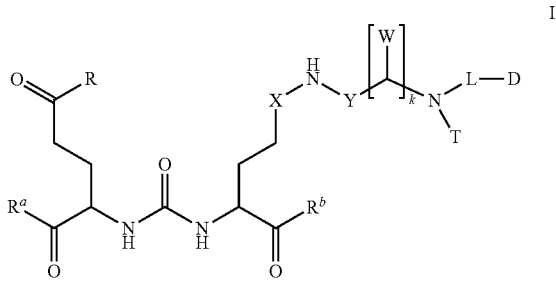

I

In the compound of Formula I, X an Y are each independently $(CHR^1)_m$ or C(O) and substituent W is H, or —$(CH_2)_p$—U.

Substituent L in Formula I is —C(O)—$(C_1-C_{10})$alkylene, —[C(O)—$(CH(Z)_d)$—NH]$_j$NR$^2$R$^3$, —C(O)—$(CHR^1)$—$(CH_2)_p$—U—, —$(C_5-C_{14})$aryl-$(C_1-C_{10})$alkylene, R$^6$O-benzylene, —$(C_5-C_{14})$heteroaryl-$(C_1-C_{10})$alkylene, —C(O)—[$(CH_2)_p$—V]$_n$—$(CH_2)_q$—C(O)—U or [C(O)—CH(Z)$_d$—NH]$_t$—C(O)—$(CHR^1)_m$—$(CH_2)_p$—U.

For Formula I compounds substituent T is H, —$(C_1-C_{10})$alkylene, RC(O)—$(C_1-C_{10})$alkylene, NR$^2$R$^3$—$(C_1-C_{10})$alkylene, —$(C_5-C_{14})$heteroaryl-$(C_1-C_{10})$alkylene or —$(C_5-C_{14})$aryl-$(C_1-C_{10})$alkylene.

For compounds according to Formula I, substituent U is —OH, —OR, —COOR or —NR$^4$R$^5$. V is —NH—, —NR$^2$— or —NR$^2$R$^3$ and Z is —$(CH_2)_p$—COOH, or —$(CH_2)_p$— NR$^2$R$^3$; R is —OH, —O$(C_1-C_{10})$alkyl, or NHR$^2$.

In Formula I R' is hydrogen, or an amino (—NH$_2$) group, while R, R$^a$ and R$^b$ are each independently —H, —OH, —$(C_1-C_{10})$alkyl, —O$(C_1-C_{10})$alkyl, or NHR$^2$.

For Formula I compounds, substituent R$^2$, R$^3$, R$^4$ and R$^5$ are each independently H, bond, $(C_1-C_{10})$alkylene, F, Cl, Br, I, C(O), C(S), —C(S)—NH-benzyl-, —C(O)—NH-benzyl-, —C(O)—$(C_1-C_{10})$alkylene, —$(CH_2)_p$—NH—C(O)—$(CH_2)_p$—, —$(CH_2-CH_2)_t$—NH—C(O)—$(CH_2)_p$—, —$(CH_2)_p$—COR, —$(CH_2)_p$—C(O)NH—C[$(CH_2)_p$—COR]$_3$, —C[$(CH_2)_p$—COR]$_3$, or —$(CH_2)_p$—$(C_5-C_{14})$heteroaryl.

When L is R$^6$O-benzylene, R$^6$ is —O$(CH_2)_p$—$(C_5-C_{14})$heteroaryl-$(CH_2)_p$—U.

The chelator D includes any linear, branched, cyclic, or alicyclic, aliphatic polyaza/polycarboxylic acid moiety that is capable of forming a metal complex with a radionuclide. In some embodiments, D includes, but is not limited to:

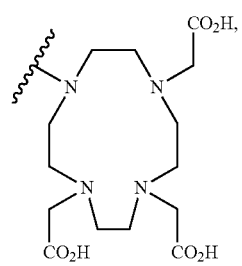

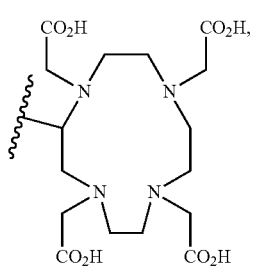

-continued

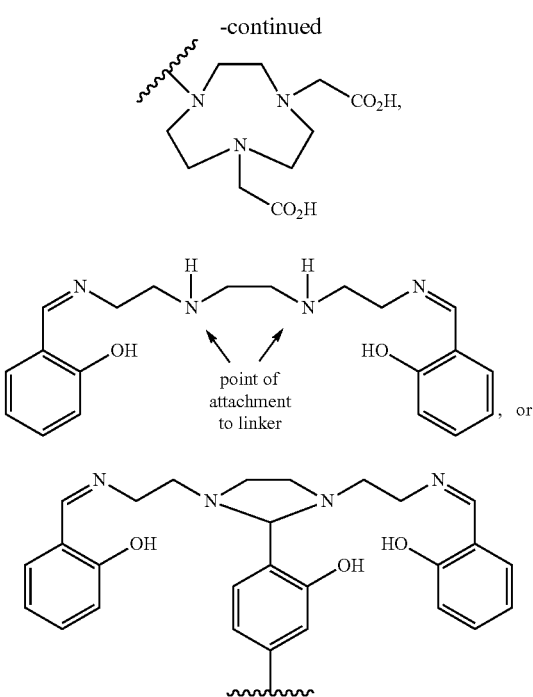

Subscripts d, j, k, m, n, p and t are integers and are each independently 0, 1, 2, 3, 4, 5, or 6.

For Formula I compounds, any aryl, heteroaryl, or cycloalkyl, are optionally substituted by 1, 2, or 3 substituent groups selected from the group consisting of —$(C_1-C_{10})$alkyl, —$(C_1-C_{10})$haloalkyl, —$(C_1-C_{10})$ aminoalkyl, —$(C_1-C_{10})$hydroxyalkyl, —$(CH_2)_p$—C(O)—U and —$(C_3-C_8)$cycloalkyl with the proviso that where W is —$(CH_2)_5$— or —CH(NH$_2$)—$(CH_2)_4$—, L is not a —C(O)CH$_2$— group.

According to certain embodiments substituent T is selected from

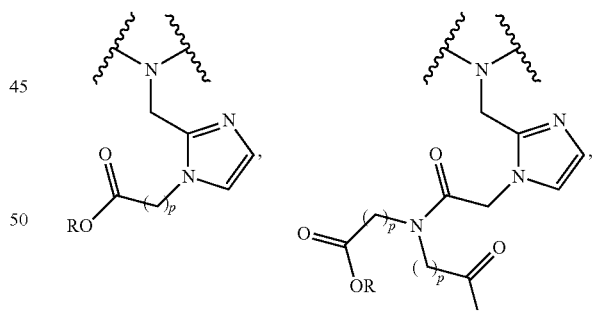

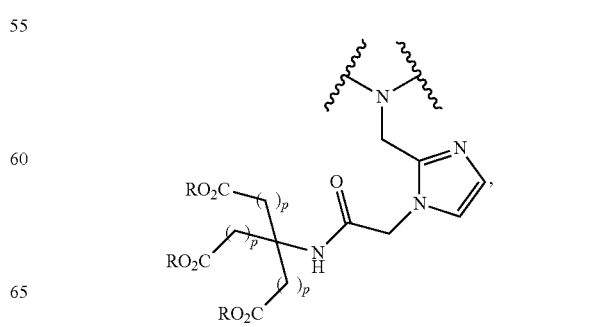

-continued

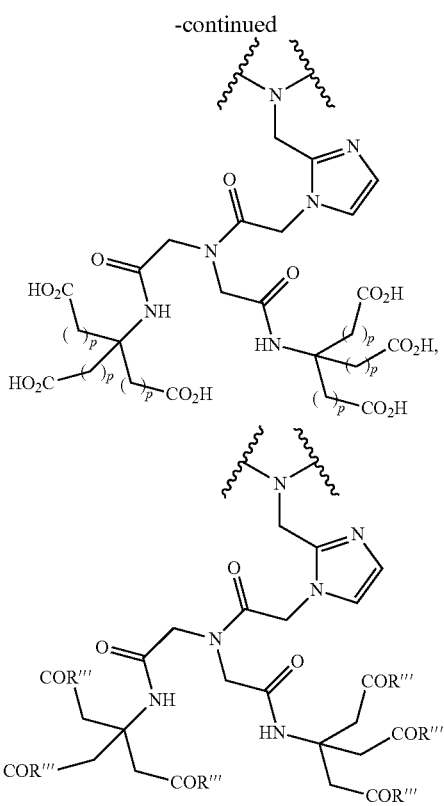

When T is

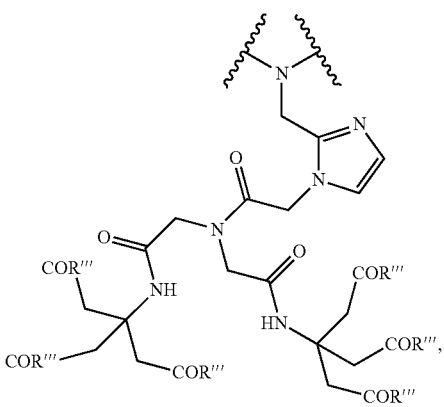

each R''' is independently

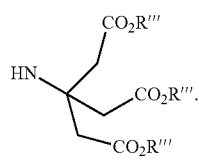

In some embodiments, the compounds of Formula I are complexed with a radionuclide. The radionuclide may include, for example, $^{111}$In, $^{90}$Y, $^{68}$Ga, $^{64}$Cu, $^{177}$Lu, $^{153}$Gd, $^{155}$Gd, $^{157}$Gd, or Fe.

For Formula I compounds that are not complexed to a radionuclide the free —C(O)OH groups of the chelator can be esterified to form a prodrug. Illustrative prodrugs include without limitation esters formed using straight or branched chain ($C_1$-$C_{10}$) alcohols, for example, ethyl esters, propyl esters, isopropyl esters and butyl esters.

Compounds and radionuclide complexes of Formula I compounds and their pharmaceutical formulations are useful for treating cell proliferative diseases, for example, prostate cancer.

In another aspect, a pharmaceutical formulation is provided including the compound of Formula I, a pharmaceutically acceptable salt or solvate thereof, and a pharmaceutically acceptable excipient.

In yet another aspect, a method of obtaining a radiographic image of one or more regions of a patient is provided by administering to the patient an effective amount of a metal complex of a Formula I compound, or a pharmaceutically acceptable salt, ester or solvate thereof, and recording an image of the one or more regions of the patient. The method may be suitable for obtaining a radiographic imaging of one or more tissues that expresses prostate-specific membrane antigen (PSMA) by contacting the one or more tissues that expresses PSMA with a metal complex comprising a radionuclide and a Formula I compound, or a pharmaceutically acceptable salt or solvate thereof; and recording a radiographic image of the one or more tissues. The described methodology may be used to image tissues such as spleen tissue, kidney tissue, or PSMA-expressing tumor tissue.

Another embodiment provides a method for obtaining a radiographic image of one or more regions of a patient by administering to the patient a compound including a first terminal group having a GUL or GUG moiety, a second terminal including a chelator moiety complexed with a radionuclide, and a linker connecting the first terminal group to the second terminal group, wherein the linker comprises at least two carboxyl moieties, each having a formula —$CO_2J$, in which each J may be the same or different and is independently selected from H, lower alkyl and a pharmaceutically acceptable organic or inorganic salt; and recording a radiographic image of one or more regions of the patient.

Illustrative of chelator moieties include without limitation

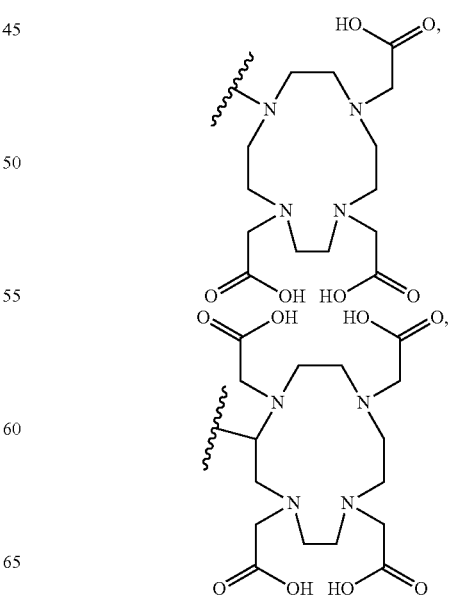

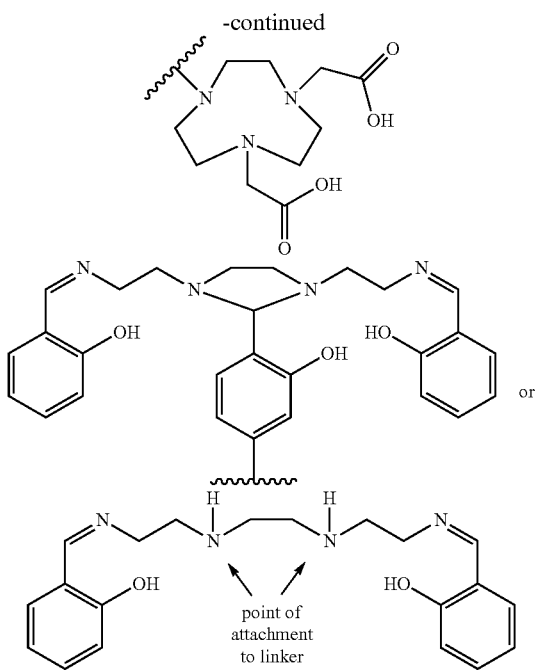

groups.

In one embodiment, therefore, the linker comprises at least three carboxyl moieties.

Another embodiment provides a linker having at least four carboxyl moieties, or a linker that has at least five carboxyl moieties.

BRIEF DESCRIPTION OF THE DRAWINGS

FIG. 1A illustrates tissue biodistribution of the $^{177}$Lu-complex of (11S,16S,20S)-11-(2-carboxyethyl)-10,13,18-trioxo-1-((4-((1,4,7,10-tetrakis(carboxymethyl)-1,4,7,10-tetraazacyclododecan-2-yl)methyl)phenyl)amino)-1-thioxo-2,9,12,17,19-pentaazadocosane-16,20,22-tricarboxylate in LNCap Xenograft mice.

FIG. 1B illustrates tissue biodistribution of the $^{177}$Lu-complex of (10S,17S,21S)-10-(naphthalen-2-ylmethyl)-8,11,19-trioxo-1-((4-((1,4,7,10-tetrakis(carboxymethyl)-1,4,7,10-tetraazacyclododecan-2-yl)methyl)phenyl)amino)-1-thioxo-2,9,12,18,20-pentaazatricosane-17,21,23-tricarboxylic acid in LNCap Xenograft mice.

FIG. 2 is a graph of the tissue biodistribution of a $^{111}$In analog of the compound of Example 3, in LNCap Xenograft mice.

DETAILED DESCRIPTION

There are two categories of radiopharmaceuticals: (i) those with biological distribution determined strictly by blood flow, or perfusion, and targeting high capacity systems such as glomerular filtration, phagocytosis, hepatocyte clearance and bone absorption and (ii) those with distribution determined by specific enzymatic or receptor binding interactions, which are low-capacity sites. The radiopharmaceuticals belong to the second category and are synthesized by conjugating the radionuclide coordination complex to a biologically active molecule selective for a particular protein or receptor of interest.

While a variety of biologically active molecules (BAM) can be used as the carriers, small molecules and small peptides have advantages over antibodies or proteins. For example, small molecules and small peptides exhibit enhanced diffusion, faster blood clearance, and lower background radiation. These carrier allow the facile synthesis of analogs in a high-throughput manner. Additionally, small peptides can be readily converted into peptide mimetics or small molecular analogs that have enhanced stability and improved affinity for the target enzyme or receptor.

In one aspect, the synthesis and methods for using PSMA selective Indium, Ytterbium, Gallium, Copper and Lutetium, Gadolinium and Iron complexes of Formula I compounds or Formula II compounds as novel radiopharmaceuticals for the treatment and imaging of cancer cells is provided. Specifically, the compounds and their radionuclide complexes are suitable for targeting carcinoma of the prostate. It is important to note that any type of radionuclide can be used so long as an appropriate metal chelating moiety is available for complexing a particular type of radionuclide.

The compounds exhibit a high affinity for PSMA expressed on the surface of prostate cancer cells. The specificity of Formula I compounds for PSMA is due to the glutamate-urea-glutamate (GUG), or glutamate-urea-lysine (GUL), recognition motif, while affinity is related to the nature and size of a linker or spacer group conjugating the GUL or GUG moiety to a radionuclide chelator.

The terms "linker," "spacer," "linker group" or "spacer group" are used interchangeably in this document and refer to a group that spans the distance between two other identified groups, or which "spaces" them apart. The linker or spacer may be a bond, an organic group, or an inorganic group or atom. In some embodiments, the linker or spacer is an optionally substituted ($C_1$-$C_{15}$)alkylene, a ($C_2$-$C_{15}$)alkenylene, or a ($C_2$-$C_{15}$)alkynylene group. Illustrative substituent groups include without limitation carboxyl groups, carboxylate, hydroxyl groups, and amino ($NR^2R^3$) groups. In other embodiments, the linker or spacer is a ($C_1$-$C_{15}$)polyol, for example, a polyethylene glycol (PEG) moiety. In yet other embodiments, the linker or spacer includes a backbone of any two or more of alkyl, nitrogen, carbonyl, and oxygen groups. Such linker or spacer groups are illustrated throughout the examples, although the examples are only illustrative of the many types of linkers/spacers that may be used.

Without ascribing to any particular theory, however, the present inventors believe that hydrophilic or polar functional groups within the spacer or pendant from the spacer moiety are responsible for enhancing the affinity of a compound according to the present invention for PSMA. It is also an object of the present invention to provide synthetic methodologies that provide access to a class of Formula I compounds having varying levels of functionality in a rapid synthetically accessible manner.

DEFINITIONS

For convenience, certain terms employed herein and within the appended claims are defined here.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The use of the terms "a" and "an" and "the" and similar referents in the context of describing the elements (especially in the context of the following claims) are to be construed to cover both the singular and the plural, unless otherwise indicated herein or clearly contradicted by context.

The terms "lipophilic group" and "lipophilic moiety" as used herein refer to a group, moiety or substituent that has a greater affinity for non-polar or non-aqueous environments versus polar or aqueous environments. For example, Merriam Webster's online dictionary defines "lipophilic" as "having an affinity for lipids (as fats)." Illustrative lipophilic moieties include aliphatic hydrocarbon radicals, e.g., alkyl radicals, aromatic hydrocarbon radicals, and long-chain acyl radicals; all of them have increasing lipophilicity as the number of constituent carbons increases. In general, addition of a lipophilic moiety to a particular compound will increase the compound's affinity for octanol in the standard octanol/water partition-coefficient-determination protocol; this protocol may be used to gauge a compound's relative hydrophobicity (lipophilicity) and hydrophilicity.

The terms "Lewis base" and "Lewis basic" refer to a chemical moiety capable of donating a pair of electrons under certain reaction conditions. It may be possible to characterize a Lewis base as donating a single electron in certain complexes, depending on the identity of the Lewis base and the metal ion, but for most purposes, however, a Lewis base is best understood as a two electron donor. Examples of Lewis basic moieties include uncharged compounds such as alcohols, thiols, and amines, and charged moieties such as alkoxides, thiolates, carbanions, and a variety of other organic anions. In certain examples, a Lewis base may consist of a single atom, such as oxide ($O_2^-$). In certain, less common circumstances, a Lewis base or ligand may be positively charged. A Lewis base, when coordinated to a metal ion, is often referred to as a ligand.

The term "ligand" refers to a species that interacts in some fashion with another species. In one example, a ligand may be a Lewis base that is capable of forming a coordinate bond with a Lewis Acid. In other examples, a ligand is a species, often organic, that forms a coordinate bond with a metal ion. Ligands, when coordinated to a metal ion, may have a variety of binding modes know to those of skill in the art, which include, for example, terminal (i.e., bound to a single metal ion) and bridging (i.e., one atom of the Lewis base bound to more than one metal ion).

The term "chelating agent" refers to a molecule, often an organic one, and often a Lewis base, having two or more unshared electron pairs available for donation to a metal ion. The metal ion is usually coordinated by two or more electron pairs to the chelating agent. The terms, "bidentate chelating agent", "tridentate chelating agent", and "tetradentate chelating agent" are art-recognized and refer to chelating agents having, respectively, two, three, and four electron pairs readily available for simultaneous donation to a metal ion coordinated by the chelating agent. Usually, the electron pairs of a chelating agent forms coordinate bonds with a single metal ion; however, in certain examples, a chelating agent may form coordinate bonds with more than one metal ion, with a variety of binding modes being possible.

The term "coordination" refers to an interaction in which one multi-electron pair donor coordinatively bonds (is "coordinated") to one metal ion.

The term radionuclide refers to an atom with an unstable nucleus, which is a nucleus characterized by excess energy available to be imparted either to a newly created radiation particle within the nucleus or to an atomic electron. The radionuclide can undergo radioactive decay and in the process emit subatomic ionizing particles. Illustrative of subatomic ionizing particles without limitation are alpha ($\alpha$) particles, beta ($\beta$) particle and gamma ($\gamma$) rays. Illustrative radionuclides may include, but are not limited to $^{111}$In, $^{90}$Y, $^{68}$Ga, $^{64}$Cu, $^{171}$Lu, $^{153/157/158}$Gd, or Fe. However, the term is not limited to these four radionuclides.

Fmoc is an abbreviation for the chemical group: fluorenylmethyloxycarbonyl.

The phrases "effective amount" or "therapeutically-effective amount" as used herein means that amount of a compound, material, or composition comprising a compound of the invention, or other active ingredient which is effective for producing some desired therapeutic effect in at least a sub-population of cells in an animal at a reasonable benefit/risk ratio applicable to any medical treatment. A therapeutically effective amount with respect to a compound of the invention means that amount of therapeutic agent alone, or in combination with other therapies, that provides a therapeutic benefit in the treatment or prevention of a disease. Used in connection with a compound of the invention, the term can encompass an amount that improves overall therapy, reduces or avoids symptoms or causes of disease, or enhances the therapeutic efficacy of or synergies with another therapeutic agent.

As used herein, the terms "treating" or "treatment" is intended to encompass also diagnosis, prophylaxis, therapy and cure. The patient receiving this treatment is any animal in need, including primates, in particular humans, and other mammals such as equines, cattle, swine and sheep; and poultry and pets in general.

The terms "prevent," "preventing," and "prevention" refer to the prevention of the onset, recurrence, or spread of the disease in a patient resulting from the administration of a prophylactic or therapeutic agent.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

A "pharmaceutically acceptable salt" is a pharmaceutically acceptable, organic or inorganic acid or base salt of a compound of the invention. Representative pharmaceutically acceptable salts include, e.g., alkali metal salts, alkali earth salts, ammonium salts, water-soluble and water-insoluble salts, such as the acetate, amsonate (4,4-diaminostilbene-2, 2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fumarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts. A pharmaceutically acceptable salt can have more than one charged atom in its structure. In this instance the pharmaceutically acceptable salt can have multiple counterions. Thus, a pharmaceutically acceptable salt can have one or more charged atoms and/or one or more counterions.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

The term "amino acid" refers to all compounds, whether natural or synthetic, which include both an amino functionality and an acid functionality, including amino acid analogs and derivatives. Illustrative of compounds that fall within this genus without limitation are L-amino acide, D-amino acids, α-amino acids, β-amino acid, as well as γ-amino acids.

A "patient" includes an animal, such as a human, cow, horse, sheep, lamb, pig, chicken, turkey, quail, cat, dog, mouse, rat, rabbit or guinea pig. The animal can be a mammal such as a non-primate and a primate (e.g., monkey and human). In one embodiment, a patient is a human, such as a human infant, child, adolescent or adult.

The term "prodrug" refers to a precursor of a drug that is a compound which upon administration to a patient, must undergo chemical conversion by metabolic processes before becoming an active pharmacological agent. Illustrative prodrugs of compounds in accordance with Formula I are esters and amides, preferably alkyl esters or fatty acid esters.

The term "heteroatom" refers to an atom of any element other than carbon or hydrogen. Illustrative heteroatoms include boron, nitrogen, oxygen, phosphorus, sulfur and selenium.

In general, "substituted" refers to an alkyl or alkenyl group, as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group will be substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyls; alkoxy, alkenoxy, alkynoxy, aryloxy, aralkyloxy, heterocyclyloxy, and heterocyclylalkoxy groups; carbonyls (oxo); carboxyls; esters; urethanes; oximes; hydroxylamines; alkoxyamines; aralkoxyamines; thiols; sulfides; sulfoxides; sulfones; sulfonyls; sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN), haloalkyl, aminoalkyl, hydroxyalkyl, cycloalkyl and the like.

Alkyl groups include straight chain and branched chain alkyl groups having from 1 to 12 carbon atoms, and typically from 1 to 10 carbons or, in some embodiments, from 1 to 8, 1 to 6, or 1 to 4 carbon atoms. Examples of straight chain alkyl groups include groups such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups. Alkyl groups may be substituted or unsubstituted. Unless the number of carbons is otherwise specified, "lower alkyl" refers to an alkyl group, as defined above, but having from one to about ten carbons, alternatively from one to about six carbon atoms in its backbone structure. Likewise, "lower alkenyl" and "lower alkynyl" have similar chain lengths.

The terms "alkylene" and "substituted alkylene" refer to divalent alkyl and divalent substituted alkyl, respectively. Examples of alkylene include without limitation, ethylene (—$CH_2$—$CH_2$—). "Optionally substituted alkylene" refers to alkylene or substituted alkylene.

The term "alkylcarbonyl" denotes an —($C_1$-$C_8$)alkyl-C(O) group in which one or more methylenes in the $C_1$-$C_8$ alkyl group is replaced with a C(O) group. Representative examples include, but are not limited to, acetyl, propionyl, and $CH_3(CH_2)_2C(O)$— group.

The terms "cyclic alkyl" or "cycloalkyl" refers to a saturated or partially saturated non-aromatic cyclic alkyl groups of from 3 to 14 carbon atoms and no ring heteroatoms and having a single ring or multiple rings including fused and bridged ring systems. Cycloalkyl groups may be substituted or unsubstituted. Cycloalkyl or cyclic alkyl groups include mono-, bi- or tricyclic alkyl groups having from 3 to 14 carbon atoms in the ring(s), or, in some embodiments, 3 to 12, 3 to 10, 3 to 8, or 3 to 4, 5, 6 or 7 carbon atoms. Illustrative monocyclic cycloalkyl groups include, but not limited to, cyclopropyl, cyclobutyl, cyclopentyl, cyclohexyl, cycloheptyl, and cyclooctyl groups. Bi- and tricyclic ring systems include both bridged cycloalkyl groups and fused rings, such as, but not limited to, bicyclo[2.1.1]hexane, adamantyl, decalinyl, and the like.

Alkenyl groups include straight and branched chain and cycloalkyl groups as defined above, except that at least one double bond exists between two carbon atoms. Thus, alkenyl groups have from 2 to about 12 carbon atoms in some embodiments, from 2 to 10 carbon atoms in other embodiments, and from 2 to 8 carbon atoms in other embodiments. Examples include, but are not limited to vinyl, allyl, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, cyclohexenyl, cyclopentenyl, cyclohexadienyl, butadienyl, pentadienyl, and hexadienyl, among others. Alkenyl groups may be substituted or unsubstituted. Representative substituted alkenyl groups may be mono-substituted or substituted more than once, such as, but not limited to, mono-, di- or tri-substituted with substituents such as those listed above.

The term "alkenylene" refers to divalent alkene. Examples of alkenylene include without limitation, ethenylene (—CH=CH—) and all stereoisomeric and conformational isomeric forms thereof. "Substituted alkenylene" refers to divalent substituted alkene. "Optionally substituted alkenylene" refers to alkenylene or substituted alkenylene.

"Alkyne" or "alkynyl" refers to straight and branched chain unsaturated hydrocarbon having the indicated number of carbon atoms and at least one triple bond. Examples of a (C$_2$-C$_8$)alkynyl group include, but are not limited to, acetylene, propyne, 1-butyne, 2-butyne, 1-pentyne, 2-pentyne, 1-hexyne, 2-hexyne, 3-hexyne, 1-heptyne, 2-heptyne, 3-heptyne, 1-octyne, 2-octyne, 3-octyne and 4-octyne. An alkynyl group can be unsubstituted or optionally substituted with one or more substituents as described herein below.

The term "alkynylene" refers to divalent alkyne. Examples of alkynylene include without limitation, ethynylene, propynylene. "Substituted alkynylene" refers to divalent substituted alkyne.

Aryl groups are cyclic aromatic hydrocarbons that do not contain heteroatoms. Aryl groups include monocyclic, bicyclic and polycyclic ring systems. Thus, aryl groups include, but are not limited to, phenyl, azulenyl, heptalenyl, biphenylenyl, indacenyl, fluorenyl, phenanthrenyl, triphenylenyl, pyrenyl, naphthacenyl, chrysenyl, biphenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. Aryl group includes both substituted and unsubstituted aryl groups. Substituted aryl groups may be mono-substituted or substituted more than once. For example, monosubstituted aryl groups include, but are not limited to, 2-, 3-, 4-, 5-, or 6-substituted phenyl or naphthyl groups, which may be substituted with substituent groups such as those listed above.

Aralkyl groups are alkyl groups as defined above in which a hydrogen or carbon bond of an alkyl group is replaced with a bond to an aryl group as defined above. In some embodiments, aralkyl groups contain 7 to 20 carbon atoms, 7 to 14 carbon atoms or 7 to 10 carbon atoms.

"Heterocyclyl" or heterocycloalkyl refers to non-aromatic ring compounds containing 3 or more ring members, of which one or more ring carbon atoms are replaced with a heteroatom such as, but not limited to, N, O, and S. In some embodiments, heterocyclyl groups include 3 to 20 ring members, whereas other such groups have 3 to 6, 3 to 10, 3 to 12, or 3 to 15 ring members. Heterocyclyl groups encompass unsaturated, partially saturated and saturated ring systems, such as, for example, imidazolyl, imidazolinyl and imidazolidinyl groups. Heterocyclyl groups may be substituted or unsubstituted. Heterocyclyl groups include, but are not limited to, aziridinyl, azetidinyl, pyrrolidinyl, imidazolidinyl, pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, thiazolyl, thiazolinyl, isothiazolyl, thiadiazolyl, oxadiazolyl, piperidyl, piperazinyl, morpholinyl, thiomorpholinyl, tetrahydropyranyl, tetrahydrothiopyranyl, oxathiane, dioxyl, dithianyl, pyranyl, pyridyl, pyrimidinyl, pyridazinyl, pyrazinyl, triazinyl, dihydropyridyl, dihydrodithiinyl, dihydrodithionyl, homopiperazinyl, quinuclidyl, indolyl, indolinyl, isoindolyl, azaindolyl (pyrrolopyridyl), indazolyl, indolizinyl, benzotriazolyl, benzimidazolyl, benzofuranyl, benzothiophenyl, benzthiazolyl, benzoxadiazolyl, benzoxazinyl, benzodithiinyl, benzoxathiinyl, benzothiazinyl, benzoxazolyl, benzothiazolyl, benzothiadiazolyl, benzo[1,3]dioxolyl, pyrazolopyridyl, imidazopyridyl (azabenzimidazolyl), triazolopyridyl, isoxazolopyridyl, purinyl, xanthinyl, adeninyl, guaninyl, quinolinyl, isoquinolinyl, quinolizinyl, quinoxalinyl, quinazolinyl, cinnolinyl, phthalazinyl, naphthyridinyl, pteridinyl, thianaphthalenyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, and tetrahydroquinolinyl groups. Heterocyclyl groups may be substituted or unsubstituted. Representative substituted heterocyclyl groups may be mono-substituted or substituted more than once, such as, but not limited to, pyridyl or morpholinyl groups, which are 2-, 3-, 4-, 5-, or 6-substituted, or disubstituted with various substituents such as those listed above.

Heteroaryl groups are aromatic ring compounds containing 5 or more ring members, of which, one or more ring carbon atoms are replaced with heteroatom such as, but not limited to, N, O, and S. Heteroaryl groups may be substituted or unsubstituted. Heteroaryl groups include, but are not limited to, groups such as pyrrolyl, pyrazolyl, triazolyl, tetrazolyl, oxazolyl, isoxazolyl, thiazolyl, pyridyl, pyridazinyl, pyrimidinyl, pyrazinyl, thiophenyl, benzothiophenyl, furanyl, benzofuranyl, indolyl, azaindolyl (pyrrolopyridyl), indazolyl, benzimidazolyl, imidazopyridyl (azabenzimidazolyl), pyrazolopyridyl, triazolopyridyl, benzotriazolyl, benzoxazolyl, benzothiazolyl, benzothiadiazolyl, imidazopyridyl, isoxazolopyridyl, thianaphthalenyl, purinyl, xanthinyl, adeninyl, guaninyl, quinolinyl, isoquinolinyl, tetrahydroquinolinyl, quinoxalinyl, and quinazolinyl groups.

Alkoxy groups are hydroxyl groups (—OH) in which the bond to the hydrogen atom is replaced by a bond to a carbon atom of a substituted or unsubstituted alkyl group as defined above. Examples of linear alkoxy groups include but are not limited to methoxy, ethoxy, propoxy, butoxy, pentoxy, hexoxy, and the like. Examples of branched alkoxy groups include but are not limited to isopropoxy, sec-butoxy, tert-butoxy, isopentoxy, isohexoxy, and the like. Examples of cycloalkoxy groups include but are not limited to cyclopropyloxy, cyclobutyloxy, cyclopentyloxy, cyclohexyloxy, and the like. Alkoxy groups may be substituted or unsubstituted. Representative substituted alkoxy groups may be substituted one or more times with substituents such as those listed above.

The term "carbocycle" refers to an aromatic or non-aromatic ring in which each atom of the ring is carbon.

The term "nitro" refers to —NO$_2$; the term "halogen" is art-recognized and refers to —F, —Cl, —Br or —I; the term "sulfhydryl" is art-recognized and refers to —SH; the term "hydroxyl" means —OH; and the term "sulfonyl" is art-recognized and refers to —SO$_2^-$. "Halide" designates the corresponding anion of the halogens, and "pseudohalide" has the definition set forth on 560 of "Advanced Inorganic Chemistry" by Cotton and Wilkinson.

The term "amine or amino" refers to an —NR$^c$R$^d$ group wherein R$^c$ and R$^d$ each independently refer to a hydrogen, (C$_1$-C$_8$)alkyl, aryl, heteroaryl, and heterocycloalkyl group. When R$^c$ and R$^d$ are attached to the same nitrogen atom, they can be combined with the nitrogen atom to form a 5-, 6-, or 7-membered ring. For example, —NR$^c$R$^d$ is meant to include 1-pyrrolidinyl, pyridinyl or a 4-morpholinyl ring.

The term "amido" is art recognized as an amino-substituted carbonyl and includes a moiety that may be represented by the general formula, —C(O)NR$^c$R$^d$ group wherein R$^c$ and R$^d$ are as defined above. According to some embodiments, the amide does not include imides which may be unstable.

The term 'nitrile or cyano" can be used interchangeably and refer to a —CN group which is bound to a carbon atom of a heteroaryl ring, aryl ring and a heterocycloalkyl ring.

The term "aminoalkyl," refers to an (C$_1$-C$_{10}$)alkyl group wherein one or more hydrogen atoms in the (C$_1$-C$_{10}$)alkyl group is replaced with a —NR$^d$R$^e$ group, where R$^d$ and R$^e$ can be the same or different, for example, R$^d$ and R$^e$ each independently refer to a hydrogen, (C$_1$-C$_8$)alkyl, aryl, heteroaryl, heterocycloalkyl, (C$_1$-C$_8$)haloalkyl, and (C$_1$-C$_{10}$)hydroxyalkyl group. Examples of aminoalkyl groups include, but are not limited to, aminomethyl, aminoethyl, 4-aminobutyl and 3-aminobutylyl.

The term "haloalkoxy," refers to an —O—(C$_1$-C$_8$)alkyl group wherein one or more hydrogen atoms in the C$_1$-C$_8$ alkyl group is replaced with a halogen atom, which can be the same or different. Examples of haloalkyl groups include, but are not limited to, difluoromethocy, trifluoromethoxy, 2,2,2-trifluoroethoxy, 4-chlorobutoxy, 3-bromopropyloxy, pentachloroethoxy, and 1,1,1-trifluoro-2-bromo-2-chloro ethoxy.

The term "hydroxyalkyl," refers to an alkyl group having the indicated number of carbon atoms wherein one or more of the alkyl group's hydrogen atoms is replaced with an —OH group. Examples of hydroxyalkyl groups include, but are not limited to, —CH$_2$OH, —CH$_2$CH$_2$OH, —CH$_2$CH$_2$CH$_2$OH, —CH$_2$CH$_2$CH$_2$CH$_2$OH, —CH$_2$CH$_2$CH$_2$CH$_2$CH$_2$OH, —CH$_2$CH$_2$CH$_2$CH$_2$CH$_2$CH$_2$OH, and branched versions thereof.

A "hydroxyl" or "hydroxy" refers to an —OH group.

The terms "carboxyl" and "carboxylate" include such moieties as may be represented by the general formulas:

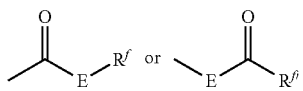

wherein E is a bond or represents O or S, and R$^f$ and R$^{f'}$ individually is H, alkyl, alkenyl, aryl, or a pharmaceutically acceptable salt. Where E is O, and R$^f$ is as defined above, the moiety is referred to herein as a carboxyl group, and particularly when R$^f$ is a hydrogen, the formula represents a "carboxylic acid". In general, where the expressly shown oxygen is replaced by sulfur, the formula represents a "thiocarbonyl" group.

The substituent —CO$_2$H, may be replaced with bioisosteric replacements such as:

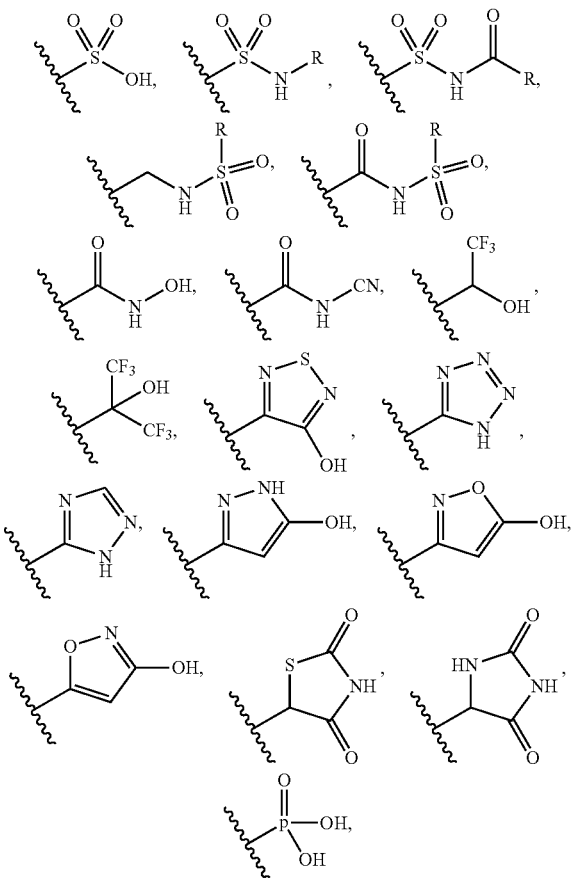

and the like, wherein R has the same definition as R' and R" as defined herein. See, e.g., THE PRACTICE OF MEDICINAL CHEMISTRY (Academic Press: New York, 1996), at page 203.

The terms "alkoxyl" or "alkoxy" refer to an alkyl group, as defined above, having an oxygen radical attached thereto. Representative alkoxyl groups include methoxy, ethoxy, propoxy, butyoxy, tert-butoxy and the like. An "ether" is two hydrocarbons covalently linked by an oxygen. "Ether" also encompasses polyethers where more than one ether group, or linkage, may be present in a given group. "Ether" also encompasses cyclic ethers, and crown ethers, where the ether linkage is within a cyclic group.

The term "(C$_5$-C$_{14}$)aryl-(C$_1$-C$_{10}$)alkylene" refers to a divalent alkylene wherein one or more hydrogen atoms in the C$_1$-C$_{10}$ alkylene group is replaced by a (C$_3$-C$_{14}$)aryl group. Examples of (C$_3$-C$_{14}$)aryl-(C$_1$-C$_{10}$)alkylene groups include without limitation 1-phenylbutylene, phenyl-2-butylene, 1-phenyl-2-methylpropylene, phenylmethylene, phenylpropylene, and naphthylethylene.

The term "(C$_5$-C$_{14}$)heteroaryl-(C$_1$-C$_{10}$)alkylene" refers to a divalent alkylene wherein one or more hydrogen atoms in the C$_1$-C$_{10}$ alkylene group is replaced a (C$_3$-C$_{14}$)heteroaryl group. Examples of (C$_3$-C$_{14}$)heteroaryl-(C$_1$-C$_{10}$)alkylene groups include without limitation 1-pyridylbutylene, quinolinyl-2-butylene and 1-pyridyl-2-methylpropylene.

The term "—(C$_5$-C$_{14}$)heteroarylene-(C$_1$-C$_{10}$)alkylene-" refers to a divalent alkylene wherein one or more hydrogen atoms in the C$_1$-C$_{10}$ alkylene group is replaced a (C$_3$-C$_{14}$) heteroaryl group and wherein one of the hydrogens or one of the heteroatoms of the (C$_3$-C$_{14}$)heteroaryl group is bonded to another group, for example, a (C$_1$-C$_{10}$)alkyl group.

A "benzyl" is

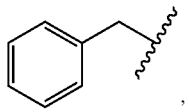

while the term "benzylene" denotes a divalent benzyl moiety that is represented by the following structure

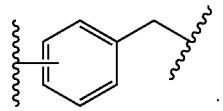

A halogen refers to chlorine, bromine, fluorine, or iodine.

The definition of each expression, e.g. alkyl, m, n, and the like, when it occurs more than once in any structure, is intended to be independent of its definition elsewhere in the same structure.

The terms triflyl, tosyl, mesyl, and nonaflyl refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain the groups, respectively. The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the Journal of Organic Chemistry; this list is typically presented in a table entitled Standard List of Abbreviations.

Certain compounds contained in the compositions may exist in particular geometric or stereoisomeric forms. In addition, compounds may also be optically active. The compounds may also include cis- and trans-isomers, R- and S-enantiomers, diastereomers, (D)-isomers, (L)-isomers, the racemic mixtures thereof, and other mixtures thereof. Additional asymmetric carbon atoms may be present in a substituent such as an alkyl group. If, for instance, a particular enantiomer of compound is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, 3rd ed.; Wiley: New York, 1999).

Unless otherwise indicated, "stereoisomer" means one stereoisomer of a compound that is substantially free of other stereoisomers of that compound. Thus, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, for example greater than about 90% by weight of one stereoisomer of the compound and less than about 10% by weight of the other stereoisomers of the compound, or greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound.

If there is a discrepancy between a depicted structure and a name given that structure, then the depicted structure controls. Additionally, if the stereochemistry of a structure or a portion of a structure is not indicated with, for example, bold or dashed lines, the structure or portion of the structure is to be interpreted as encompassing all stereoisomers of it.

Chelator Compounds and their Synthesis

The present technology is directed to Formula I and Formula II compounds and their pharmaceutically acceptable salts, esters or solvates. Both Formula I and Formula II compounds are potent ligands for radioimaging applications and for radiotherapeutic applications of PSMA expressing prostate cancer tissue. The compounds include a first terminal group and a second terminal group that are connected using a linker or spacer. The first terminal group is a tripeptide comprising a glutamic-urea-lysine (GUL), or glutamic-urea-glutamic (GUG) moiety (see below), while the second terminal group comprises a radionuclide chelator.

In one embodiment, the compounds are represented by Formula II.

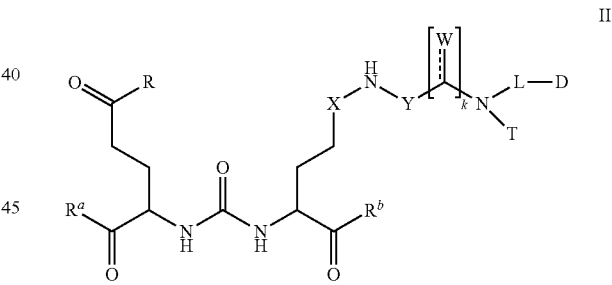

II

In Formula II, X and Y are each independently $(CHR^1)_m$ or $C(O)$, substituent W is H, O, $—(CHR^1)_m—(CH_2)_p—$, or $—(CH_2)_p—U$ and ═══ represents the option of having a double bond. Group L is selected from $—C(O)—(C_1-C_{10})$alkylene, $—[C(O)—(CH(Z)_d)—NH]_jNR^2R^3$, $—C(O)—(CHR^1)—(CH_2)_p—U—$, $—(C_5-C_{14})$aryl-$(C_1-C_{10})$alkylene, $R^7$-benzylene, $—(C_5-C_{14})$heteroaryl-$(C_1-C_{10})$alkylene, $—C(O)—[(CH_2)_n—V]_n—(CH_2)_q—C(O)—U$, $[C(O)—CH(Z)_d—NH]_t—C(O)—(CHR^1)_m—(CH_2)_p—[U]_r$, $—C(S)—NH$-benzylene, $—C(O)—NH$-benzylene, $—[C(O)—(CH(Z)_d)—NH]_s$-benzylene-, or $—(C_1-C_{10})$alkylene-$NR^4R^5$.

In Formula II, T is selected from the group consisting of H, $—(C_1-C_{10})$alkylene, $RC(O)—(C_1-C_{10})$alkylene, $NR^2R^3—(C_1-C_{10})$alkylene, $—(C_5-C_{14})$heteroaryl-$(C_1-C_{10})$alkylene, $—(C_5-C_{14})$aryl-$(C_1-C_{10})$alkylene and $R^6—(C_5-C_{14})$heteroarylene-$(C_1-C_{10})$alkylidene, with U being selected from the group consisting of $—OR$, $—COR$, $—(C_5-C_{14})$arylene and $—NR^4R^5$.

Substituent V is selected from the group consisting of —NH—, —NR² — and —NR²R³, while group Z can be —(CH₂)$_p$—COOH, —(CH₂)$_p$—(C₅-C₁₄)aryl, or —(CH₂)$_p$—NR²R³.

R, R$^a$ and R$^b$ in Formula II compounds can each independently be —H, —OH, —(C₁-C₁₀)alkyl, —O(C₁-C₁₀)alkyl, —NHR², or —NR²R³. Substituents R¹ and R'" are each independently —H, —NH₂, or —(CH₂)$_p$—U and groups R², R³, R⁴, R⁵ and R⁶ each independently being H, bond, (C₁-C₁₀) alkylene, F, Cl, Br, I, C(O), C(S), —C(S)—NH-benzyl-, —C(O)—NH-benzyl-, —C(O)—(C₁-C₁₀)alkylene, —(CH₂)$_v$—NR⁴, —(CH₂)$_p$—NH—C(O)—(CH₂)$_p$—, —(CH₂—CH₂)$_t$—NH—C(O)—(CH₂)$_p$—, —(CH₂)$_p$—COR, —(CH₂)$_p$—C(O)NH—C[(CH₂)$_p$—COR]₃, —C[(CH₂)$_p$—COR]₃, or —(CH₂)$_p$(C₅-C₁₄)heteroaryl with R⁷ in Formula II being —O(CH₂)$_p$—(C₅-C₁₄)heteroaryl-(CH₂)$_p$—U.

To form complexes, Formula II provides chelator group D that can interact and complex radionuclides. Illustrative of such chelators are compounds selected from

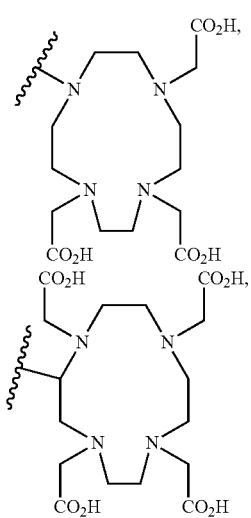

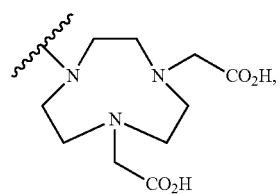

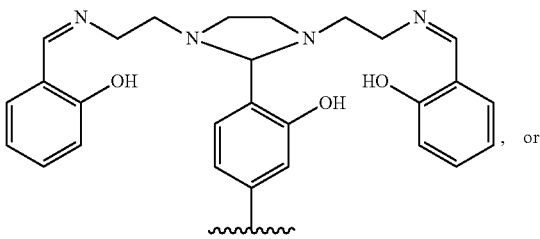

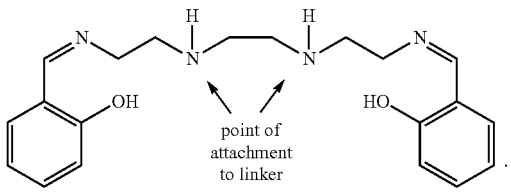

In Formula II, subscripts d, j, k, m, n, p, q, r, s, t and v are each independently 0, 1, 2, 3, 4, 5, 6, 7, 8, 9, or 10. Moreover, any aryl, arylalkylene, benzyl, heteroaryl, or cycloalkyl in a Formula II compound can optionally be substituted with 1, 2, or 3 substituent groups selected from the group consisting of —(C₁-C₁₀)alkyl, halogen, —(C₁-C₁₀)haloalkyl, —(C₁-C₁₀)aminoalkyl, —(C₁-C₁₀)hydroxyalkyl, —(CH₂)$_p$—C(O)—U and —(C₃-C₈)cycloalkyl.

Illustrative compounds of Formula II include, but are not limited to:

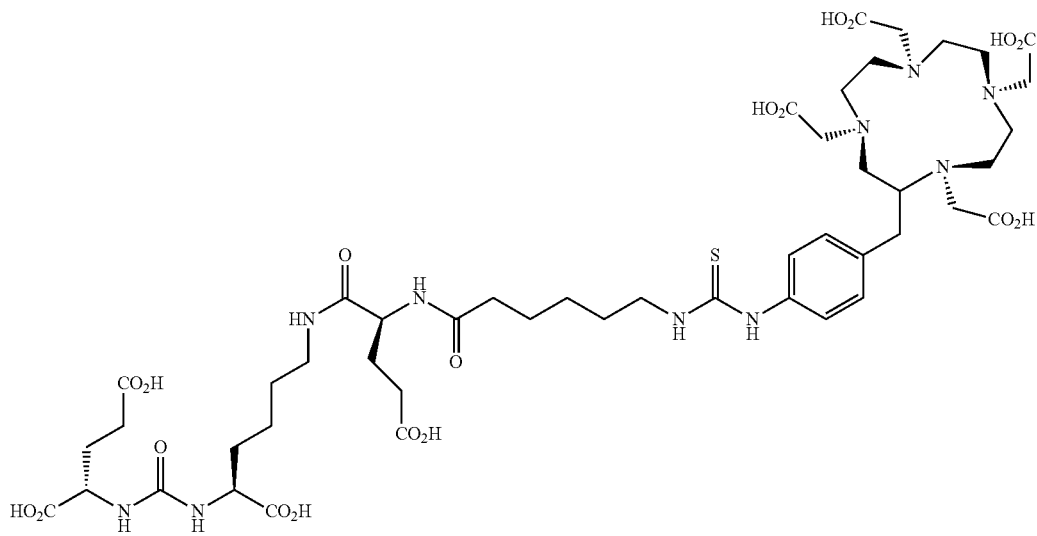

23
24
-continued
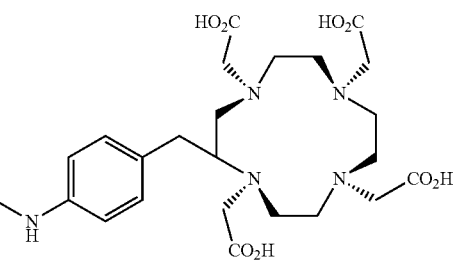
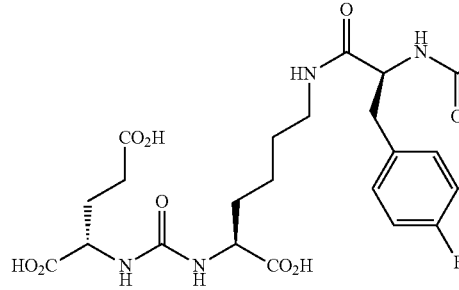
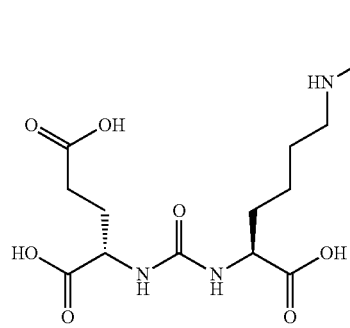
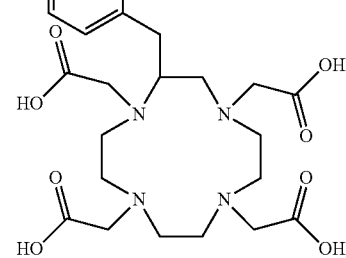
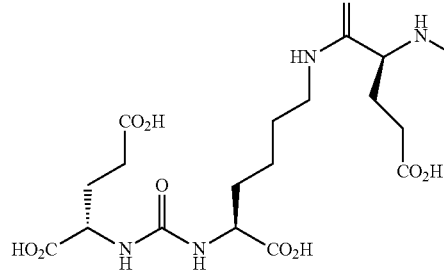
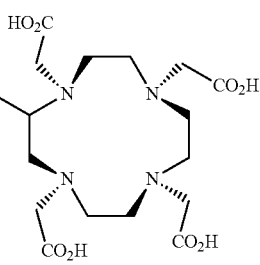
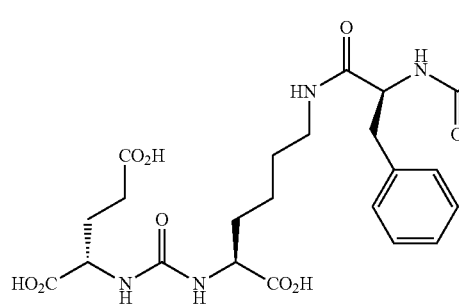
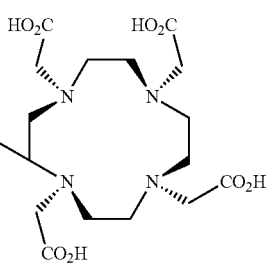

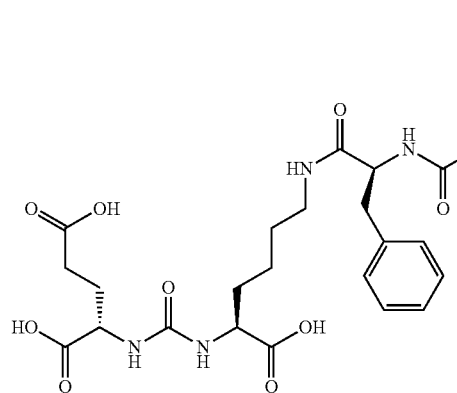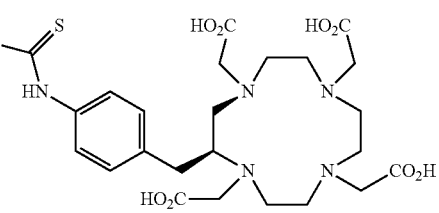
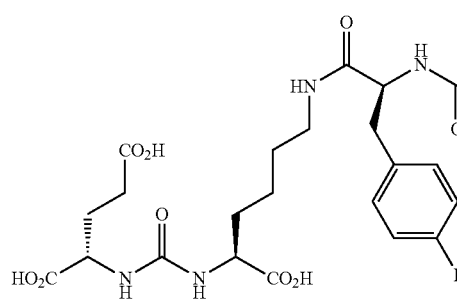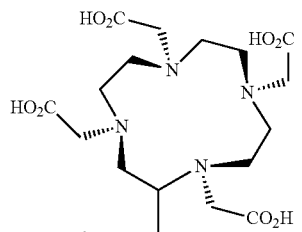
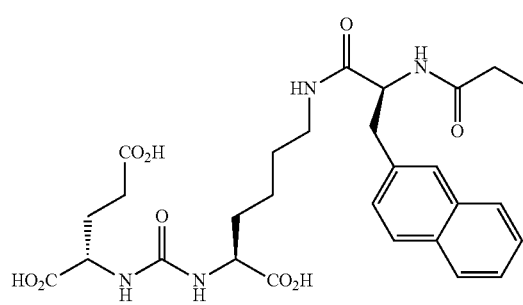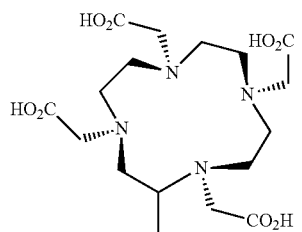

-continued
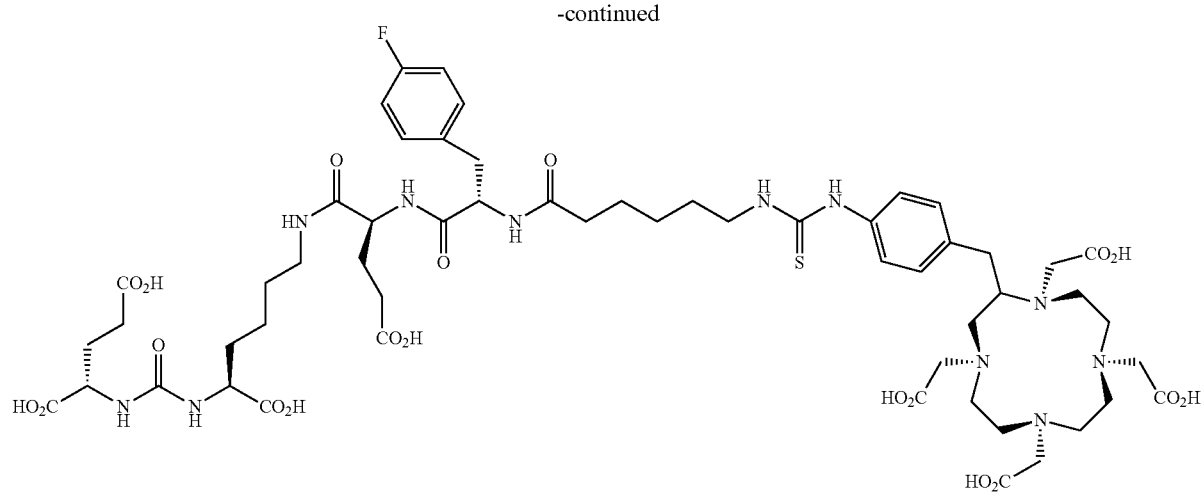
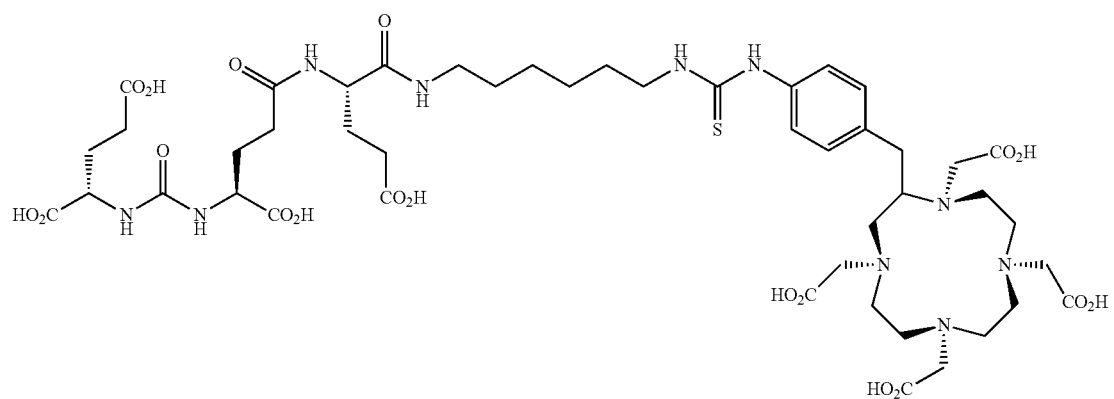
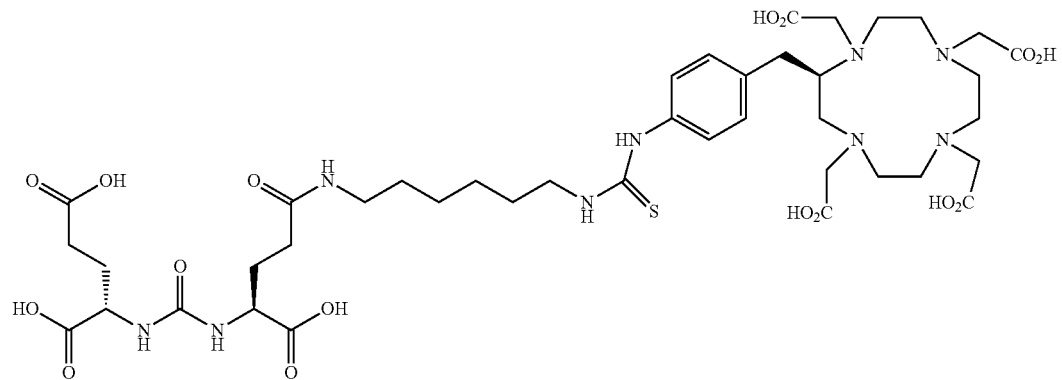
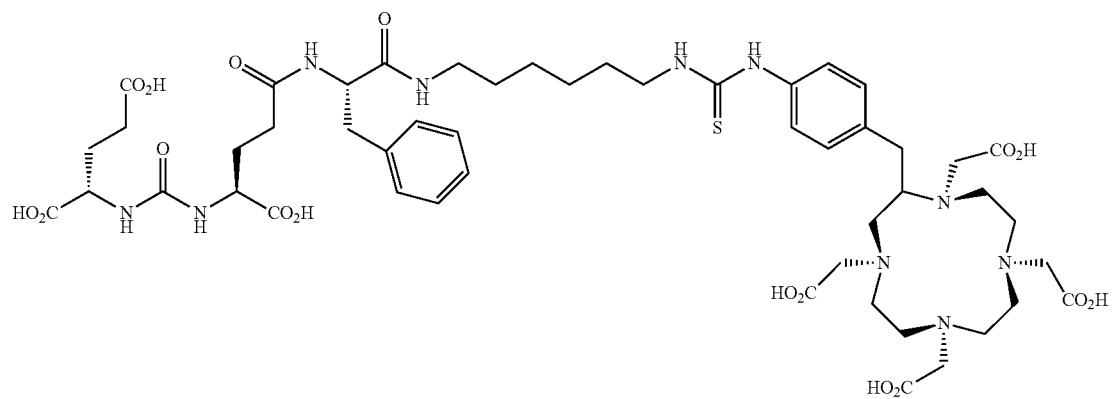

29
30
-continued
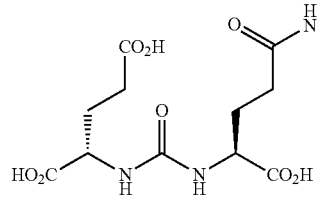
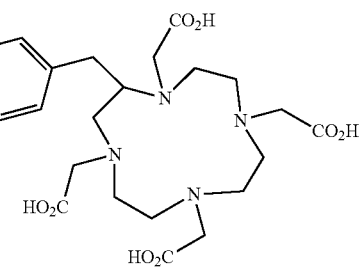
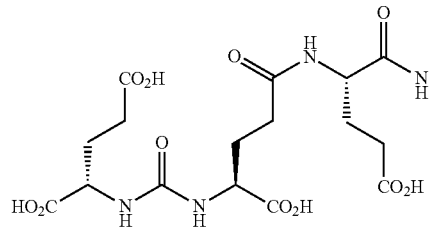
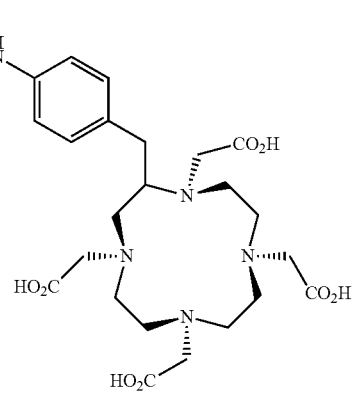
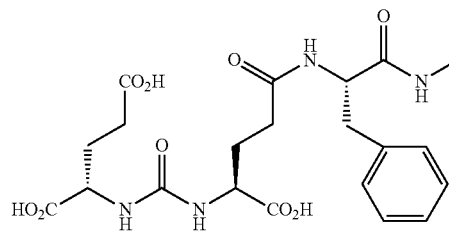
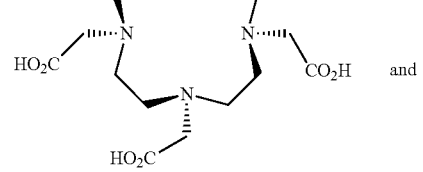 and
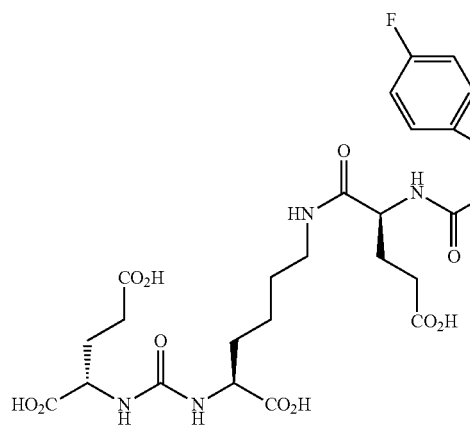
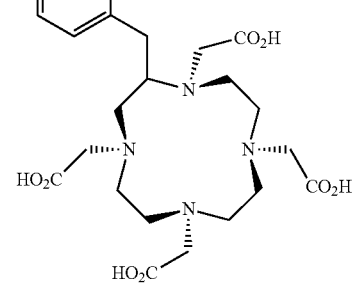

In one embodiment, L is —C(O)—(CHR¹)—(CH₂)ₚ—U— with R¹ being —H and subscript p being an integer between 1-10 both numbers inclusive. Group U according to this embodiment is —NR⁴R⁵ with either substituent R⁴ or R⁵ being hydrogen and the other substituent being a —C(S)NH-bezyl-group. Exemplary of such a linker is

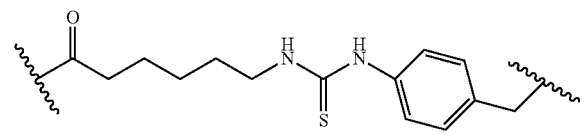

where p is 4. For certain Formula II compounds [>—W]ₖ is a —(CH₂)ₚ—U group with k being 2. In the first instance, U is a —(CH₂)ₚ—C(O)R group with R being —OH and p being 1. In the second instance U is an aryl group, for example an optionally substituted benzyl group.

An illustrative Formula II compound that comports with the above definition is illustrated below:

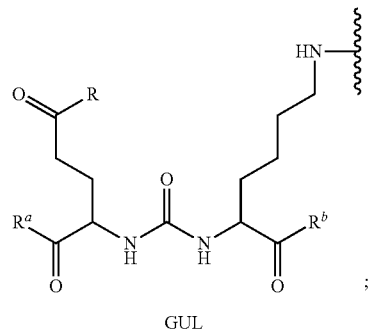

GUL

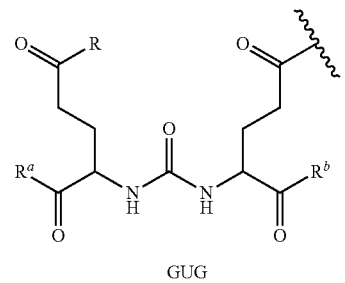

GUG

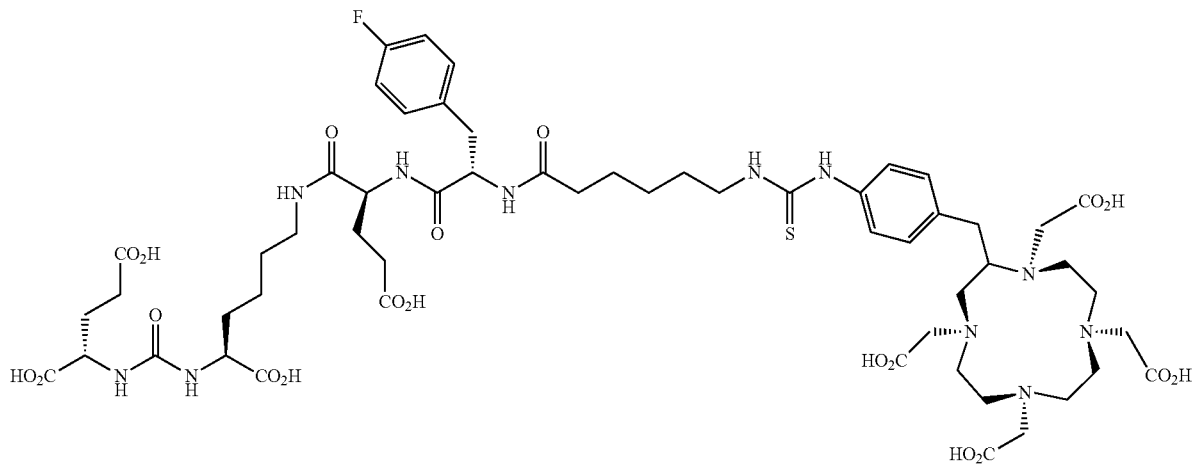

While the structures of Formula II compounds above do not illustrate pharmaceutically acceptable salts and/or solvates of the inventive compounds, it is within the scope of the present invention to encompass pharmaceutically acceptable salt forms and/or solvates. In some embodiments, the chelator group, for example, the DOTA group is not complexed with a radionuclide. In one embodiment, therefore, when DOTA is un-complexed the carboxylic acid groups of the DOTA group can be in the form of a free acid, or in the form of a salt. The free carboxylic acid groups can also be esterified to obtain the prodrug form of Formula I compounds. Suitable ester prodrugs include various alkyl esters, including saturated and unsaturated $C_8$ to $C_{18}$ fatty acids.

The inventive compounds are glutamate-urea-lysine (GUL-) or glutamate-urea-glutamate (GUG) analogs in which a chelator group is conjugated to the GUL- or GUG-moiety via a linker.

As further discussed below, the length and chemical nature of the linker group is believed to influence the binding avidity of Formula II compounds to the target tissue. Thus, Formula II compounds include without limitation linker groups having one or more carboxylic acid groups, methylene carboxylic acid (acetyl) groups, substituted or unsubstituted aryl groups (e.g., benzyl or naphthyl groups), hydroxyl, or amino groups pendant to the linker.

Depending on whether the Formula II compounds are to be used as radio imaging agents or radio pharmaceuticals, different radionuclides may be complexed to the compounds. Illustrative of suitable radionuclides are those selected from the group consisting of $^{111}$In, $^{90}$Y, $^{68}$Ga, $^{64}$Cu $^{153}$Gd, $^{155}$Gd, $^{157}$Gd, Fe and $^{177}$Lu. Illustrative compounds of Formula II include, but are not limited to those shown in Table 2.

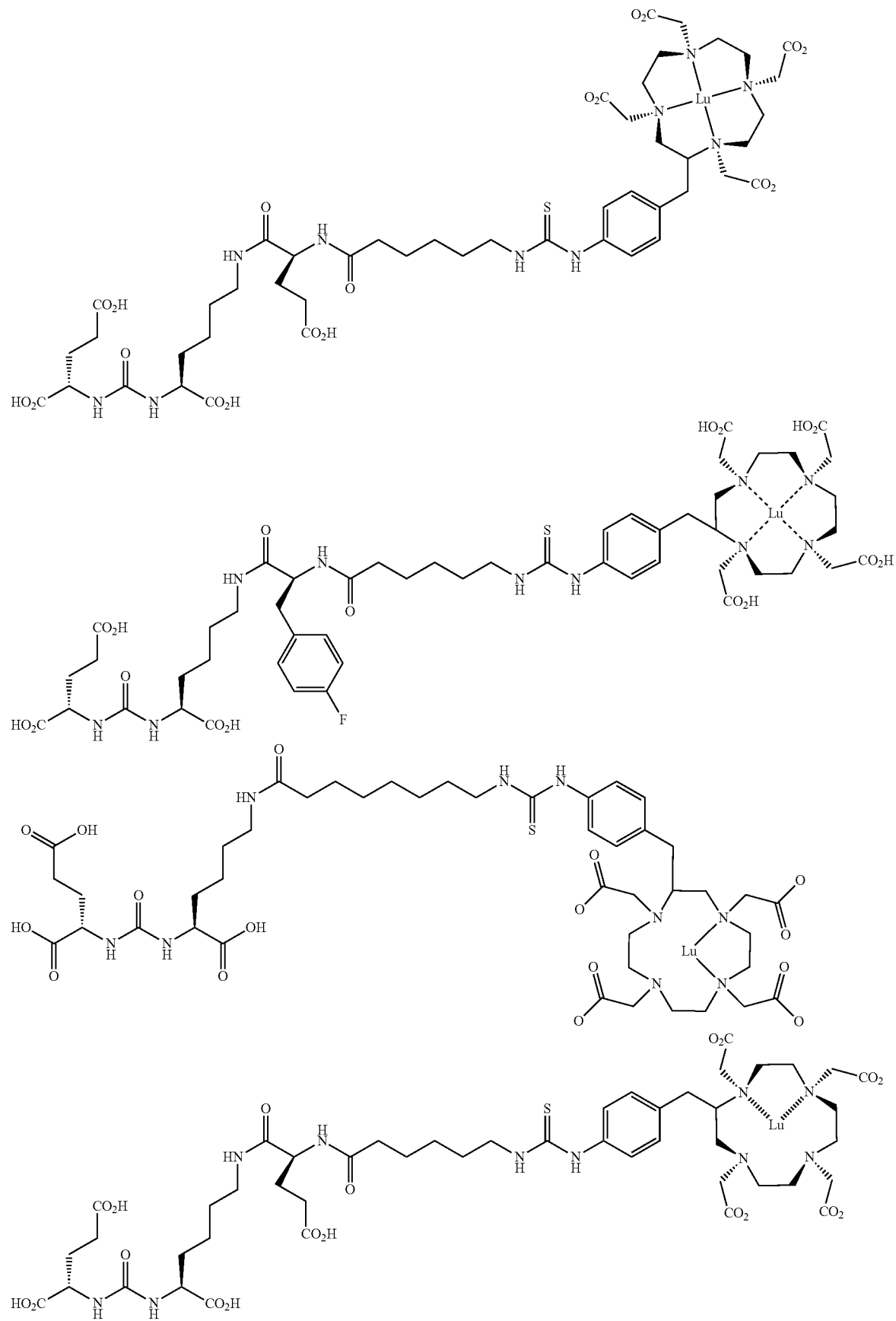

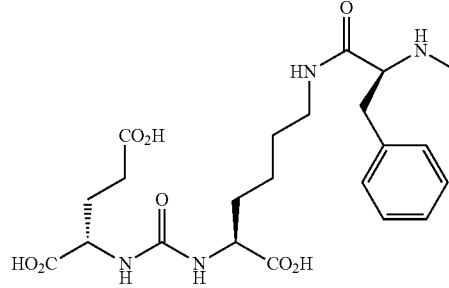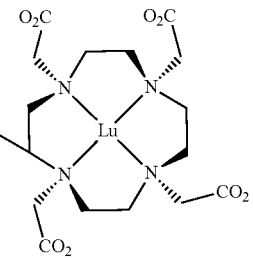
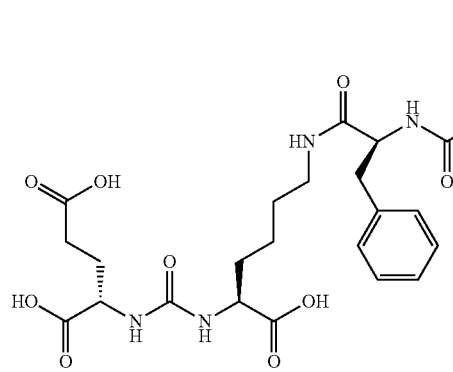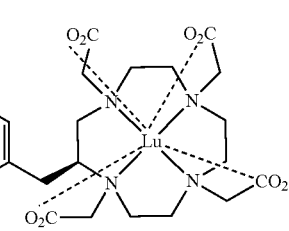
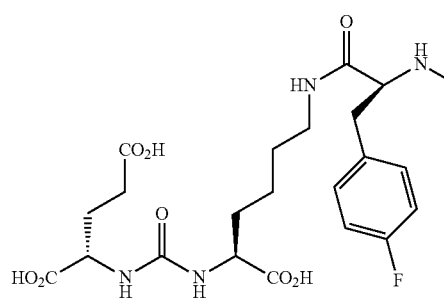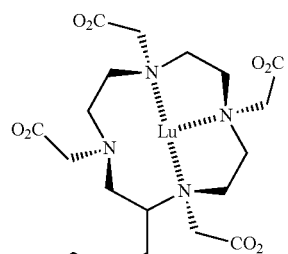

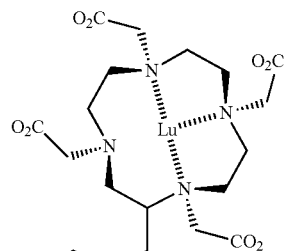
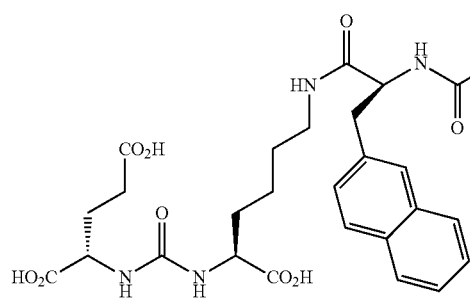
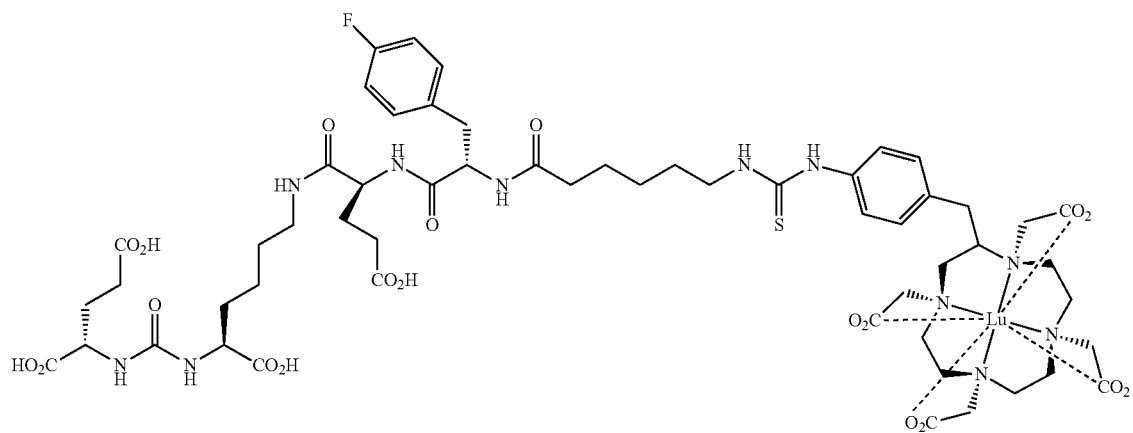
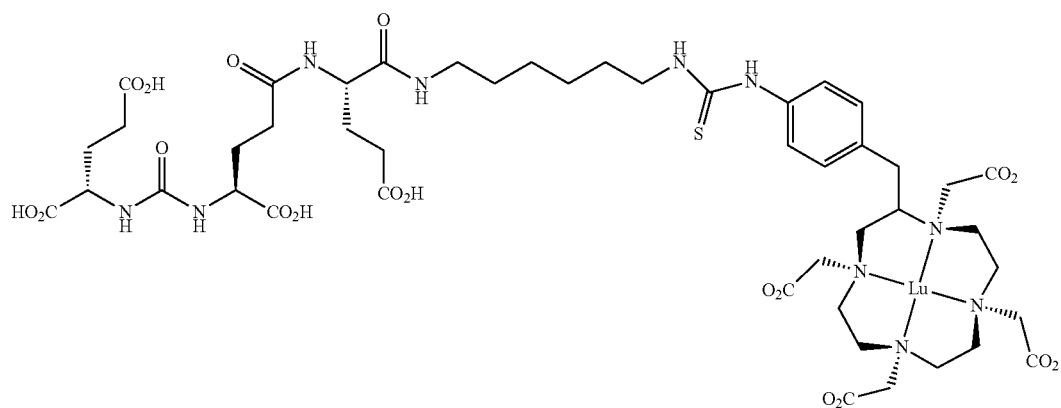

-continued
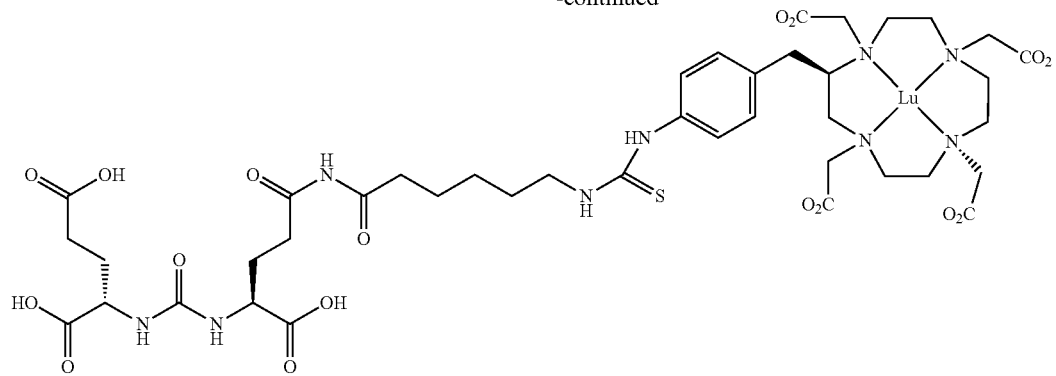
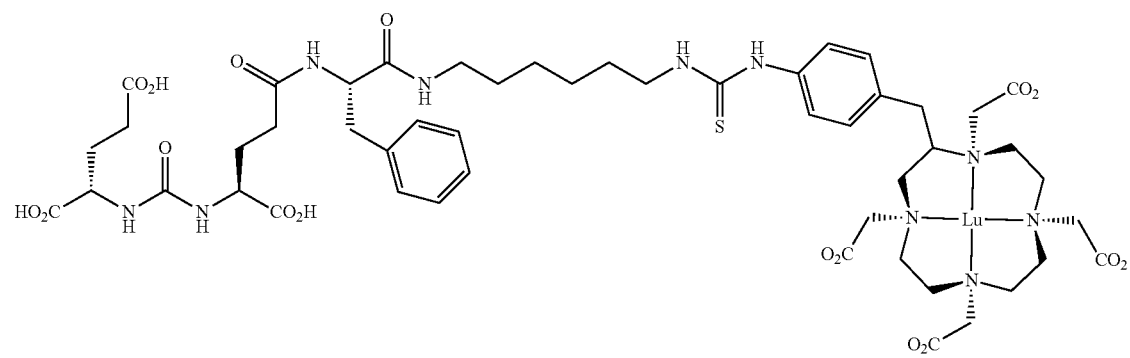
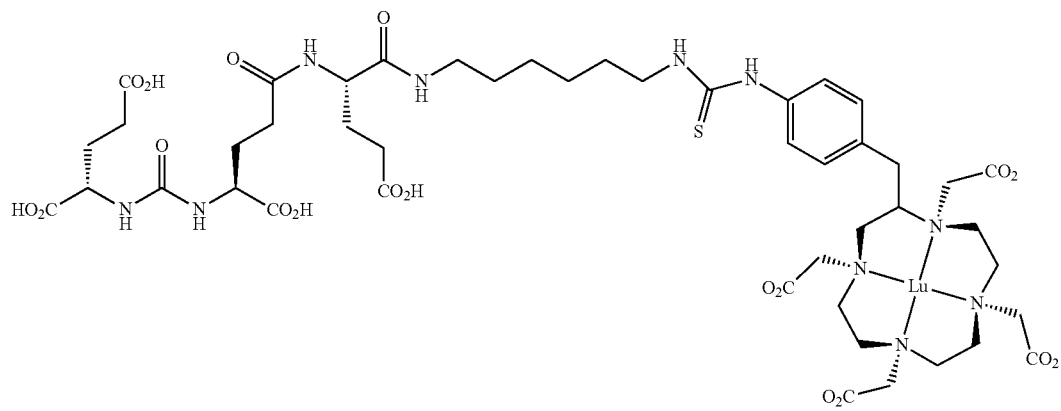
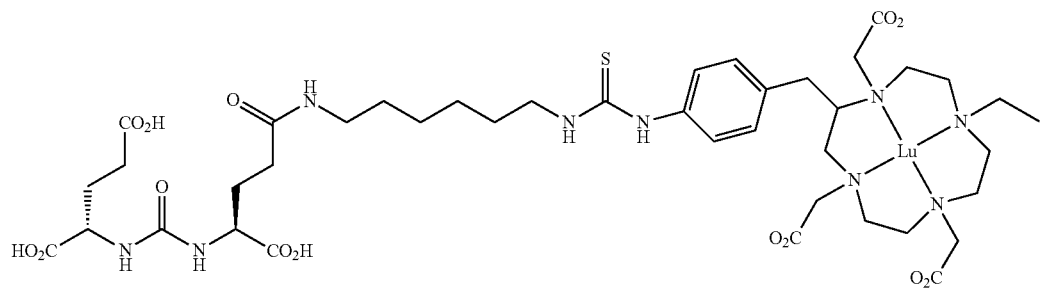

-continued
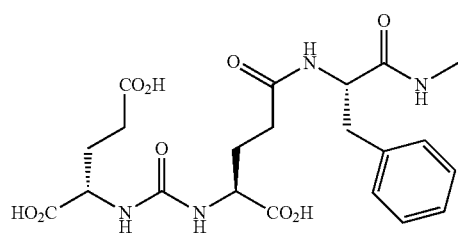
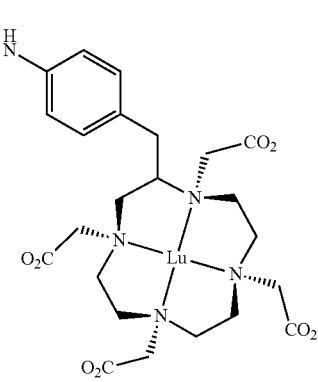
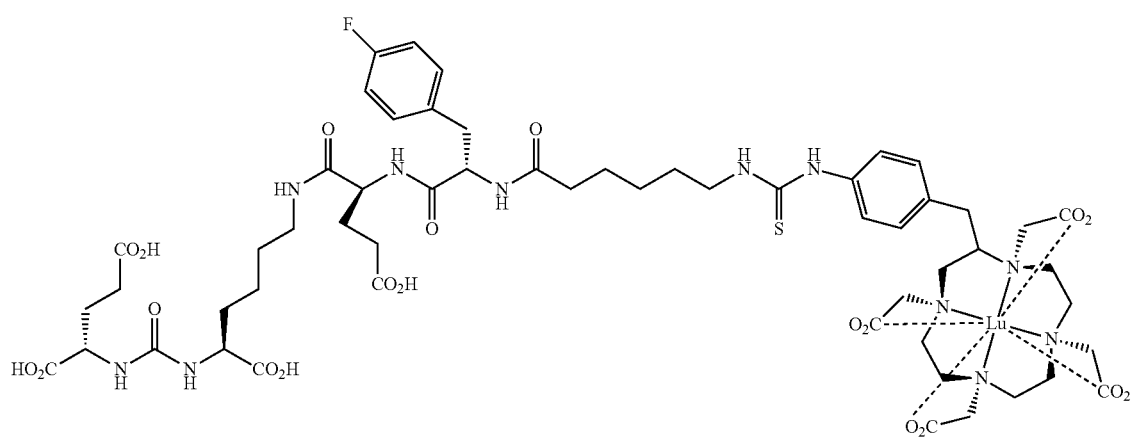
FIGS. 1A and 1B illustrate results of a bio-distribution study in LNCap xenograft mice of a GUG-DOTA-$^{177}$Lu complex (compound (A)) and a GUL-DOTA-$^{177}$Lu complex (compound (B)) according to Formula II.
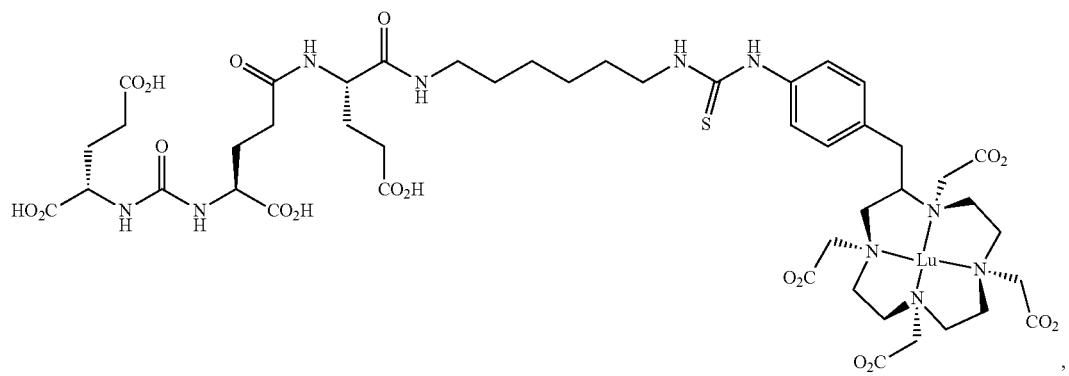
(A)

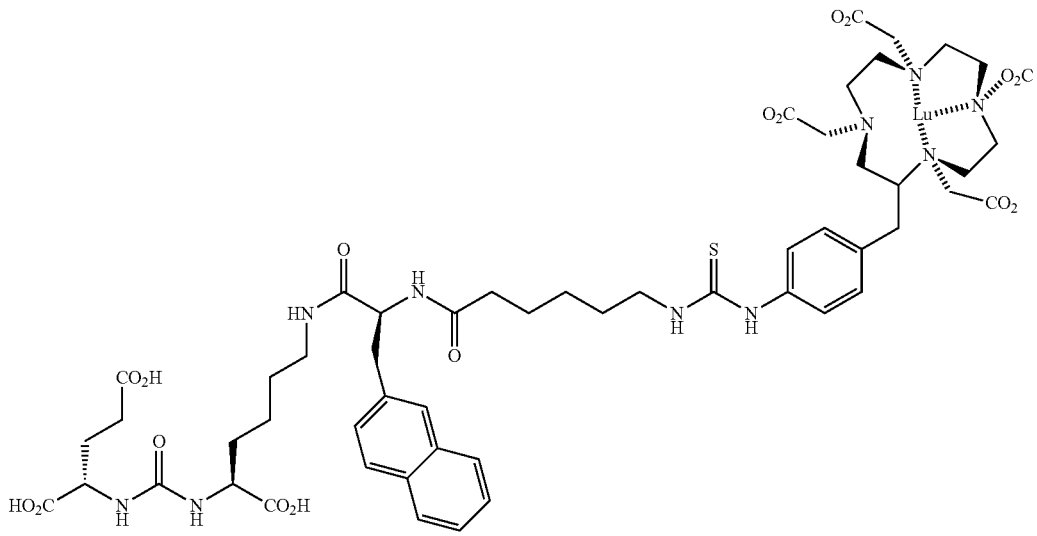

(B)

As illustrated by the bar graphs, both compounds (A) and (B) concentrate to a greater extent in the kidneys than LNCap tumor cells at 4 hours post administration. However, at 24 hours and 96 hours post administration, the concentration is greater in LNCap tumor cells than kidney for both compounds. In fact, there was a significant reduction in the concentration of both compounds in kidney at these later time intervals. These results suggest that while the compound does accumulate in kidney soon after administration to LNCap tumor cell bearing mice, the accumulated compound is rapidly cleared from the body post administration. In contrast, the inventive compounds accumulate within tumor cells with only a slight decrease in intratumoral concentration observed after 96 hours. Taken together, these results illustrate the greater affinity of radionuclide complexes of Formula II compounds to selectively target and bind to LNCap tumor cells.

The compounds of Formula I or Formula II were screened in a human prostate cancer cell binding assay using PSMA positive (+), LnCap cells. The results of this screening demonstrated to us whether the compounds exhibited specific binding to PSMA (+) cells. Compounds that exhibited specific binding to PSMA (+) cells where further evaluated in a competitive binding assay against the known inhibitor of PSMA, N—[N—[(S)-1,3-dicarboxypropyl]carbamoyl]-S-3-iodo-L-tyrosine (DCIT), and $IC_{50}$ values were calculated.

Briefly, LNCaP and PC3 human prostate cancer cells were obtained from American Type Culture Collection, Rockville, Md. LNCaP cells were maintained in RPMI-1640 medium supplemented with 10% fetal bovine serum (FBS). Binding of the radiolabeled compound and competition with cold derivatives to LNCaP cells was performed according to published methods. Cells were plated in 12-well plates at approximately $4 \times 10^5$ cells/well and incubated for 48 hours in a humidified incubator at 37° C./5% carbon dioxide prior to addition of compound. Solutions of the Formula I or Formula II compounds were prepared and diluted in serum-free cell culture medium containing 0.5% bovine serum albumin (BSA) in combination with 3 nM $^{123}I$ DCIT (known inhibitor). Total binding was determined by incubating $^{123}I$-DCIT without test compound. Plates were incubated at room temperature for 1 hour. Cells were removed from the plates and transferred to eppendorff tubes. Samples were microcentrifuged for 15 seconds at 10K×g. The medium was aspirated and the pellet was washed twice by dispersal in fresh assay medium followed by microcentrifugation. Cell binding of $^{123}I$ DCIT was determined by counting the cell pellet in an automated gamma counter. Nonspecific binding was determined as the counts associated with the cells after incubating with 2 uM nonradiolabeled compound or 2-phosphonomethyl-pentanedioic acid (PMPA). Table 3 illustrates the $IC_{50}$ values of representative Formula II complexes.

TABLE 1

| Complex | $IC_{50}$ (nM) |
| --- | --- |
| Lu-MIP-1512 | 23 |
| Lu-MIP-1523 | 54 |
| Lu-MIP-1530 | 21 |
| Lu-MIP-1531 | 28 |
| Lu-MIP-1545 | 10 |
| Lu-MIP-1546 | 15 |
| Lu-MIP-1550 | 22 |
| Lu-MIP-1548 | 77 |
| Lu-MIP-1526 | 78 |
| Lu-MIP-1519 | 12 |

Compounds of Formula I compounds or their pharmaceutically acceptable salts, esters or solvates include:

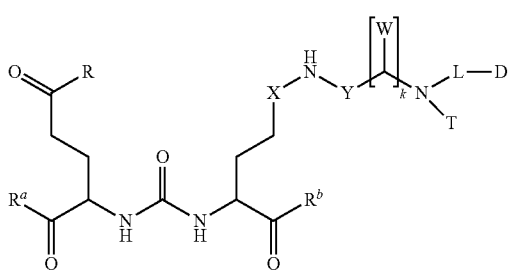

I

Formula I compounds also comprise a first terminal group and a second terminal group that are connected using a linker or spacer. The first terminal group is a tripeptide comprising a glutamic-urea-lysine (GUL), or glutamic-urea-glutamic (GUG) moiety (see above), while the second terminal group comprises a chelator such as moieties selected from

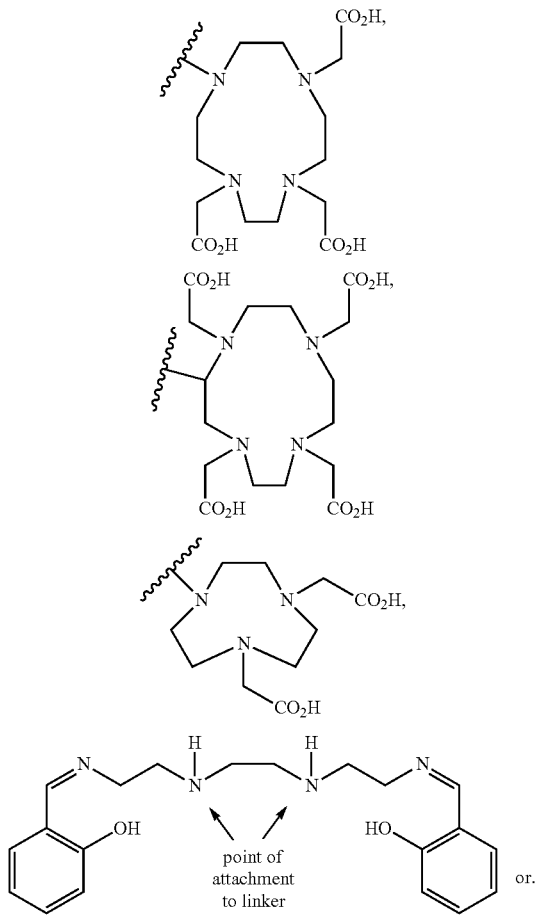

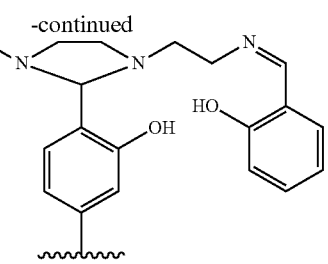

which may be complexed with a radionuclide.

For Formula I compounds each of X an Y in the first terminal group are each independently $(CHR^1)_m$ or C(O). When X is $(CHR^1)_m$ Formula I compounds are GUL analogs when m is 2. However, subscript "m" can be any integer from 0 to 6, both values inclusive. Alternatively, when X is a carbonyl (—C(O)—), inventive compounds comprising the GUG recognition motif are obtained.

Formula I and II compounds are candidate therapeutics for the treatment and diagnosis of prostate cancer. The present inventors have found that the chemical nature and size of the linker effects affinity of Formula I and Formula II compounds for PSMA expressed on the surface of prostate cancer cells. The present inventors used structure-activity relationships to study (a) the correlation between linker size PSMA affinity, and (b) to study the contribution of polar groups within the linker region on PSMA binding.

For instance, the inventors found that using a aminohexanoic acid spacer to link the GUL recognition element to a DOTA-indium chelate gave a Formula I compound (1) that showed moderate activity for PSMA ($IC_{50}$=175 nM).

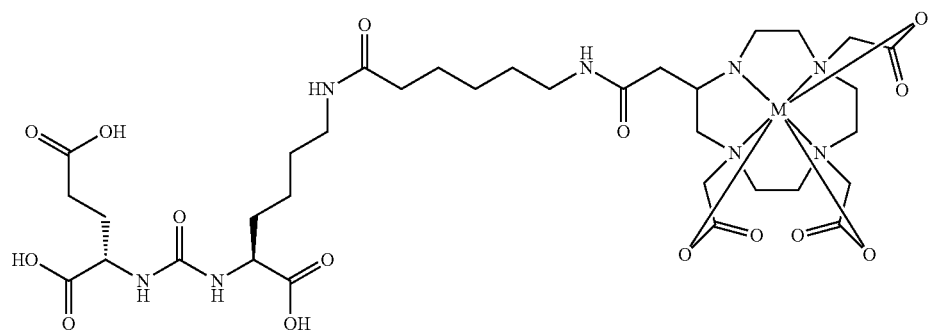

1 (M = H, free ligand)
M-(1) (M = In, Ga, Lu, Y)

The introduction of an amino group, such as the use of lysine to link the recognition motifs to DOTA, further reduced binding affinity. Thus, substitution of the aminohexanoic acid spacer with a lysine spacer gave compound (2) which showed increased aqueous solubility but a two-fold reduced the affinity for PSMA ($IC_{50}$=443 nM).

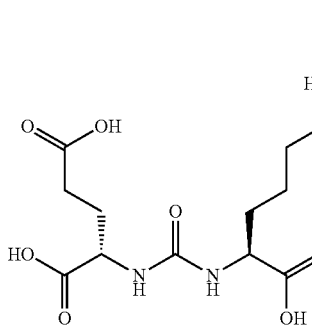
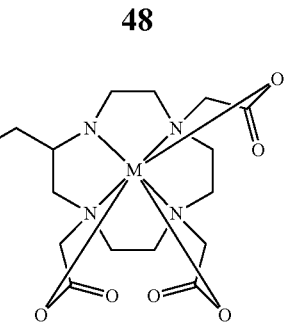

2 (M = H, free ligand)
M-(2) (M = In, Ga, Lu, Y)

It was further observed that the non-metalated Formula I compounds showed increased affinity for PSMA when compared to the corresponding radinuclide complexes.

Without ascribing to any particular theory, the inventors believe that the increased affinity of non-metalated Formula I compounds stems from their reduced steric bulk and/or due to the additional binding interactions that occur between PSMA and the free carboxylic acid groups of DOTA. In the radionuclide complex, however, the carboxyl groups of DOTA are involved in metal coordination interactions and are not available, therefore, for interaction with appropriately positioned amino acid residues of PSMA.

To evaluate the percent contribution (a) or (b) to the overall decrease in binding affinity of Formula I compounds to PSMA the present inventors tested the affinity of the technetium-99m complex with DOTA for PSMA and compared the $IC_{50}$ value for this complex to the corresponding non-metallated compound. Decreased binding affinity was observed for the Technitium-99m complex which suggests that the observed loss in binding affinity for the metal complex species, most likely is due to a loss in binding interactions that occur between PSMA and the free carboxylic acid groups of DOTA.

According to one aspect,

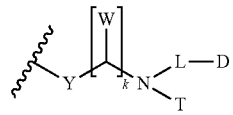

represents the linker moiety of Formula I compounds and its metal complex with radionuclides. Thus, in one embodiment substituent W can be a H, or —$(CH_2)_p$—U. When W is —$(CH_2)_p$—U, p is an integer having value of 0, 1, 2, 3, 4, 5, or 6, U is hydroxyl (—OH), —OR, —COOR or $NR^4R^5$. For instance, W can be —$CH_2$—COOH (acetate) group or an alkyl ester of acetate, for example, a methyl ester, ethyl ester, propyl ester, or t-butyl ester.

For Formula I compounds, L can be is —C(O)—$(C_1-C_{10})$ alkylene, —[C(O)—$CH(Z)_d$]—NH]$_j$$NR^2R^3$, —C(O)—$(CHR^1)$—$(CH_2)_p$—U—, —$(C_5-C_{14})$aryl-$(C_1-C_{10})$alkylene, $R^6$O-benzylene, —$(C_5-C_{14})$heteroaryl-$(C_1-C_{10})$alkylene, [C(O)—$CH(Z)_d$—NH]$_t$—C(O)—$(CHR^1)_m$—$(CH_2)_p$—U, or —C(O)—[$(CH_2)_p$—V]$_n$—$(CH_2)_q$—C(O)—U.

T is H, —$(C_1-C_{10})$alkylene, RC(O)—$(C_1-C_{10})$alkylene, $NR^2R^3$—$(C_1-C_{10})$alkylene, —$(C_5-C_{14})$heteroaryl-$(C_1-C_{10})$alkylene or —$(C_5-C_{14})$aryl-$(C_1-C_{10})$alkylene. V is —NH—, —$NR^2$— or —$NR^2R^3$, while Z is —$(CH_2)_p$—COOH or —$(CH_2)_p$—$NR^2R^3$. For Formula I compounds, groups R, $R^a$ and $R^b$ are each independently —H, —OH, —$(C_1-C_{10})$alkyl, —O$(C_1-C_{10})$alkyl, or $NHR^2$ and $R^1$ is hydrogen or —$NH_2$. Groups $R^2$, $R^3$, $R^4$ and $R^5$ are each independently H, a bond, $(C_1-C_{10})$alkylene, F, Cl, Br, I, C(O), C(S), —C(S)—NH-benzyl-, —C(O)—NH-benzyl-, —C(O)—$(C_1-C_{10})$alkylene, —$(CH_2)_p$—NH—C(O)—$(CH_2)_p$—, —$(CH_2$—$CH_2)_t$—NH—C(O)—$(CH_2)_p$—, —$(CH_2)_p$—COR, —$(CH_2)_p$—C(O) NH—C[$(CH_2)_p$—COR]$_3$, —C[$(CH_2)_p$—COR]$_3$, or —$(CH_2)_p$—$(C_5-C_{14})$heteroaryl.

For compounds according to Formula I, moreover, any aryl, heteroaryl, or cycloalkyl may be optionally substituted with 1, 2, or 3 substituent groups such as —$(C_1-C_{10})$alkyl, —$(C_1-C_{10})$haloalkyl, —$(C_1-C_{10})$ amino alkyl, —$(C_1-C_{10})$ hydroxyalkyl, —$(CH_2)_p$—C(O)—U and —$(C_3-C_8)$cycloalkyl.

In one embodiment, L is —$(C_5-C_{14})$aryl-$(C_1-C_{10})$alkylene and T is —$(C_5-C_{14})$heteroaryl-$(C_1-C_{10})$alkylene. In such embodiments L may be a substituted benzyl, for example, $R^6$O-benzylene where $R^6$ is defined as —O$(CH_2)_p$—$(C_5$-$C_{14})$heteroaryl-$(CH_2)_p$—U. Illustrative heteroaryls include without limitation imidazole, pyridine, 1,2,3-triazole, 1,2,4-triazole, oxazole, and oxadiazole groups. L, for instance, can be a moiety represented by the following chemical structure:

(L)

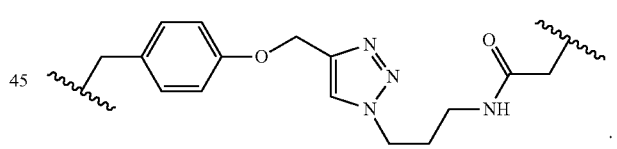

The heteroaryl moiety of substituent T can be the same as L, or different from L. In one embodiment T can be a chemical moiety represented by the following structure:

(T)

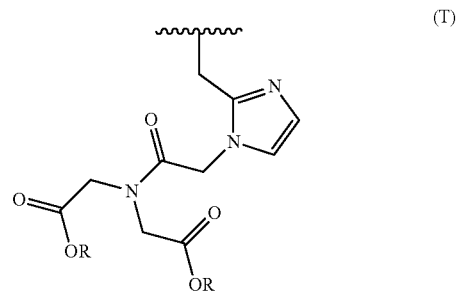

In one aspect, a compound of Formula I has the following structure:

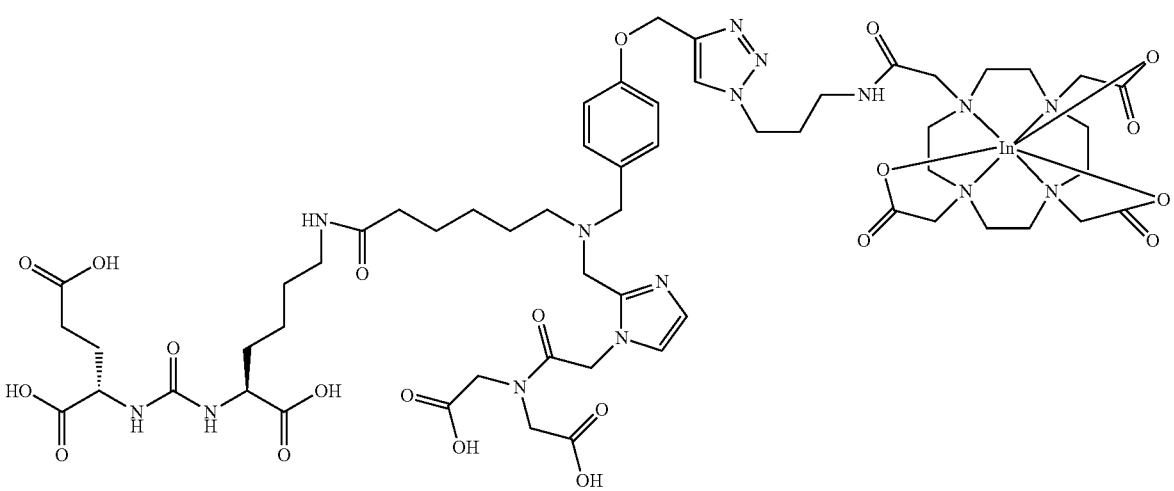

Compound 3 (IC$_{50}$=46 nM), which utilized a dicarboxy-imidazole functionalized linker binds to PSMA with an affinity that is almost a ten-fold greater than the affinity of compound 1 having a amino-hexanoic acid linker shown above.

Compounds in accordance with the present invention can also utilize ethylenediaminetetraacetic acid (EDTA) to link DOTA to the Glutamate-urea-Lysine (GUL) and Glutamate-urea-Glutamate (GUG) recognition sequences.

Additionally, each EDTA group provides two free carboxylic acids which are believed to increase renal clearance by improving aqueous solubility and thus, reducing overall exposure of Formula I compounds to the kidneys. The EDTA linker is proposed to promote tighter binding of inventive compounds to PSMA. Without being bound by theory, it is believed that the two free carboxylic acid groups on each EDTA in the linker can participate in binding interactions with amino acid residues of PSMA, thus, promoting the binding of Formula I compounds to this protein. Accordingly, radionuclide complexes of Formula I compounds having an EDTA linker will exhibit enhanced binding to PSMA, especially when compared to compounds having an alkyl linker or a lysine linker.

To further explore whether the position of polar groups along the linker chain affect binding of Formula I compounds to PSMA, compounds were synthesized in which the linker is an appropriately functionalized alkyl chain having a defined number of methylene groups is tethered to a GUL or GUG motif at one end and one or more EDTA moieties are attached to the opposite end of the alkyl chain.

According to this embodiment, substituent W is hydrogen; subscript k is an integer from 0 to 6, for example, 4, 5, or 6, substituent T is H and L is —C(O)—[(CH$_2$)$_g$—V]$_n$—(CH$_2$)$_q$—C(O)—U. In one embodiment, V is —NR$^2$R$^3$, R$^2$ is H and R$^3$ is R—C(O)—(C$_1$-C$_{10}$)alkylene, for example, a methylene-COOH (—CH$_2$COOH) group, or an ethylene-COOH group. U is NR$^4$R$^5$ with substituent R$^4$, in one embodiment, being H and R$^5$ being a —(CH$_2$)$_p$—NH—C(O)—(CH$_2$)$_p$— group. An illustrative Formula I compound that comports with the above definition is illustrated below:

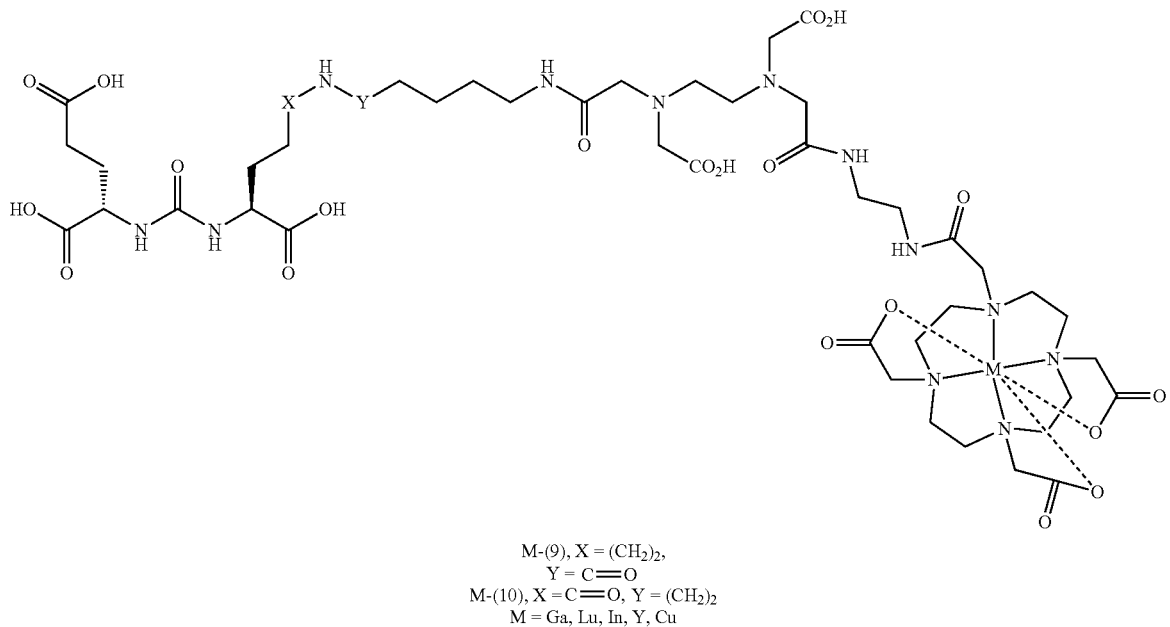

M-(9), X = (CH$_2$)$_2$,
Y = C=O
M-(10), X = C=O, Y = (CH$_2$)$_2$
M = Ga, Lu, In, Y, Cu

The above class of Formula I compounds were high affinity ligands of PSMA. Structure-activity studies indicated that the affinity of Formula I compounds for PSMA increased for those compounds having carboxylic acid groups pendant to the linker. These observations support a role for poly-aspartate or poly-glutamate based linkers. In one embodiment of the invention, therefore, a series of compounds having varying number of aspartate units, or glutamate units in the linker between the PSMA recognition sequence GUL or GUG and the chelator DOTA were synthesized. Typically, a series of four, five or six aspartatic acid residues or glutamic acid residues are used as the linker However, the number of aspartic acid or glutamic acid residues in the linker can be from two residues to about 15 residues. A linker including a mixture of aspartic acid and glutamic acid residues, such as alternating aspartic acid and glutamic acid residues may also be used in the compounds.

Binding studies for compounds of Formula I having aspartic acid, glutamic acid, or a mixture of aspartic acid and glutamic acid residues in the linker showed that the free carboxylic acid groups of these residues may be participating in binding interaction with the PSMA protein which results in enhanced affinity of these compounds for PSMA. Additionally, poly-glutamic acid is a substrate for PSMA. Thus, Formula I compounds having a poly-glutamic acid linker may show increased binding affinity for PSMA. A Formula I compound having a poly-aspartic acid or poly-glutamic acid linker is the following compound having five aspartate or glutamate residues between the GUL o GUG PSMA recognition moiety and the radionuclide chelator DOTA.

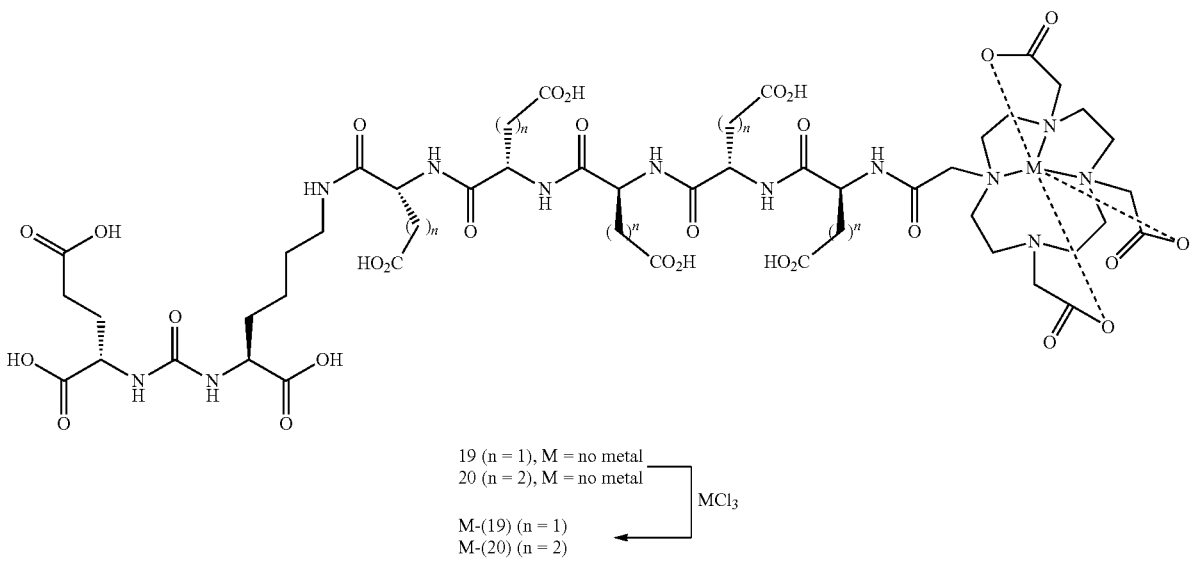

In yet another embodiment, Formula I compounds are provided having a hybrid linker made up of an aminohexanoic acid group and a lysine dipeptide structurally depicted below.

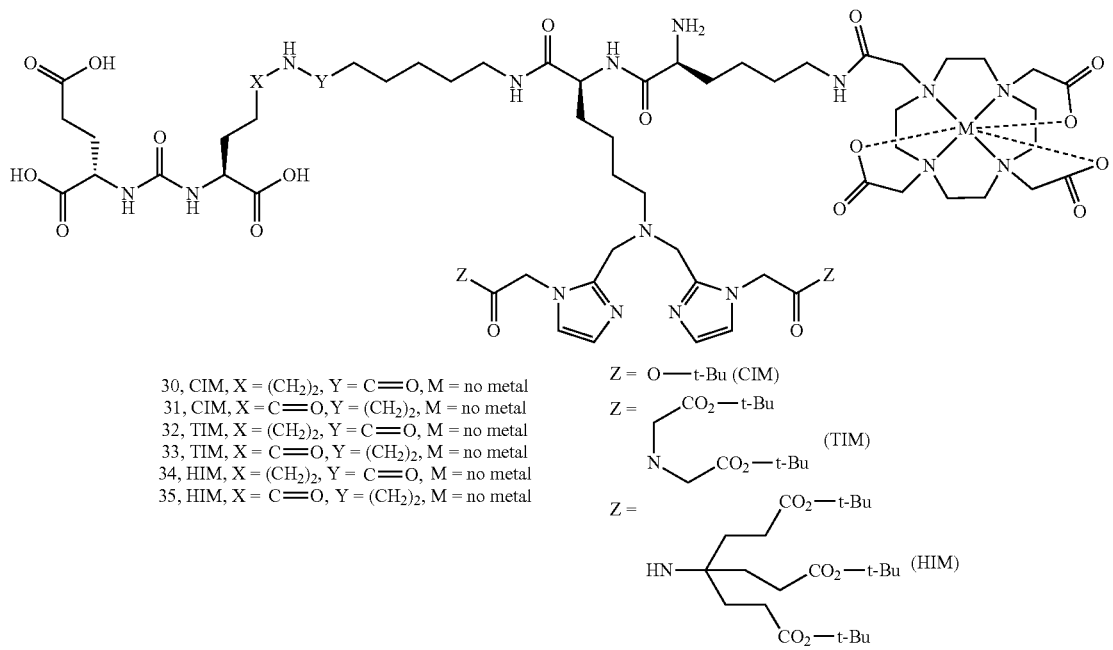

As shown above, the ϵ-amino of the side chains of the two lysine groups are being used to tether the chelators SAAC II and DOTA. Based on the results from experiments aimed at improving the pharmacokinetic profile of small molecules directed to PSMA and other protein targets implicated in disease processes, the inventors have observed that the conjugation of SAAC II improved tissue distribution, renal clearance, most likely by improving the aqueous solubility of the small molecule therapeutics and imaging agents.

Again, without being bound by theory, it is believed that the introduction of CIM, TIM, or HIM SAAC II chelators in the linker between GUL or GUG PSMA recognition moities and DOTA should improve the pharmacokinetics of tissue distribution and renal clearance of Formula I compounds. Indeed, inventive compounds and their metal complex having a SAAC II group in the linker showed improved aqueous solubility, good renal clearance and exhibited a strong affinity for PSMA protein on prostate cancer cells.

Examples of chemical groups having one or more carboxylic acid moieties and that are suitable for incorporation into the linker region of Formula I compounds include without limitation, those illustrated below, such as CIM, TIM and HIM.

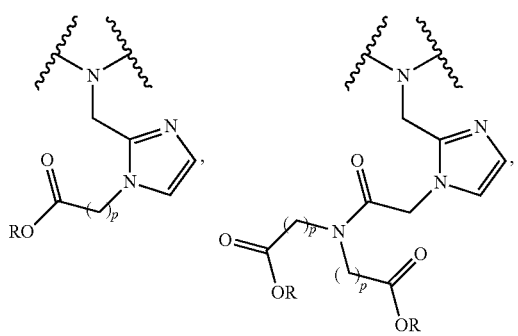

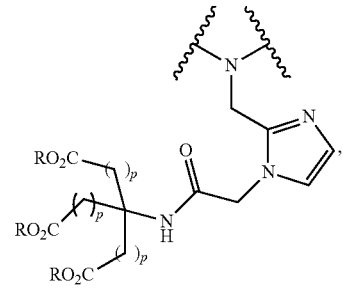

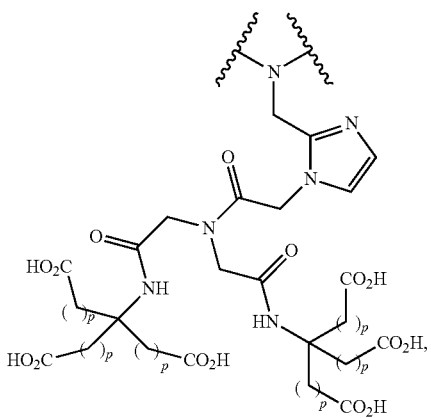

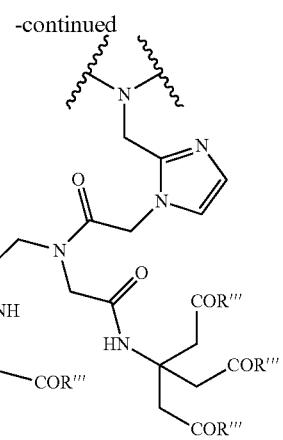

When the chemical group providing the one or more carboxylic acid moiety in the linker is

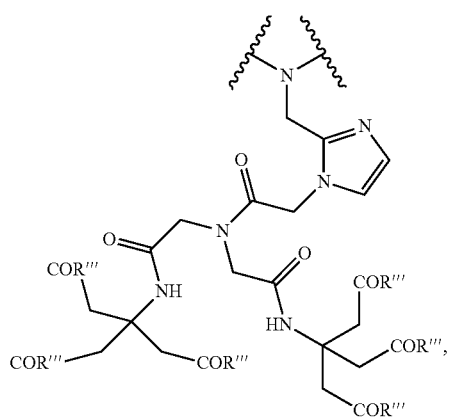

each R''' can independently be

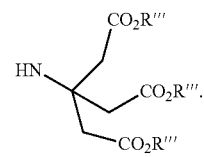

The linker includes at least two carboxyl moieties, each having a formula —$CO_2J$. Each J, moreover, may be the same or different and is independently selected from H, ($C_1$-$C_6$) lower alkyl, and a pharmaceutically acceptable organic or inorganic salt.

For formula I compounds, D is a chelator group, for instance a group such as DOTA, NOTA $H_3$[(sal)$_3$ TETA], $H_2$[(sal)$_2$ TETA], $H_3$[(5-MeOsal)$_3$ TAME], DTPA, or HBED which are graphically represented by the following structures

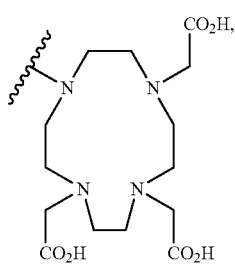

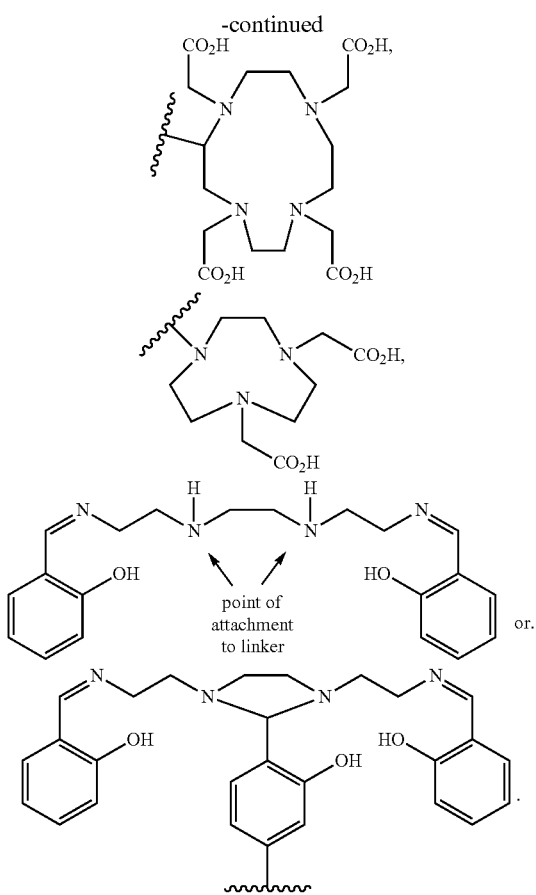

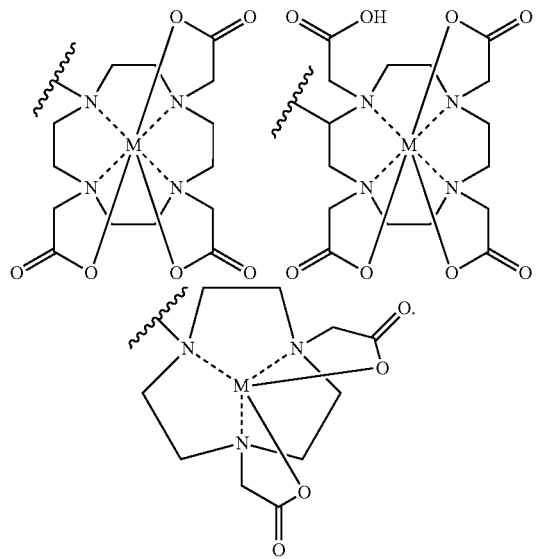

In some embodiments D is a non-metallated 2,2',2'',2'''-(1,4,7,10-tetraazacyclododecane-1,4,7,10-tetrayl)tetraacetic acid (DOTA), while in other embodiments D can be a non-metallated chelator based on the structures exemplified above.

In other embodiments, D can be a metal complex formed by the complexation of a radionuclide with DOTA, NOTA or HBED as shown below.

Alternatively, D is a metal complex formed by the complexation of an appropriate radionuclide with the following metal chelators.

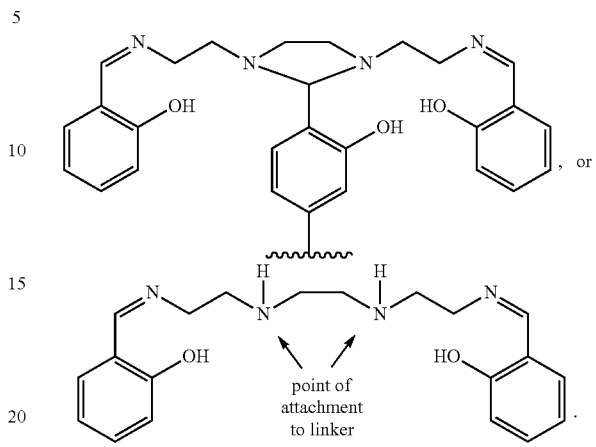

For inventive compounds according to Formula I, subscripts d, j, k, m, n, p and t are each independently an integer between 0 and 6. For instance, subscripts d, j, k, m, n, p and t can each independently be 0, 1, 2, 3, 4, 5, or 6. When aryl, heteroaryl, or cycloalkyl substituent groups are present in a Formula I compound, these substituent groups can optionally be substituted by 1, 2, or 3 other substituent groups selected from the group consisting of —($C_1$-$C_{10}$)alkyl, —($C_1$-$C_{10}$) haloalkyl, —($C_1$-$C_{10}$) aminoalkyl, —($C_1$-$C_{10}$)hydroxyalkyl, —($C_1$-$C_{10}$)alkylene-C(O)—U, and —($C_3$-$C_8$)cycloalkyl.

Depending on whether the inventive Formula I compounds are to be used as radio imaging agents or radio pharmaceuticals different radionuclides are complexed to DOTA. Illustrative radionuclides include, for example $^{111}$In, $^{90}$Y, $^{68}$Ga, $^{177}$Lu, $^{99m}$Tc, $^{64}$Cu, $^{153}$Gd, $^{155}$Gd, $^{157}$Gd, and Fe. According to one aspect of this invention, the radionuclide is $^{111}$In, $^{90}$Y, $^{68}$Ga, $^{64}$Cu, $^{153}$Gd, $^{155}$Gd, $^{157}$Gd, Fe, or $^{177}$Lu.

Based on the above described SAR study, Formula I compounds having one or more carboxyl groups, or a SAAC II group in the linker between a GUL or GUG recognition moiety and the chelator DOTA are potent inhibitors of PSMA, with $IC_{50}$ values in the low nanomolar range. These compounds also showed improved aqueous solubility which accounts, at least in part, for their improved tissue distribution and renal clearance.

FIG. 2 illustrates results of a bio-distribution study in LNCap xenograft mice using a GUL-DOTA-$^{111}$In complex and a hydrophobic aminohexanoic acid linker. As illustrated by the bar graph, the test compound MIP-1450 concentrates in the kidney, that is, shows high kidney uptake and poor uptake in LNCap tumor cells. The inventors hypothesize that the low biodistribution of MIP-1450 LNCap tumor cells may be due to this compounds low affinity for PSMA expressed on the surface of LNCap cells. As stated above, it was unexpectedly that presence of carboxylic acid groups in the linker region increased affinity of Formula I compounds for PSMA. This increase in binding affinity is due, at least in part to additional cooperative binding interactions of the free carboxylic acid groups with amino acid residues of PSMA. Illustrative of Formula I compound-radionuclide complexes that have one or more carboxylic acid groups as part of the linker group include without limitation the following compounds:

57 58
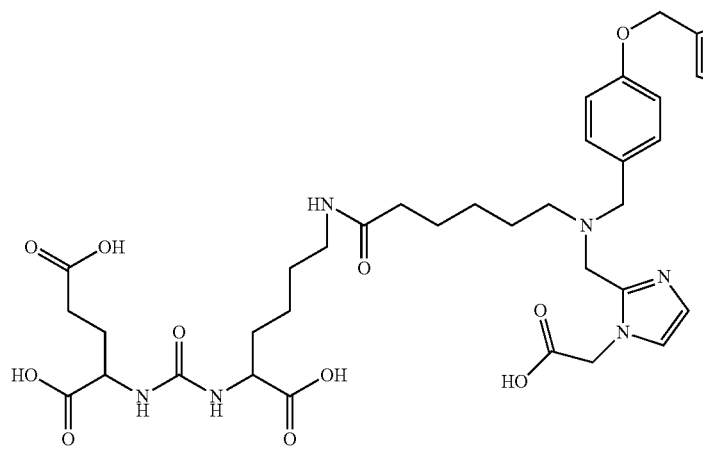 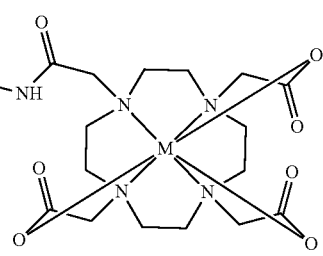
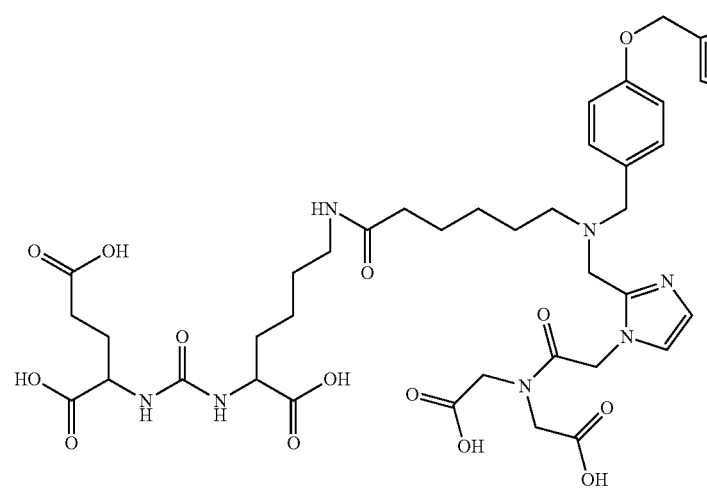 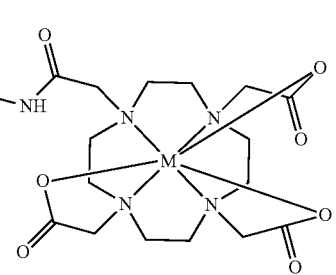
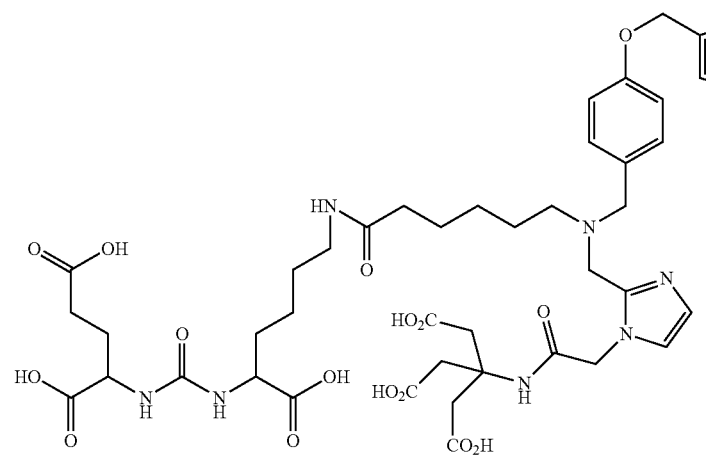 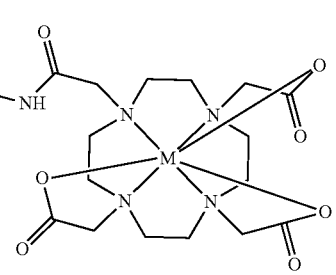

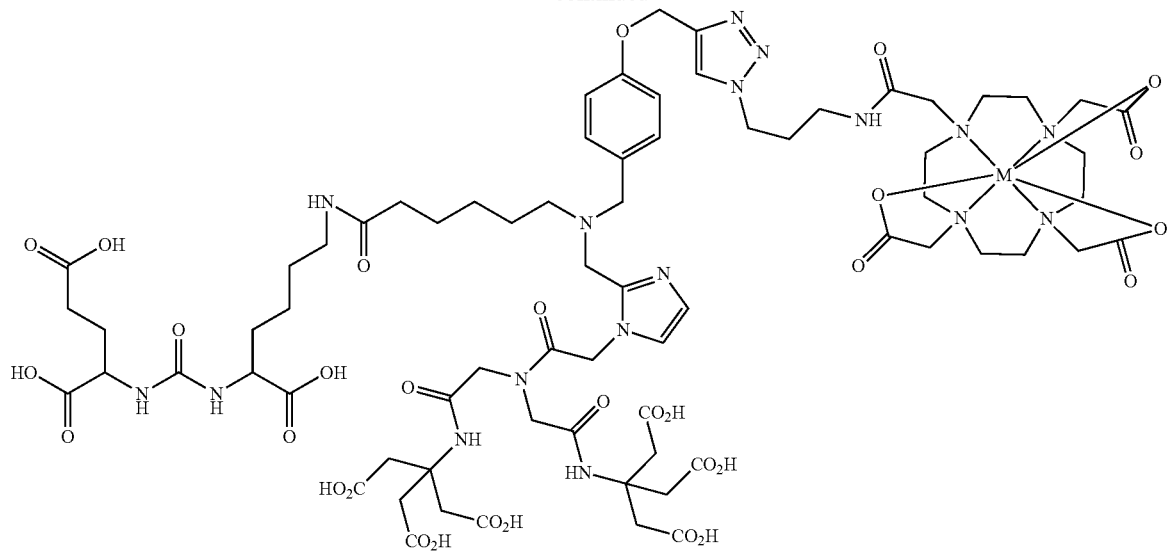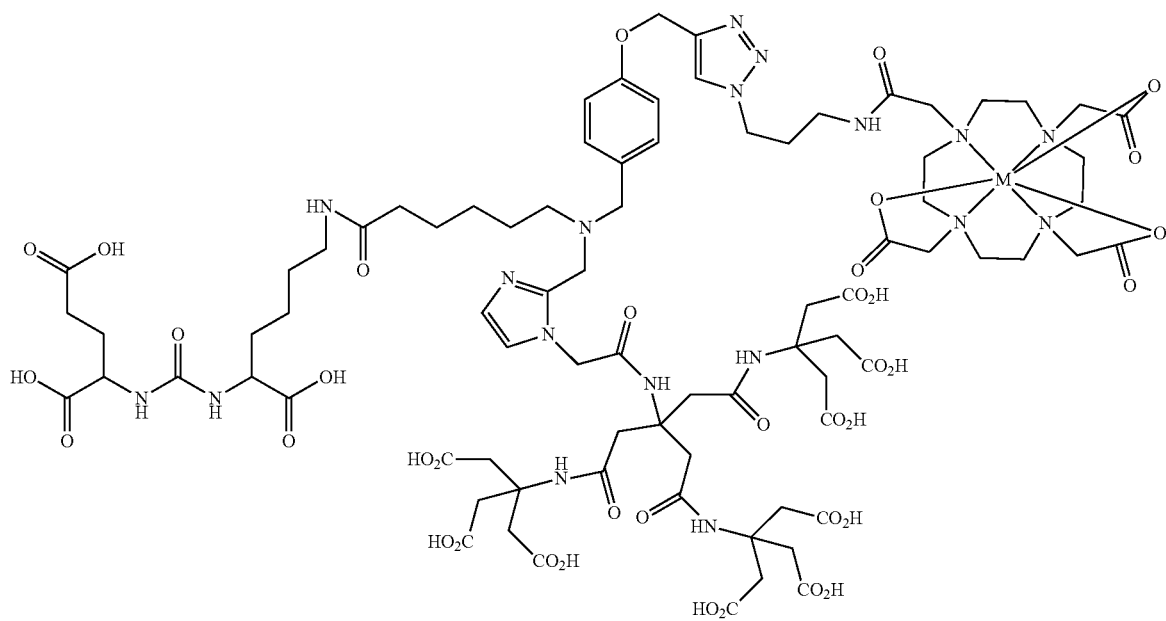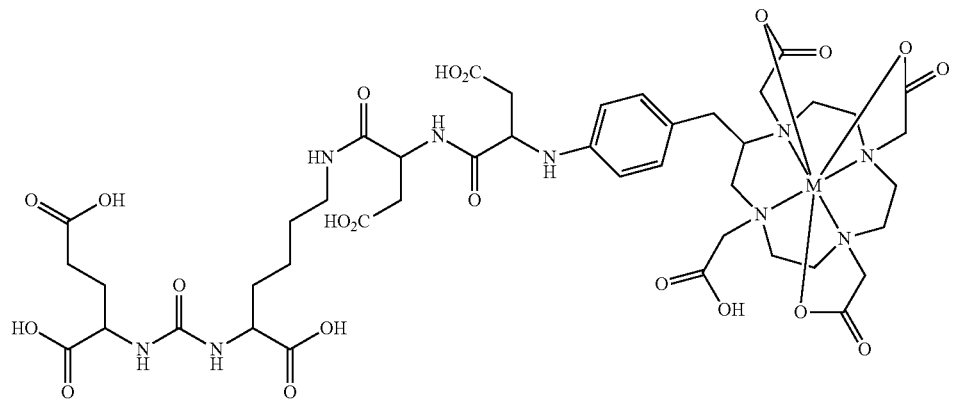

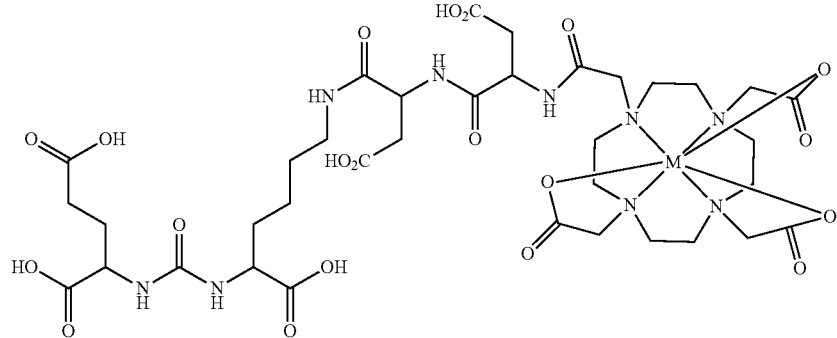
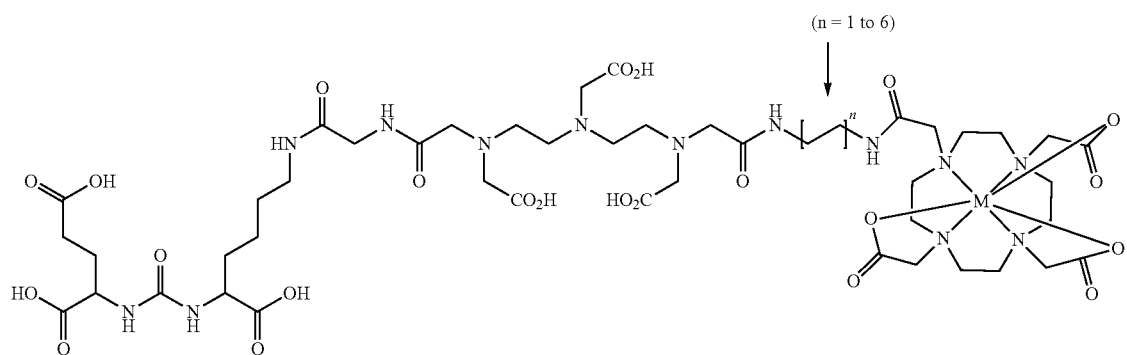
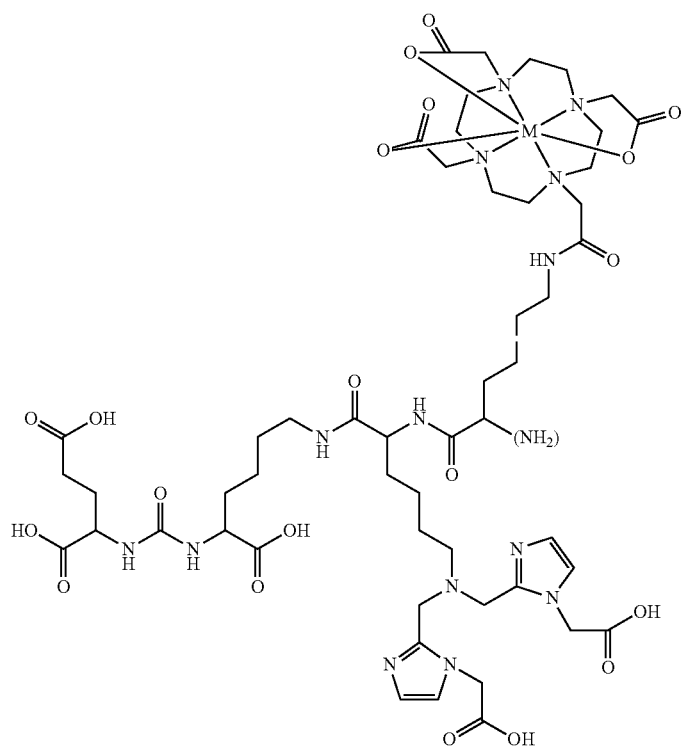

-continued
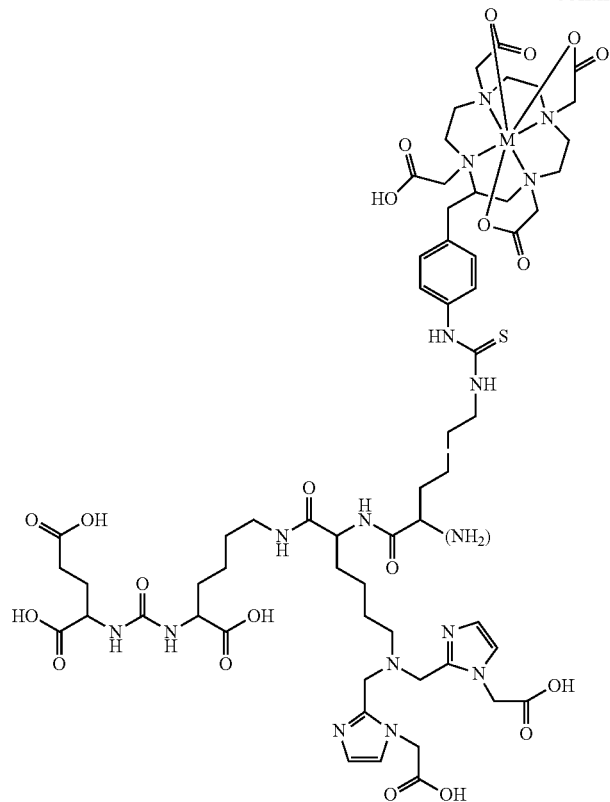
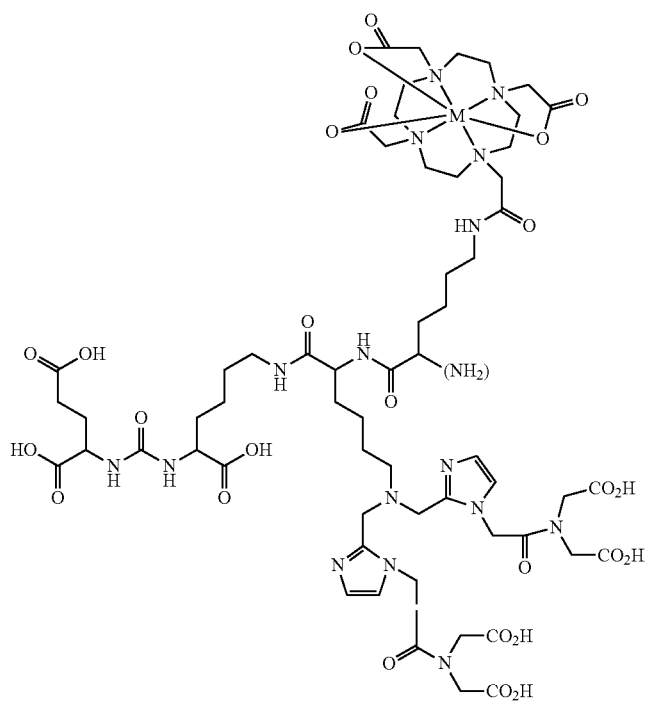

-continued
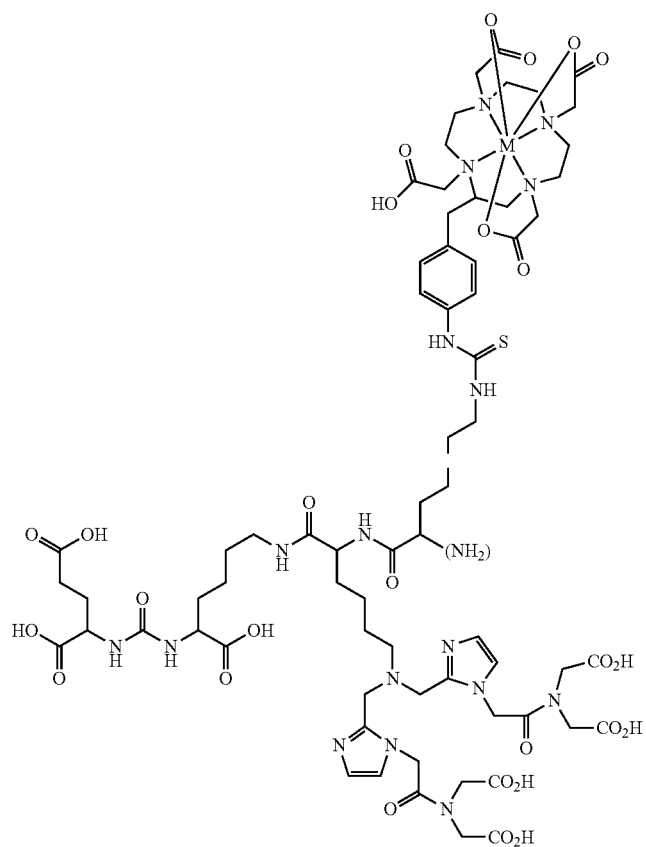
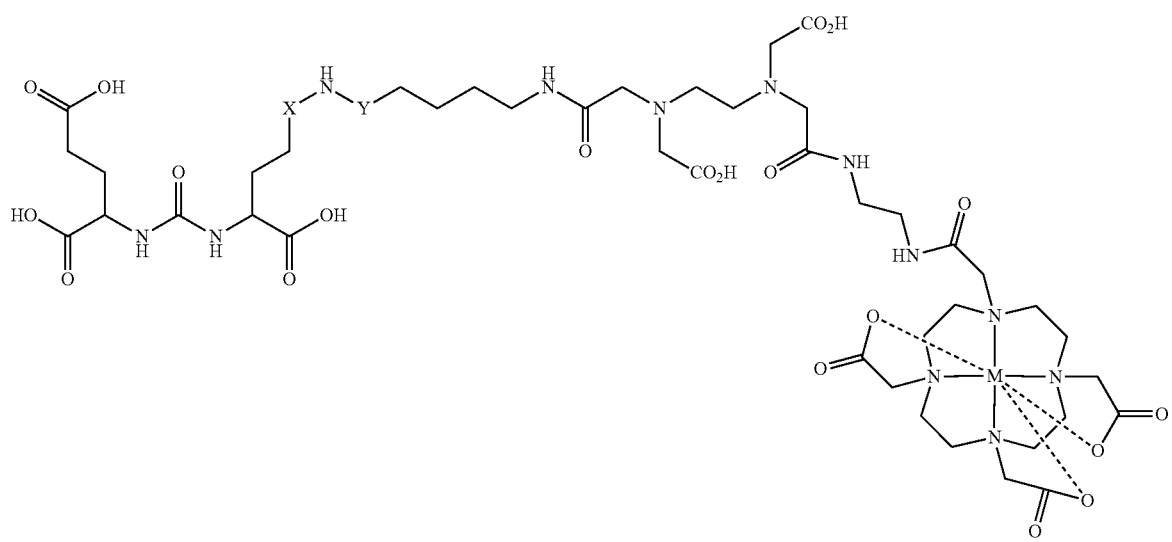
X = (CH$_2$)$_2$, Y = C=O
X = C=O, Y = (CH$_2$)$_2$

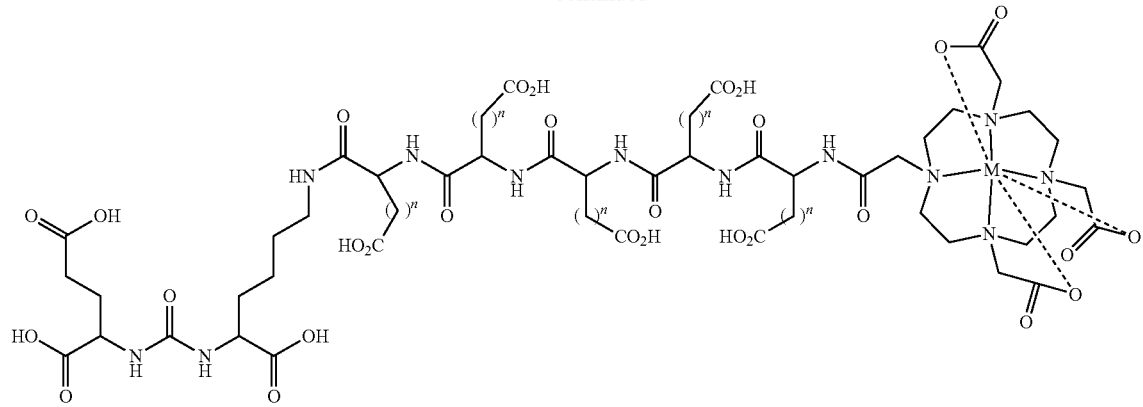
n is independantly 1, 2, or 3 in each instance
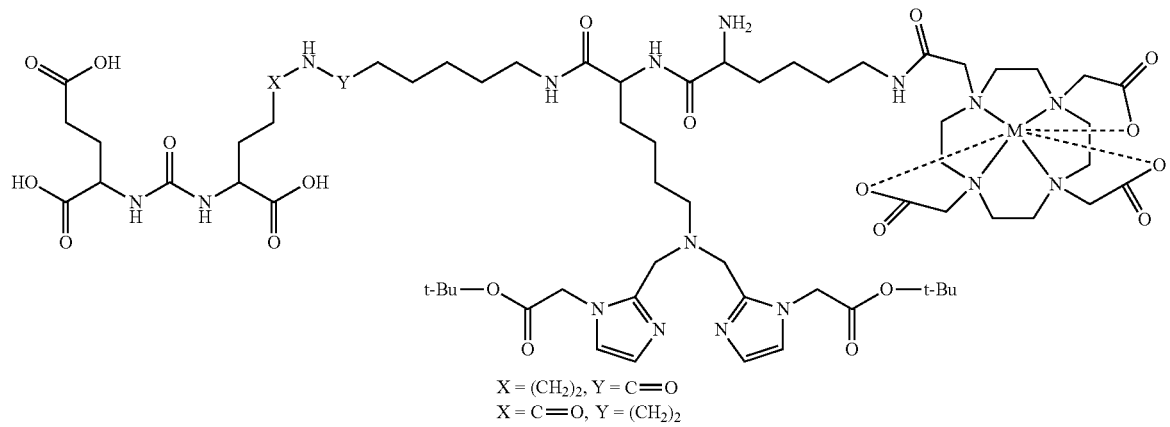
X = (CH$_2$)$_2$, Y = C═O
X = C═O, Y = (CH$_2$)$_2$
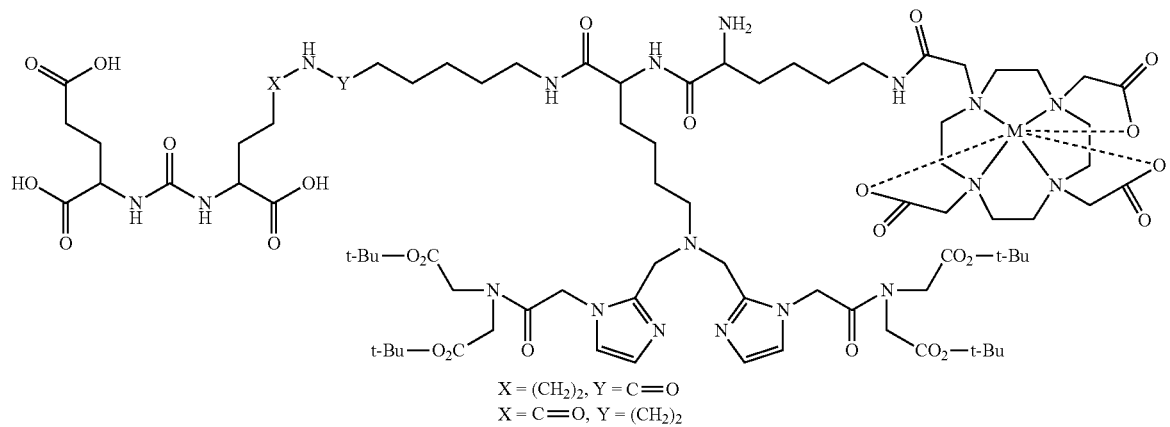
X = (CH$_2$)$_2$, Y = C═O
X = C═O, Y = (CH$_2$)$_2$ -continued

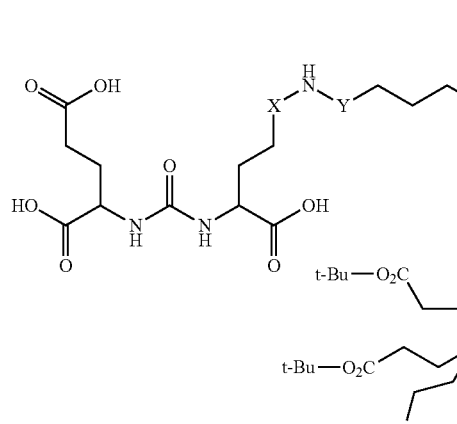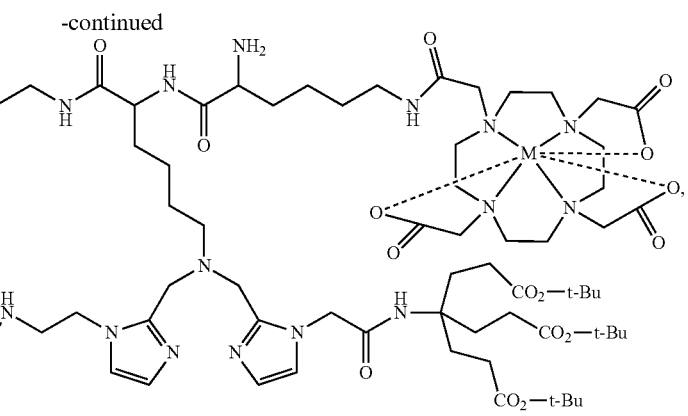

X = (CH$_2$)$_2$, Y = C═O
X = C═O, Y = (CH$_2$)$_2$

While the structures above do not illustrate pharmaceutically acceptable salts and/or solvates of the inventive compounds; it is within the scope of the present invention to encompass pharmaceutically acceptable salt forms and/or solvates. In some embodiments, the chelator group, for example, the DOTA group is not complexed with a radionuclide. In one embodiment, therefore, when DOTA is un-complexed the carboxylic acid groups of the DOTA group can be in the form of a free acid, or in the form of a salt. The free carboxylic acid groups can also be esterified to obtain the prodrug form of Formula I compounds. Suitable ester prodrugs include various alkyl esters, including saturated and unsaturated $C_8$ to $C_{18}$ fatty acids.

When Formula I and Formula II compounds and their radionuclide complexes have one or more chiral centers the present invention encompasses both enantiomers, as well as all of the diasteroisomers. Moreover, both L and D-forms of the natural amino acids can be used for synthesizing the Formula I and Formula II compounds. That is, the present invention encompasses stereoisomers, tautomers, and prodrugs of Formula I and Formula II compounds.

Pharmaceutical Formulations

As noted above, complexes of the compounds according Formula I or Formula II may contain one or more radionuclides which are suitable for use as radio-imaging agents or as therapeutics for the treatment of rapidly proliferating cells, for example, PSMA expressing prostate cancer cells. Accordingly, in one embodiment, a pharmaceutical composition is provided including a complex that includes a metal and a compound of Formula I or Formula II, a salt, solvate, stereoisomer, or tautomer thereof, and a pharmaceutically acceptable carrier.

In general, metal complexes of a Formula I or a Formula II compound or pharmaceutical compositions thereof, may be administered orally, or via a parenteral route, usually by injection. Parenteral routes include, but are not limited to, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion. In some embodiments, the compound, or pharmaceutical composition thereof, is administered orally. Such compositions may take the form of tablets, pills, capsules, semisolids, powders, solutions, suspensions, elixirs, aerosols, or any other appropriate compositions.

According to another aspect, a pharmaceutical composition is provided, which is suitable for in vivo imaging and radiotherapy. Suitable pharmaceutical compositions may contain a radio imaging agent, or a radiotherapeutic agent that has a radionuclide either as an element, i.e. radioactive iodine, or a radioactive metal chelate complex of the compound of Formula I or Formula II in an amount sufficient for imaging, together with a pharmaceutically acceptable radiological vehicle. The radiological vehicle should be suitable for injection or aspiration, such as human serum albumin; aqueous buffer solutions, e.g., tris(hydromethyl)aminomethane (and its salts), phosphate, citrate, bicarbonate, etc; sterile water; physiological saline; and balanced ionic solutions containing chloride and or dicarbonate salts or normal blood plasma cations such as calcium, potassium, sodium, and magnesium.

The concentration of the imaging agent or the therapeutic agent in the radiological vehicle should be sufficient to provide satisfactory imaging. For example, when using an aqueous solution, the dosage is about 1.0 to 50 millicuries. The actual dose administered to a patient for imaging or therapeutic purposes, however, is determined by the physician administering treatment. The imaging agent or therapeutic agent should be administered so as to remain in the patient for about 1 to 24 hours, although both longer and shorter time periods are acceptable. Therefore, convenient ampoules containing 1 to 10 mL of aqueous solution may be prepared.

Imaging may be carried out in the normal manner, for example by injecting a sufficient amount of the imaging composition to provide adequate imaging and then scanning with a suitable machine, such as a gamma camera. In certain embodiments, a method of imaging a region in a patient includes the steps of: (i) administering to a patient a diagnostically effective amount of a compound complexed with a radionuclide; exposing a region of the patient to radiation; and (ii) obtaining an image of the region of the patient. In certain embodiments of the region imaged is the head or thorax. In other embodiments, the compounds and complexes of Formula I or Formula II target the PSMA protein.

Thus, in some embodiments, a method of imaging tissue such as spleen tissue, kidney tissue, or PSMA-expressing tumor tissue is provided including contacting the tissue with a complex synthesized by contacting a radioactive metal and a Formula I compound or a Formula II compound.

In another aspect, a method of imaging a region in a patient is provided including administering to a patient a diagnostically effective amount or a therapeutically effective amount of a Formula I compound complexed to a metal or a Formula II compound, complexed to a metal, or a pharmaceutically acceptable salt or solvate, and obtaining an image of the region of the patient. The metal used to form the complex is a radionuclide selected from $^{111}$In, $^{90}$Y, $^{68}$Ga, $^{64}$Cu $^{153}$Gd, $^{155}$Gd, $^{157}$Gd, Fe or $^{177}$Lu.

The amount of a Formula I or Formula II compound, or a formulation comprising a complex of a metal and a compound according to Formula I or Formula II, or its salt, solvate, stereoisomer, or tautomer that is administered to a patient depends on several physiological factors that are routinely used by the physician, including the nature of imaging to be carried out, tissue to be targeted for imaging or therapy and the body weight and medical history of the patient to be imaged or treated using a radiopharmaceutical.

Accordingly in another aspect, the invention provides a method for treating a patient by administering to a patient a therapeutically effective amount of a Formula I or Formula II compound complexed to a radionuclide, or a pharmaceutically acceptable salt or solvate of the complex to treat a patient suffering from a cell proliferative disease or disorder. Specifically, the cell proliferative disease or disorder to be treated using a radiopharmaceutical in accordance with this invention is a cancer, for example, prostate cancer.

The present invention, thus generally described, will be understood more readily by reference to the following examples, which are provided by way of illustration and are not intended to be limiting of the present invention.

EXAMPLES

General Synthetic Methods

General procedure for complexation of the compounds with a metal. As exemplified herein, indium is used as the metal. However, as is to be understood, similar synthetic procedures may be followed using the other metals described herein to complex with the compounds of Formula I. Therefore, while indium may be specifically shown in various examples, it is understood to include Y, Ga, Lu complexes as well. Additionally, it is to be understood that various isotopes of these elements may be complexed, for example, $^{111}$In, $^{90}$Y, $^{68}$Ga, $^{64}$Cu, or $^{177}$Lu.

General Experimental Conditions for the Formation of the Indium Complexes

The indium complexes of the compounds of Formula I are conveniently isolated from the reactions that involve contacting commercially available InCl$_3$ with a compound of Formula I. Briefly, the appropriate compound of Formula I ($10^{-6}$ M–$10^{-4}$ M) in an equal volume mixture of 1:1 acetonitrile and phosphate buffer is contacted with InCl$_3$ in a sealed vial. The reaction mixture is allowed to heat at 100° C. for 30 to 45 minutes. Upon cooling, the reaction was analyzed for purity via reverse-phase high pressure liquid chromatography (RP-HPLC) and if required can be purified using RP-HPLC or C18 Sep Pak columns. The average yield of the desired product following purification is in the range from about 20% to about 99%. The radiochemical purity (RCP), after HPLC purification, however, was consistently ≥95%. for the "carrier free" products. Although initial results demonstrated radiolabeling at concentrations as low as $10^{-6}$ M, the radiochemical yield (RCY) at this concentration of reagents was ≤80%. To achieve a RCY greater than 95%, the reaction temperature and concentration of reagents in the reaction mixture were increased to $10^{-4}$ M.

A similar synthetic strategy was used to incorporate other radionuclides. Moreover, the introduction of a radionuclide can be prior to deprotection of a Formula I compound, or after deprotecting a Formula I compound.

Synthesis of Exemplary Formula I & Formula II Compounds

A. Scheme 1 is an illustration of the general synthetic route for GUL-HEX-EDTA-DOTA and GUG-HEX-EDTA-DOTA analogs.

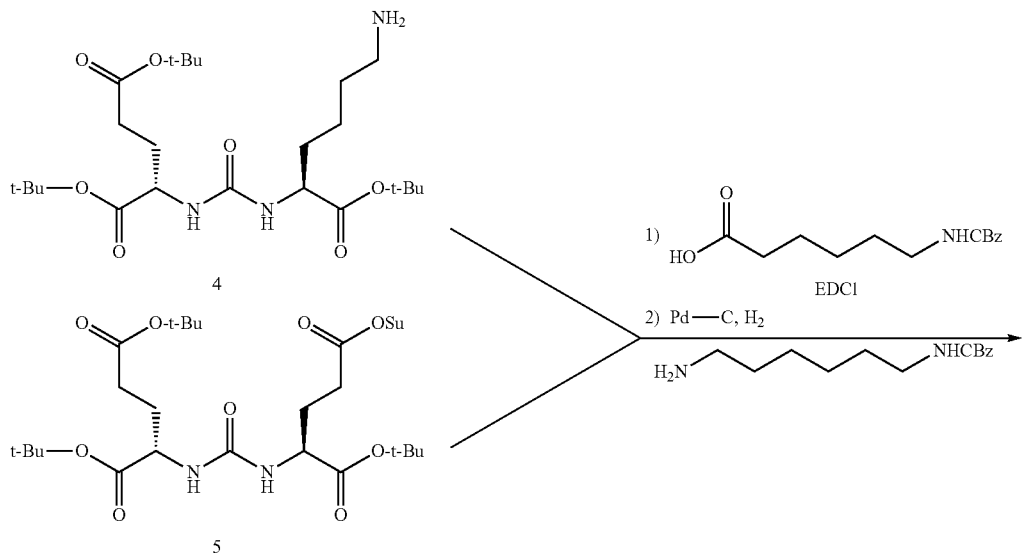

-continued

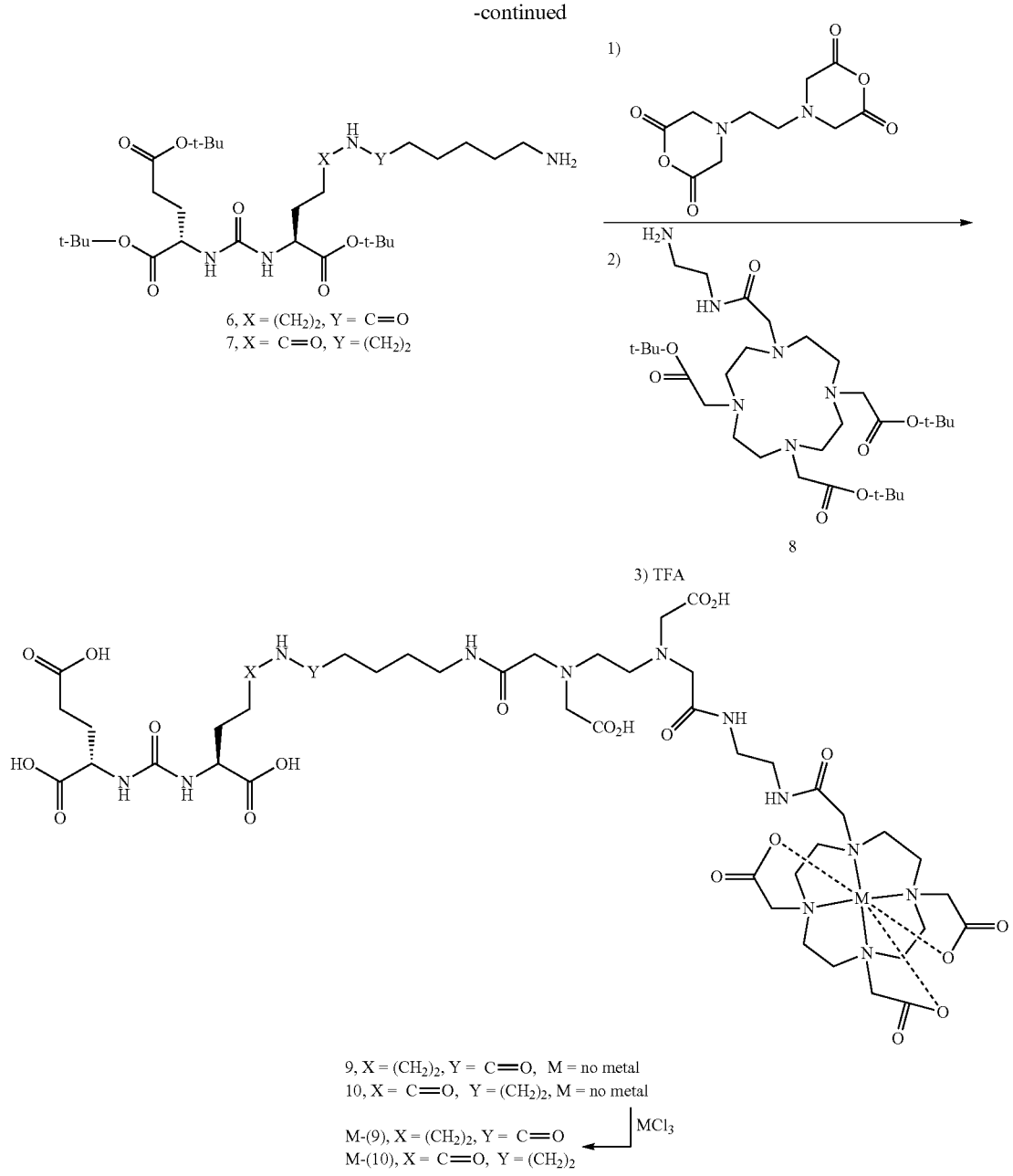

The target compound is obtained using the t-butyl ester of GUL or GUG (4 and 5 respectively) as starting materials. In the first step, a carboxybenzyloxy (Cbz)-protected aminohexanoic acid is reacted with GUL to afford protected intermediate (6). If GUG is used as the recognition moiety, however, GUG is contacted with a Cbz-protected diaminohexane to afford protected intermediate (7). After removal of the Cbz protecting groups by catalytic hydrogenation, intermediates (6) and (7) were brought in contact with EDTA dianhydride followed contact with the commercially available protected DOTA derivative 8. Subsequent deprotection of the t-butyl ester groups afforded the desired EDTA-DOTA analogs 9 and 10. Complexation of 9 or 10 with the desired radioactive or non-radioactive metal isotope gave the desired metal complexes M-(9) and M-(10)

B. Scheme 2 illustrates a general synthetic route for utilization of aspartic acid (Asp) or glutamic acid (Glu) linkers between the PSMA recognition sequence and the DOTA chelator.

Scheme 2
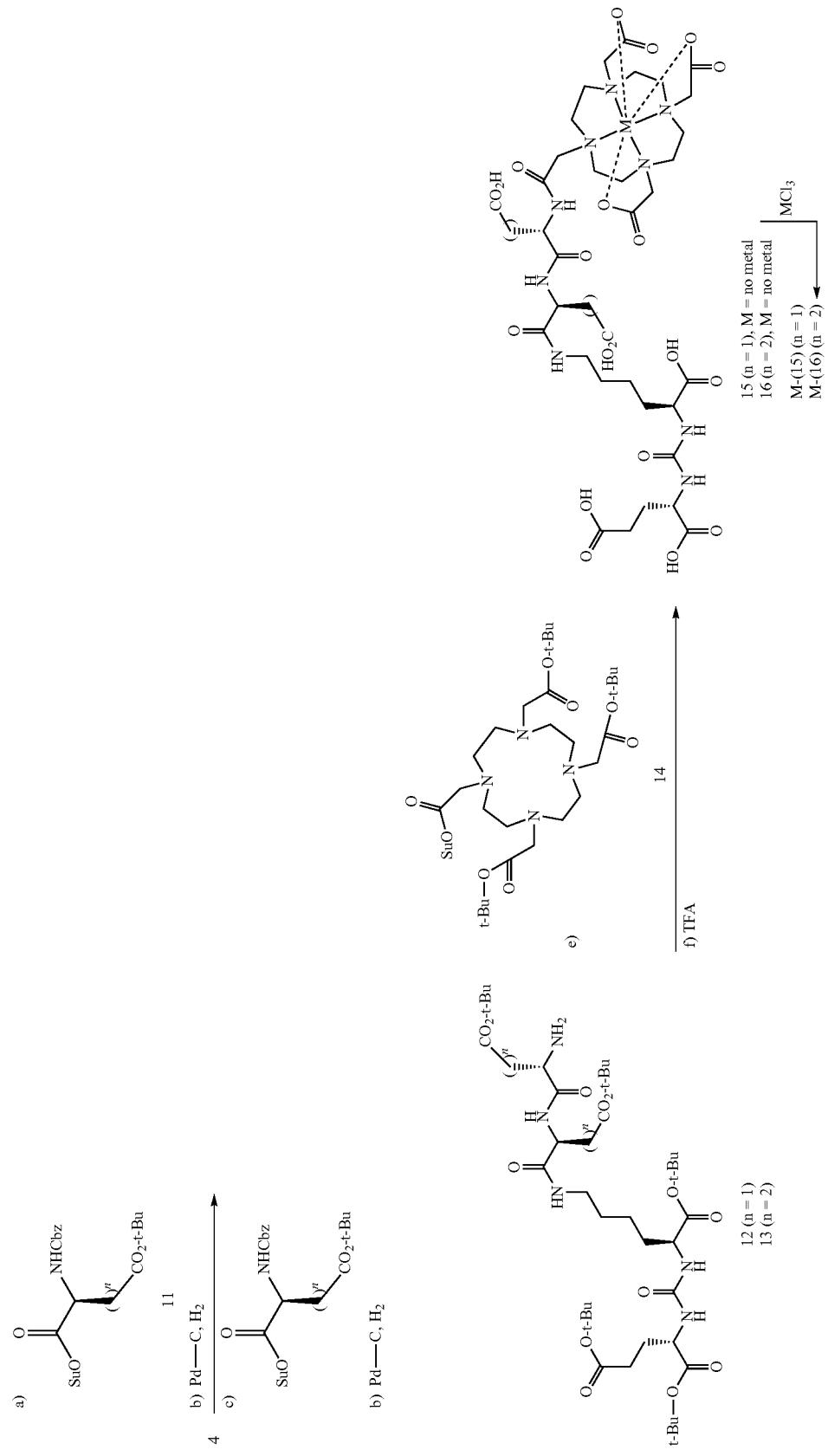

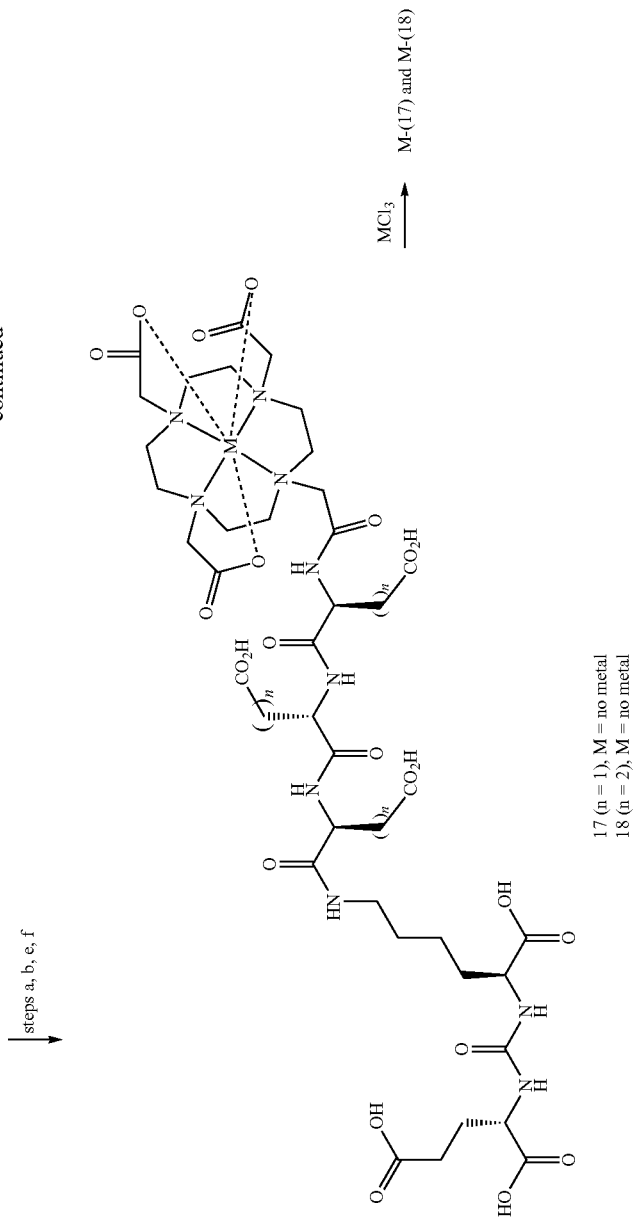

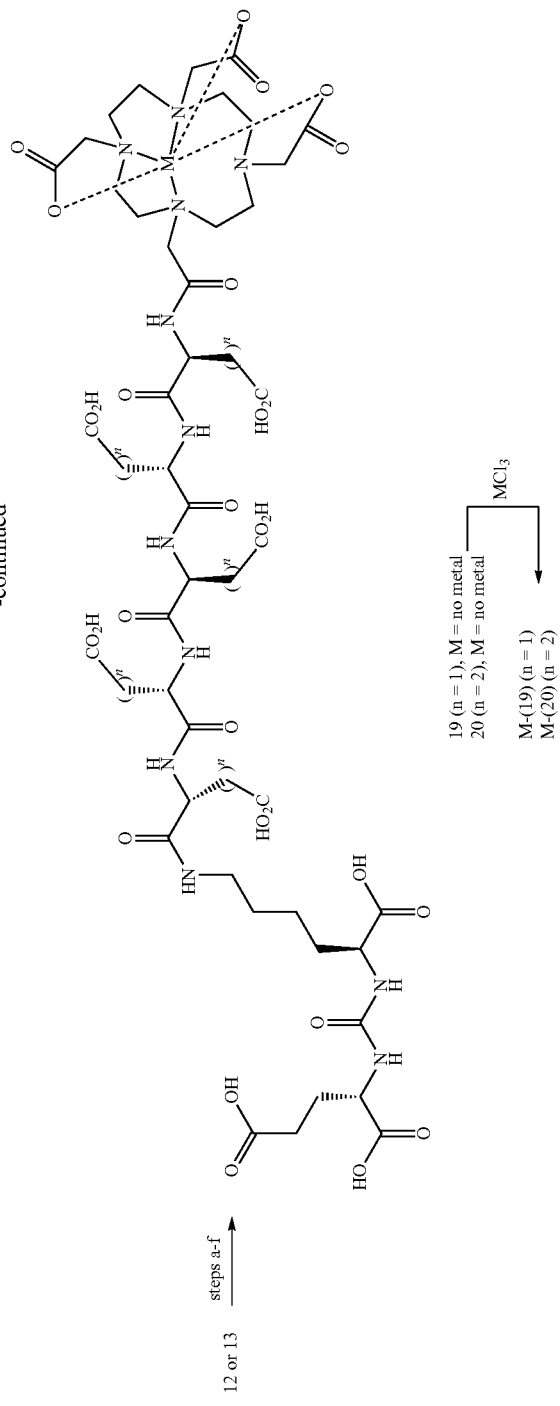

In this series two, three, four, five, or six Asp or Glu residues may serve as the pharmacokinetic modifying linker. The synthesis includes contacting GUL (intermediate 4), with an appropriately protected aspartic acid or glutamic acid residue, followed by removal of the amine protecting group and further contact with a second protected aspartic acid or glutamic acid residue. The above steps of addition and deprotection can be carried out sequentially until the desired number of aspartic acid or glutamic acid residues are attached to obtain an appropriately sized linker.

In Scheme 2 above, two aspartic acid or glutamic acid residue is present in the linker. Thus, deprotection of the Cbz protecting group of the second aspartic acid or glutamic acid residue gave compounds 12 and 13. Conjugation of 12 or 13 with the commercially available activated DOTA derivative 14 followed by deprotection of the t-butyl ester protecting groups gave 15 and 16. Complexation of 15 or 16 with the desired radioactive or non-radioactive metal isotope was straightforward and resulted in the desired metal complexes M-(15) and M-(16). The synthesis of analogs having three, four, five, six or more aspartic acid or glutamic acid residues proceeds in a manner analogous to the one described above for the di-aspartic acid or di-glutamic acid linker.

Thus, using intermediates 12 and 13 as starting materials and repeating the coupling deprotection sequence afforded the desired analogs 17, 18, 19 and 20. Deprotection of the t-butyl ester protecting groups followed by complexation with the desired radioactive or non-radioactive metal isotope gave the desired metal complexes M-(17), M-(18), M-(19) and M-(20).

C. Scheme 3 illustrates the general synthetic route for including a chelator group on the pharmacokinetic modifying linker.

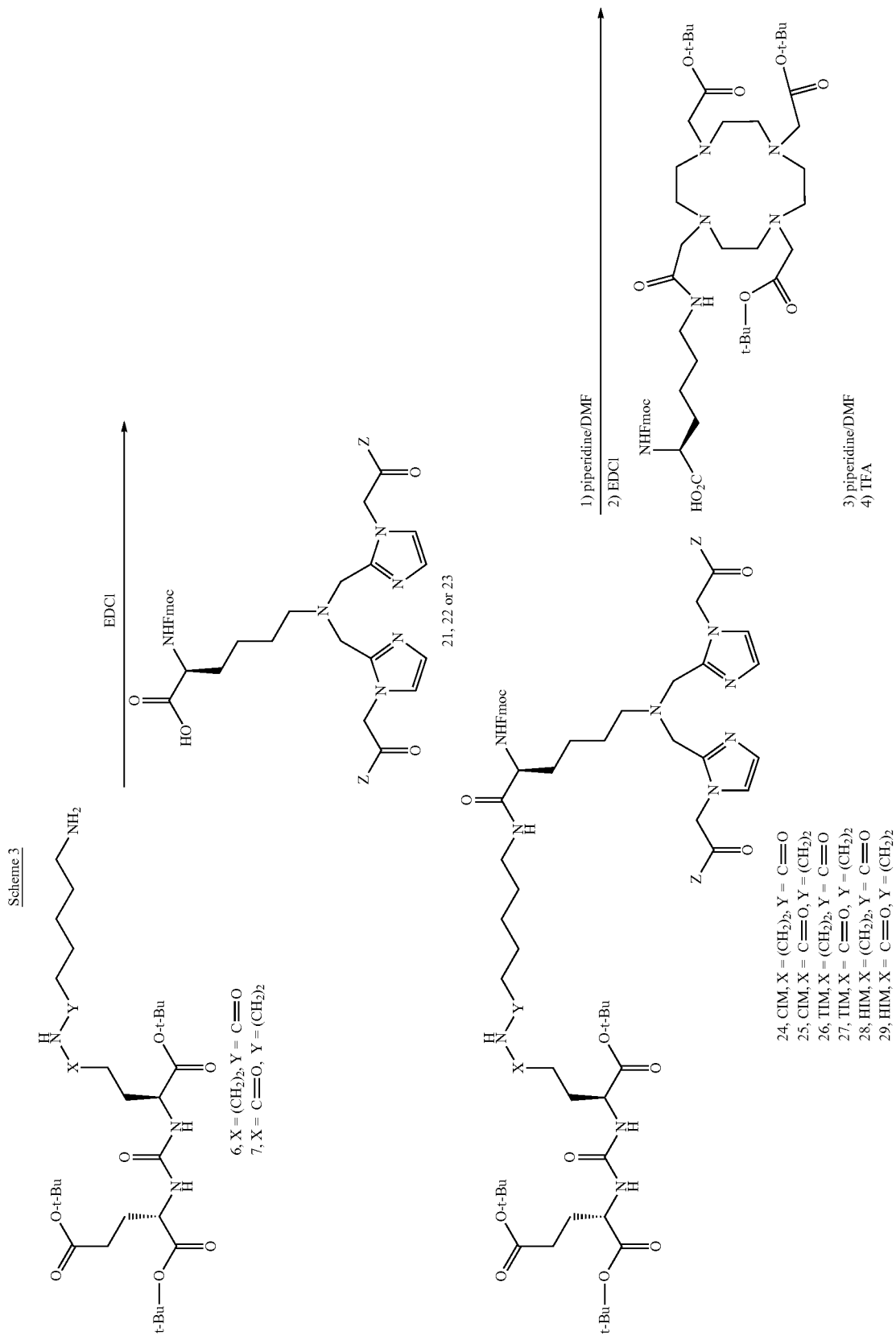

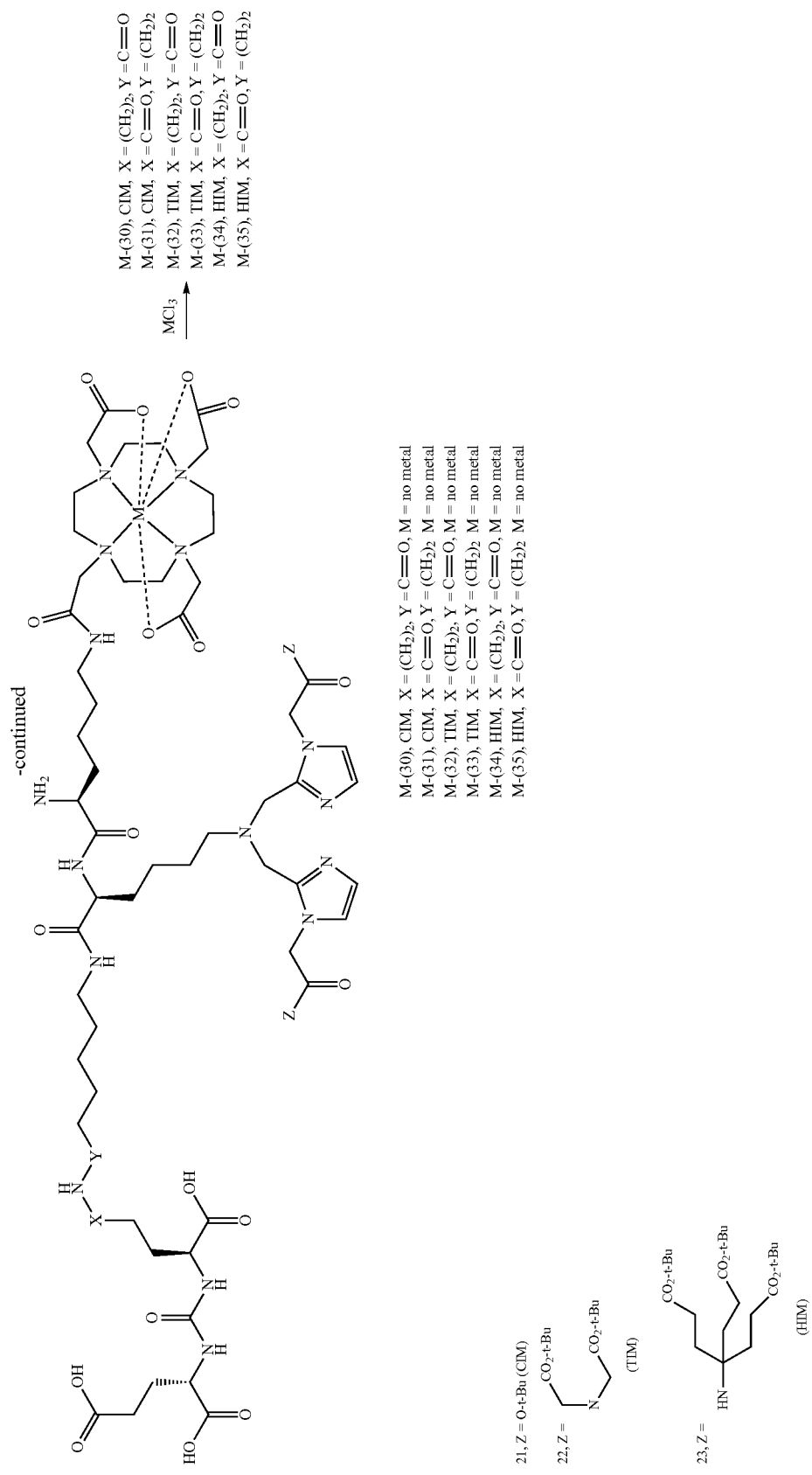

The incorporation of chelator groups on the pharmacokinetic modifying linker proceeds in a manner analogous to the ones described above. Briefly, the GUL-alkylene intermediate having a free amino group (6 or 7) is contacted with Fmoc protected derivative 21 (CIM), 22 (TIM) or 23 (HIM) under standard peptide coupling conditions to afford the protected intermediates 24-29. These intermediates are then coupled to DOTA using synthetic protocols described above. The resultant compounds (30-35) are complexed with the desired radionuclide to afford the DOTA metal complexes M-(30)-M-(35).

D. Schemes 4, 5 and 6 illustrate methods for synthesizing GUL-SCN-Bn-DOTA compounds and their metal complexes.

Scheme 4

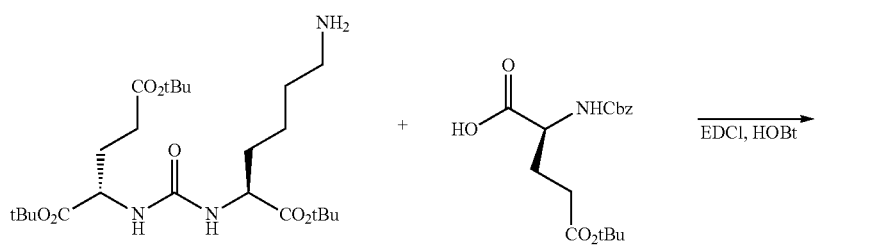

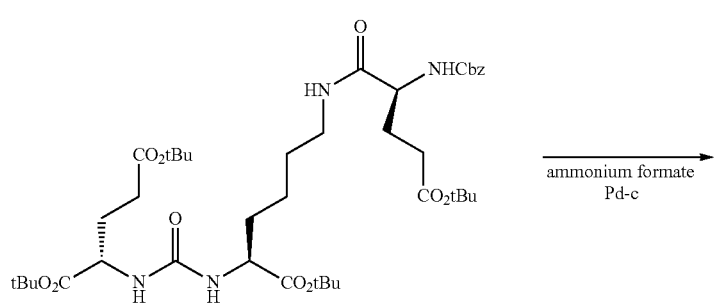

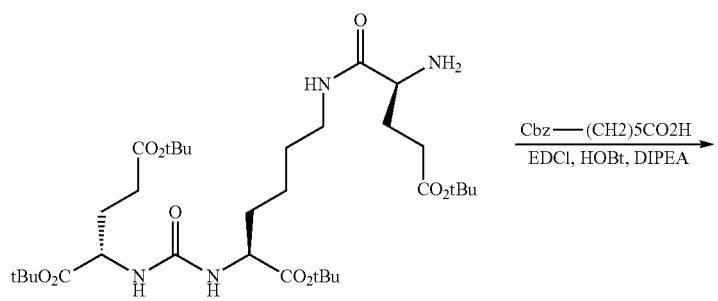

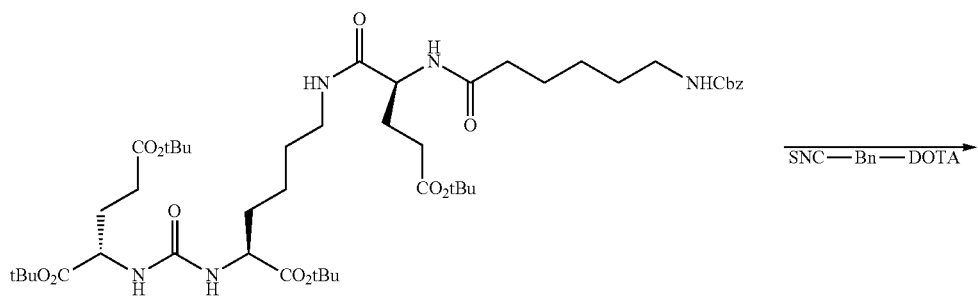

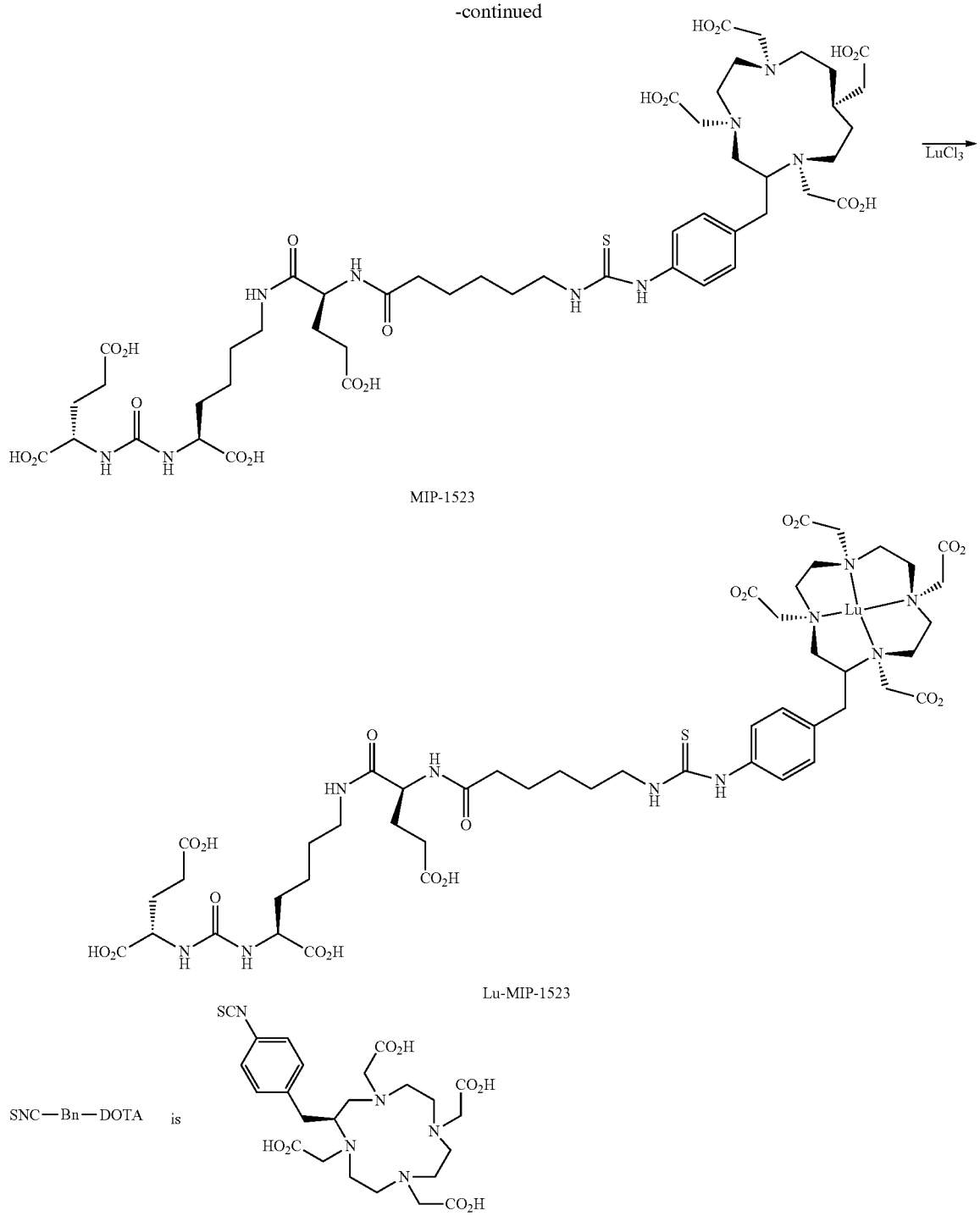

MIP-1523

Lu-MIP-1523

SNC—Bn—DOTA is

Briefly GUL conjugates were prepared from the known protected intermediate (S)-di-tert-butyl 2-(3-((S)-6-amino-1-(tert-butoxy)-1-oxohexan-2-yl)ureido)pentanedioate (GUL-(OtBu)$_3$). Standard amide bond formation (EDCI, HOBt, DIPEA) with Cbz-protected amino acids followed by deprotection of the Cbz group by hydrogenolyis using Pd—C and ammonium formate gave the desired GUL moiety. The sequence can be repeated with additional Cbz-protected amino acids if desired. Linear amino acids such as N-Cbz-6-hexanoic acid were used in one embodiment as the linker for conjugation to the DOTA chelator. Deprotection of the t-butyl ester protecting groups with TFA followed by conjugation to commercially available SCN-Bn-DOTA and HPLC purification afforded the final pure ligand conjugates.

Complexation of the GUL-SCN-Bn-DOTA conjugate with cold lutetium was accomplished by warming an aqueous solution of the GUL-SCN-Bn-DOTA conjugate (MIP1523) and LuCl$_3$ for 30 minutes followed by lyophilization to afford the desired (10S,17S,21S)-10-(2-carboxyethyl)-8,11,19-trioxo-1-((4-((1,4,7,10-tetrakis(carboxymethyl)-1,4,7,10-tetraazacyclododecan-2-yl)methyl)phenyl)amino)-1-thioxo-2,9,12,18,20-pentaazatricosane-17,21,23-tricarboxylate Lu complex.

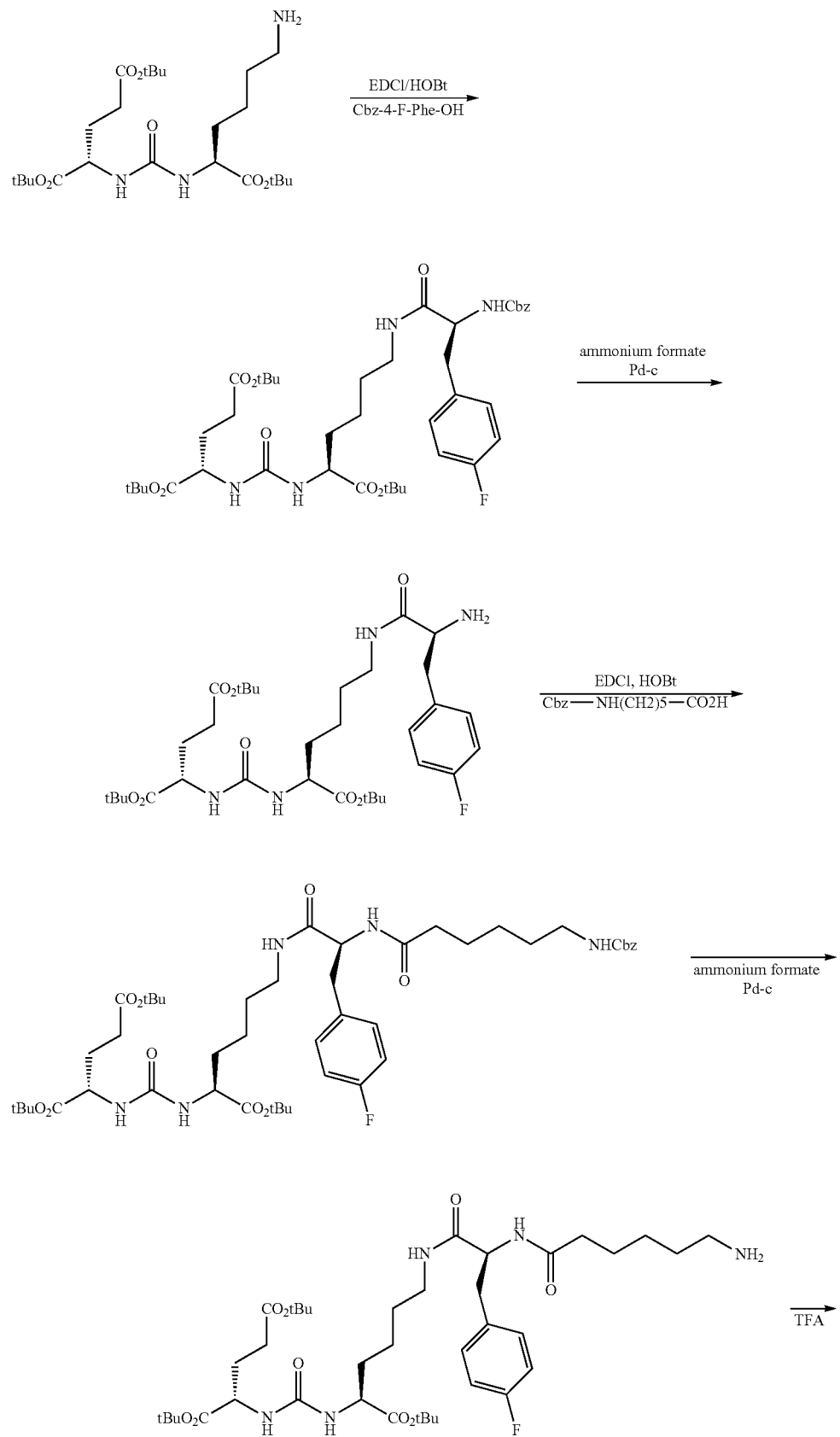
Scheme 5

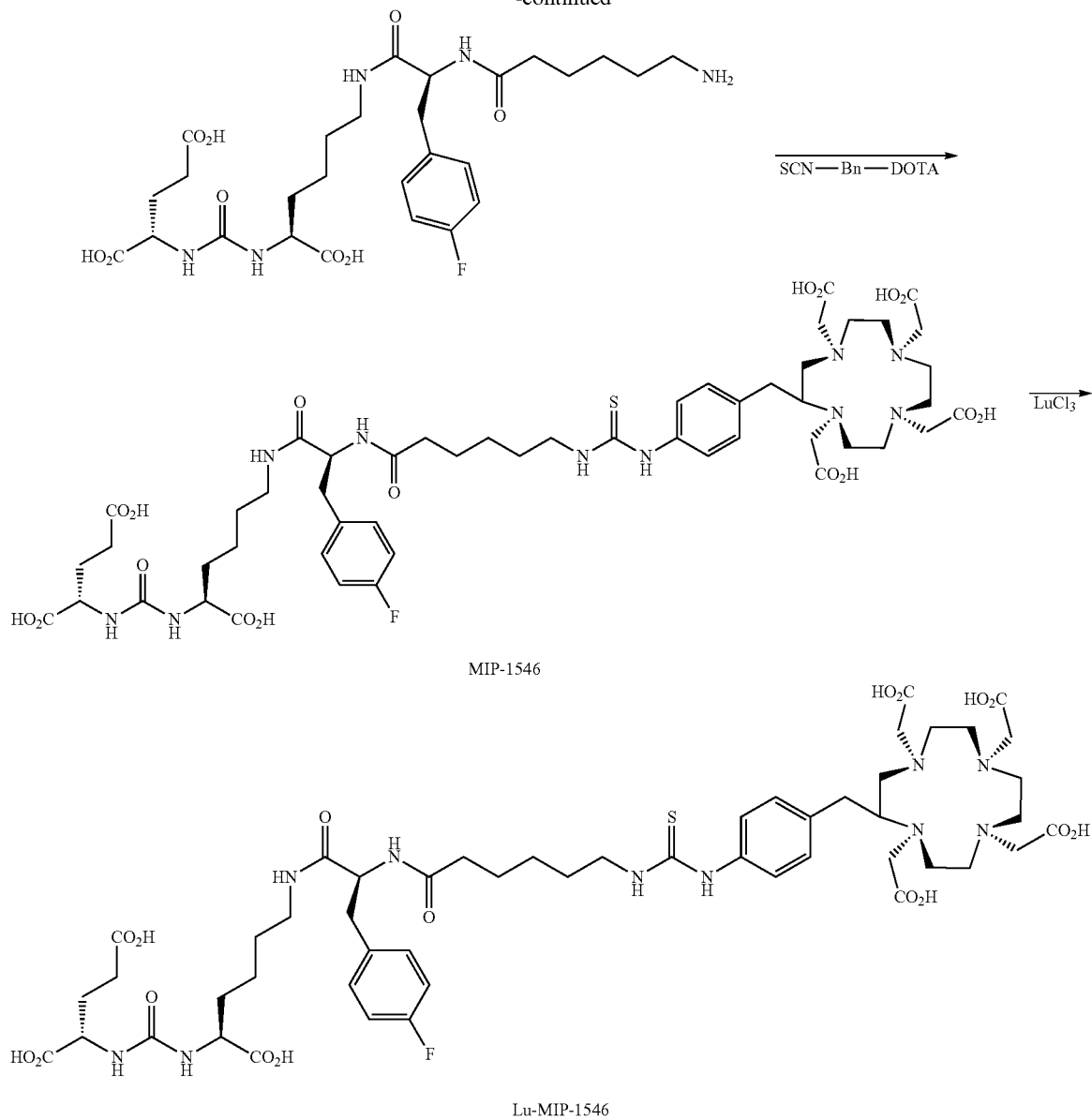
MIP-1546
Lu-MIP-1546
The protocol illustrated in Scheme 5 above was used to synthesize (10S,17S,21S)-10-(4-fluorobenzyl)-8,11,19-trioxo-1-((4-((1,4,7,10-tetrakis(carboxymethyl)-1,4,7,10-tetraazacyclododecan-2-yl)methyl)phenyl)amino)-1-thioxo-2,9,12,18,20-pentaazatricosane-17,21,23-tricarboxylic acid and its lutetium complex.
Scheme 6
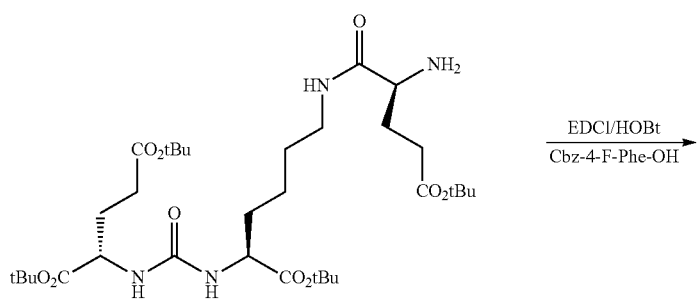

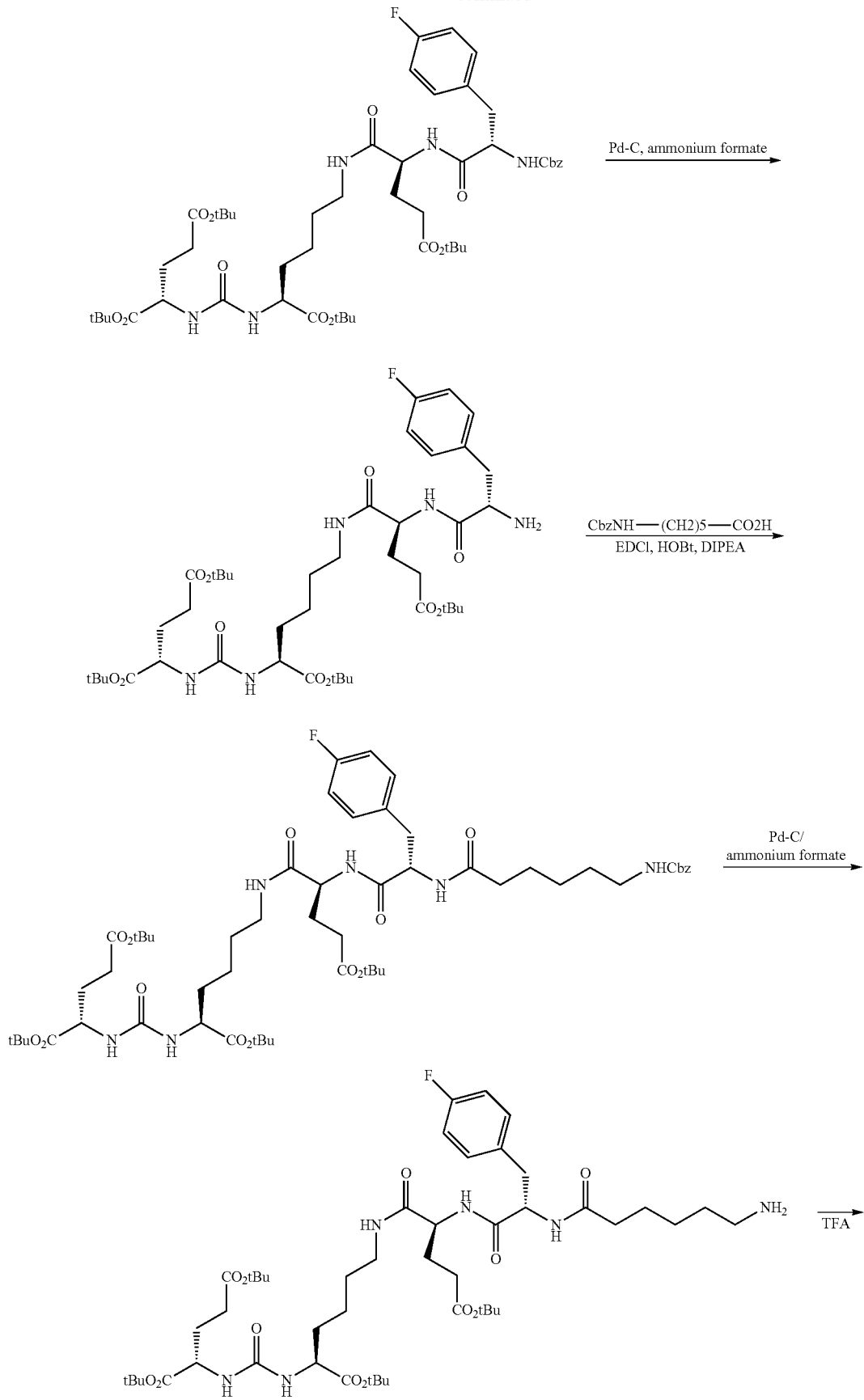

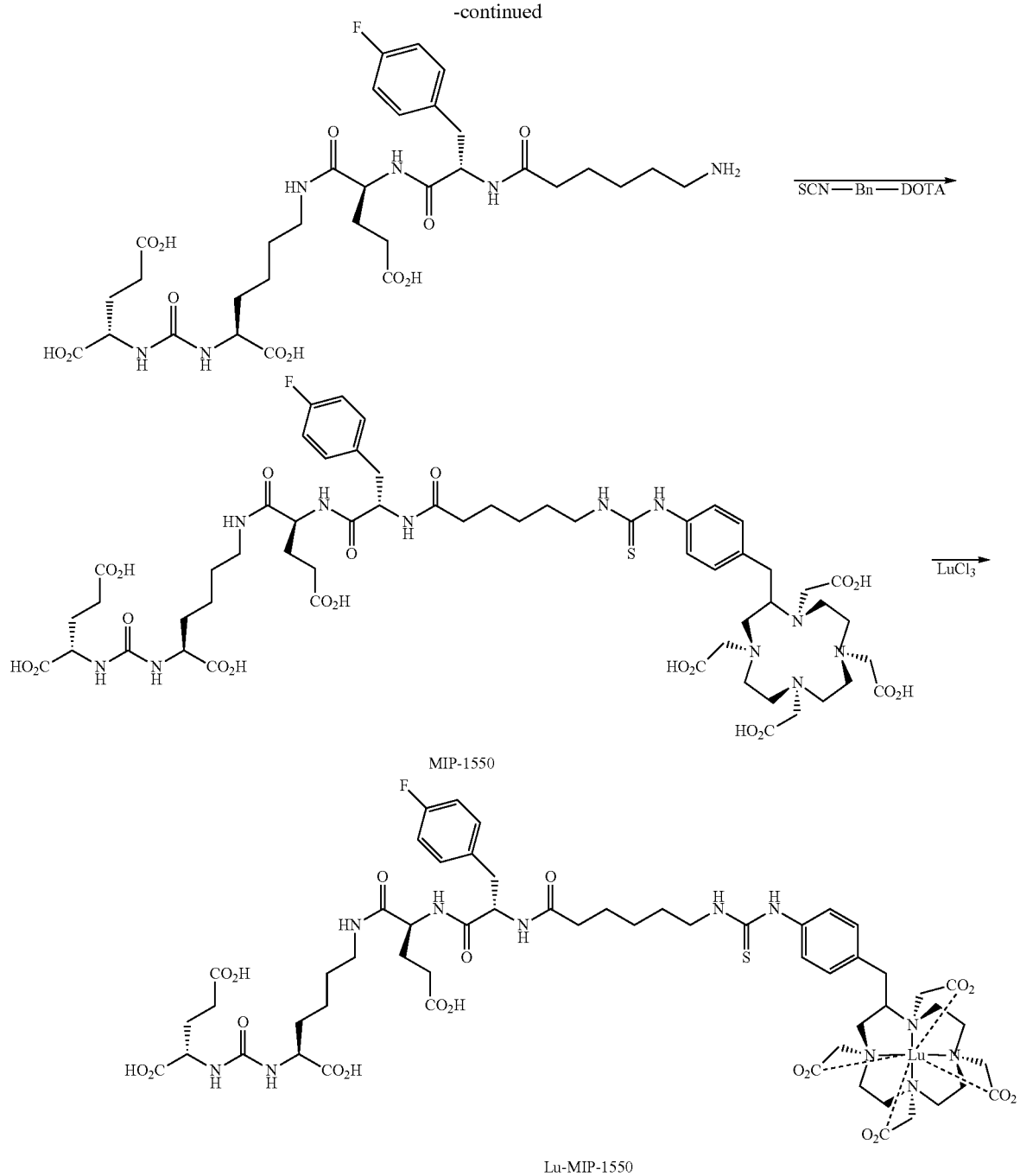

MIP-1550

Lu-MIP-1550

The protocol illustrated in Scheme 6 above was used to synthesize (10S,13S,20S,24S)-13-(2-carboxyethyl)-10-(4-fluorobenzyl)-8,11,14,22-tetraoxo-1-((4-((1,4,7,10-tetrakis(carboxymethyl)-1,4,7,10-tetraazacyclododecan-2-yl)methyl)phenyl)amino)-1-thioxo-2,9,12,15,21,23-hexaazahexacosane-20,24,26-tricarboxylic acid and its lutetium complex.

E. Schemes 7, 8 and 9 illustrate a route for synthesizing GUG-SCN-Bn-DOTA compounds and their metal complexes. The GUG-SCN-Bn-DOTA compounds and their metal complexes were synthesized using (S)-5-(tert-butoxy)-4-(3-((S)-1,5-di-tert-butoxy-1,5-dioxopentan-2-yl)ureido)-5-oxopentanoic acid (GUG-(OtBu)₃). Standard amide bond forming reagents, such as EDCI, HOBt, DIPEA were used to conjugate the side chain carboxylic acid of GUG to the amino group of aspartate methyl ester or other amines.

Deprotection of the methyl ester was effected by hydrolysis using LiOH/MeOH gives t-butyl ester protected free acids which can be coupled to additional amino acids protected as their methyl esters or to a mono N-Boc-protected diaminoalkane. Deprotection of the t-butyl ester and Boc protecting groups was carried out using a dichloromethan solution of trifluoroacetic acid (TFA/DCM). Conjugation to commercially available SCN-Bn-DOTA followed by HPLC purification afforded the final pure ligand conjugates. The complexation of the GUG-SCN-Bn-DOTA conjugates with cold lutetium was accomplished by warming an aqueous solution of LuCl₃ containing the GUG-SCN-Bn-DOTA conjugate for 30 min followed by lyophilization to afford the pure desired Lu-complexes.
Scheme 7
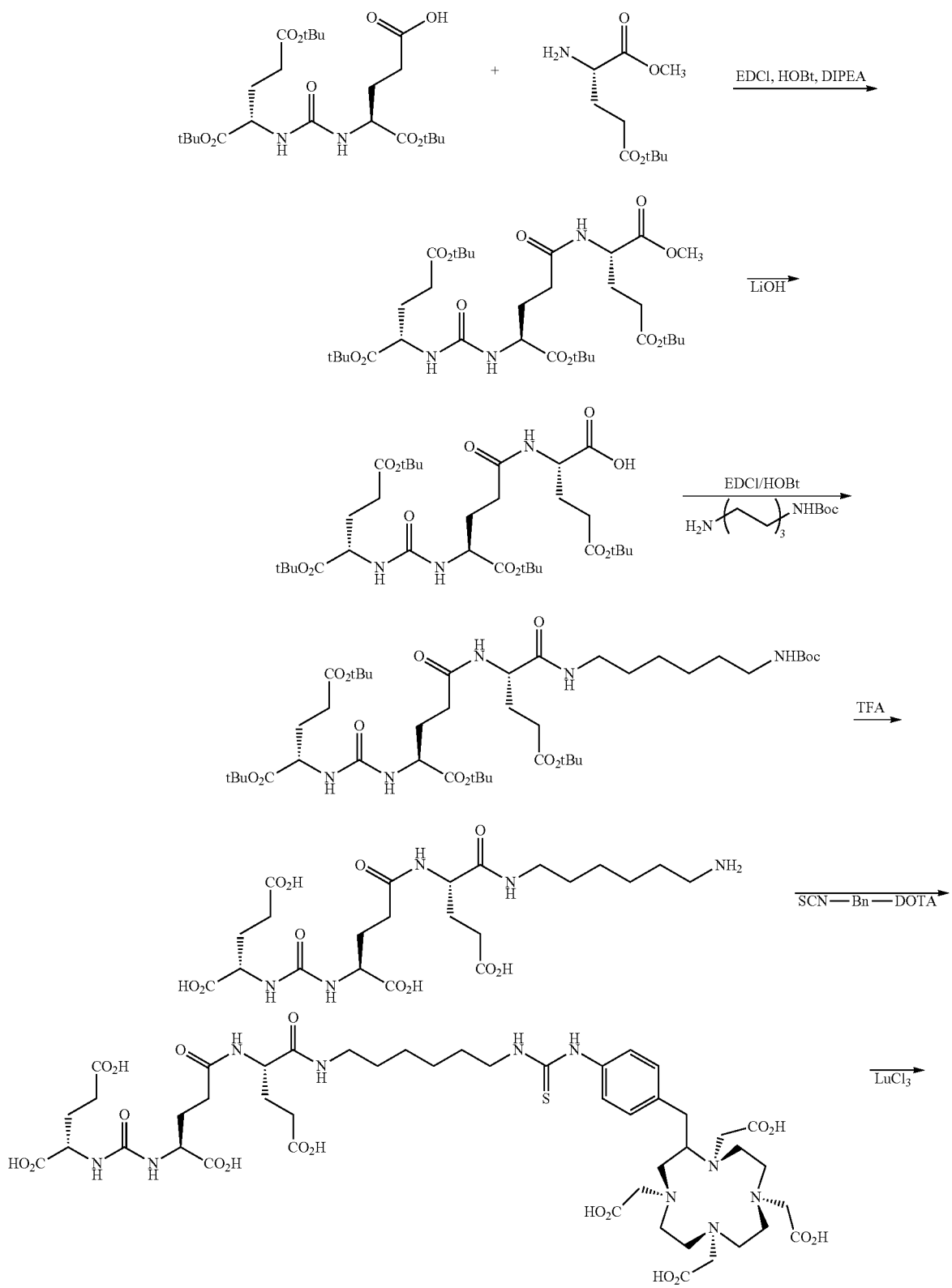
MIP-1519

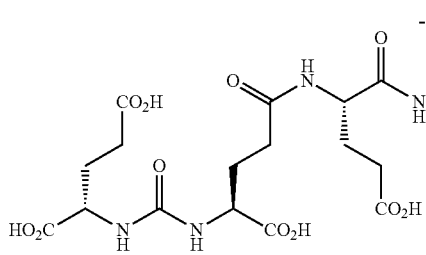
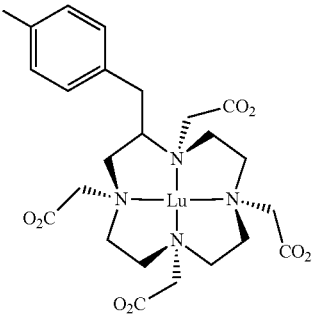
Lu-MIP-1519
The protocol illustrated in Scheme 7 above was used to synthesize (11S,16S,20S)-11-(2-carboxyethyl)-10,13,18-trioxo-1-((4-((1,4,7,10-tetrakis(carboxymethyl)-1,4,7,10-tetraazacyclododecan-2-yl)methyl)phenyl)amino)-1-thioxo-2,9,12,17,19-pentaazadocosane-16,20,22-tricarboxylic acid and its lutetium complex.
Scheme 8
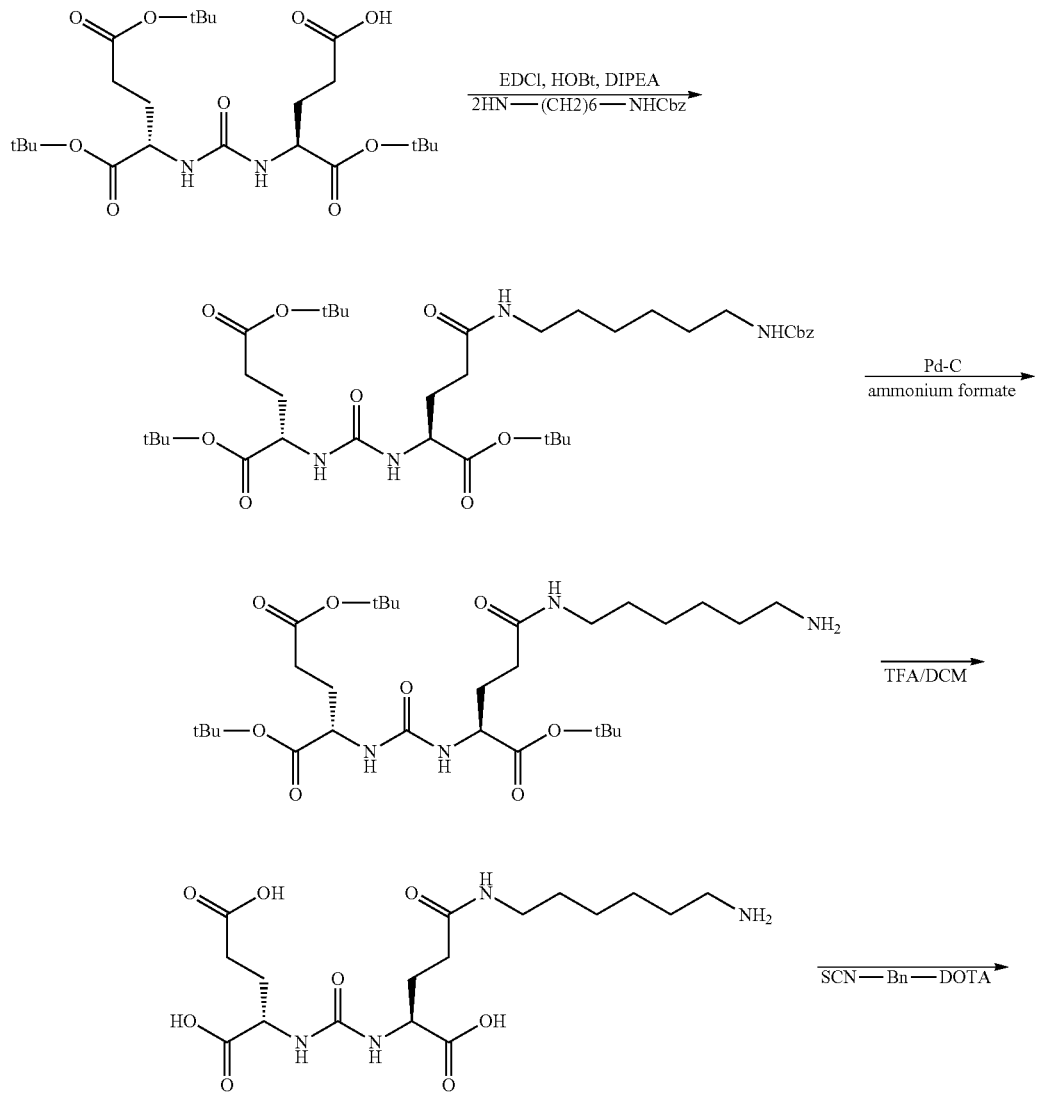

-continued
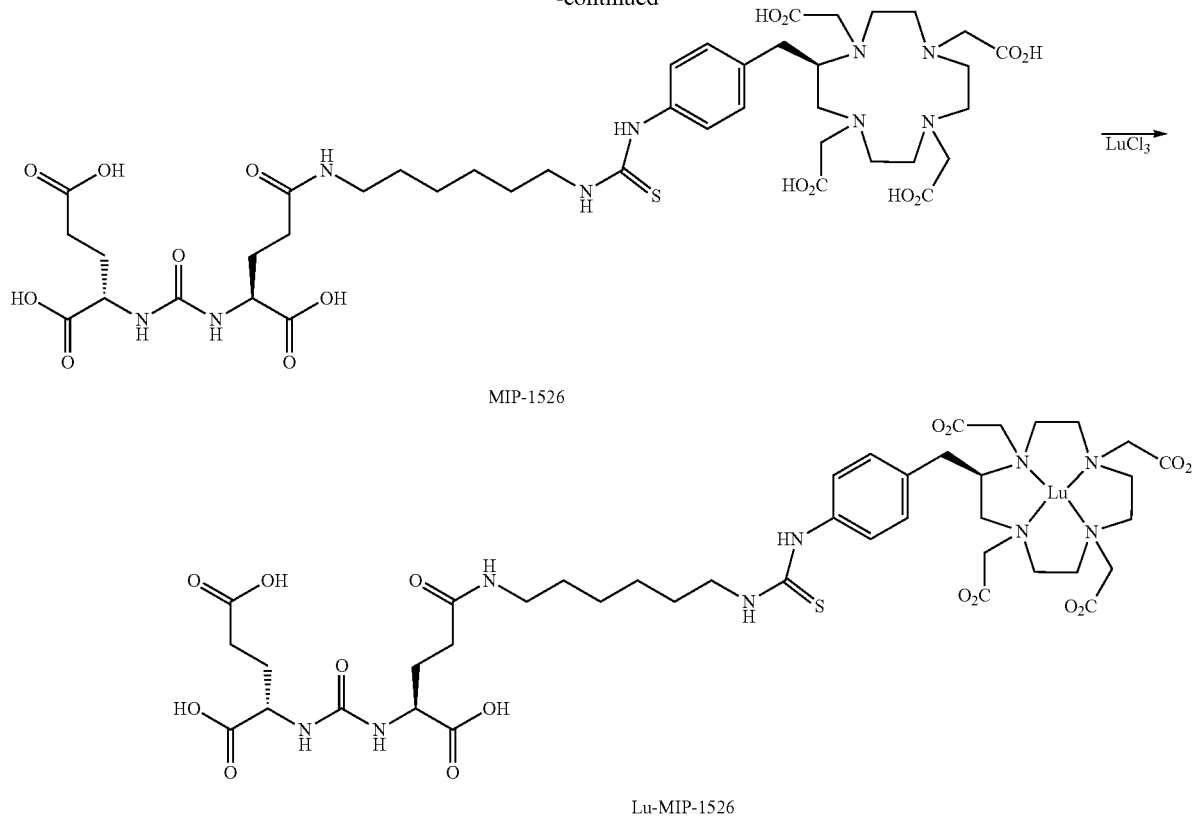
MIP-1526
Lu-MIP-1526
The protocol illustrated in Scheme 8 above was used to synthesize (13S,17S)-10,15-dioxo-1-((4-((1,4,7,10-tetrakis (carboxymethyl)-1,4,7,10-tetraazacyclododecan-2-yl)methyl)phenyl)amino)-1-thioxo-2,9,14,16-tetraazanonadecane-13,17,19-tricarboxylic acid and its lutetium complex.
Example 9
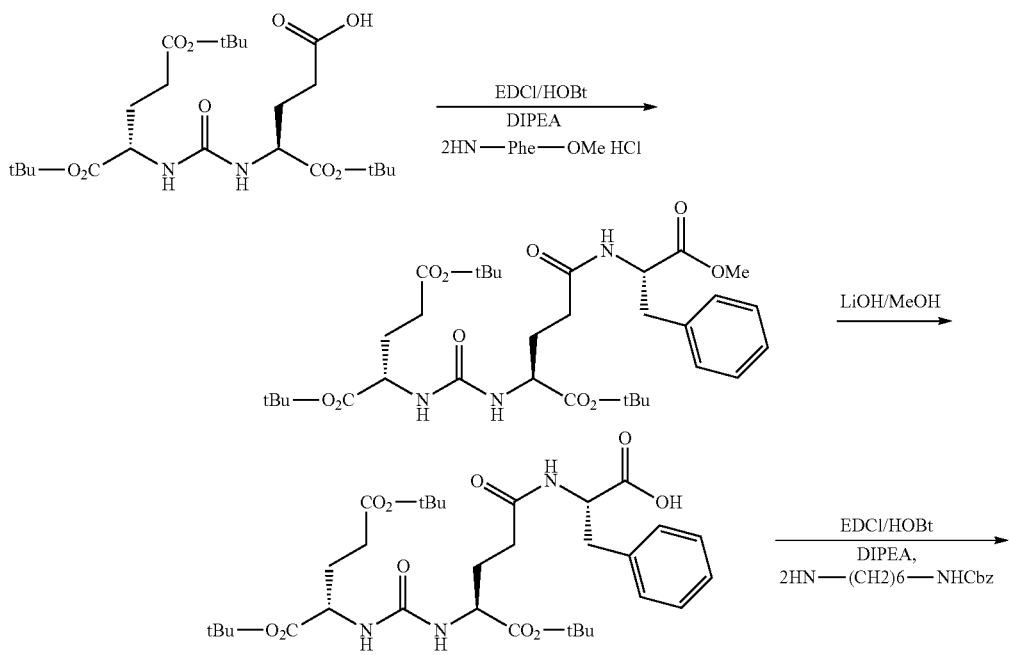

-continued
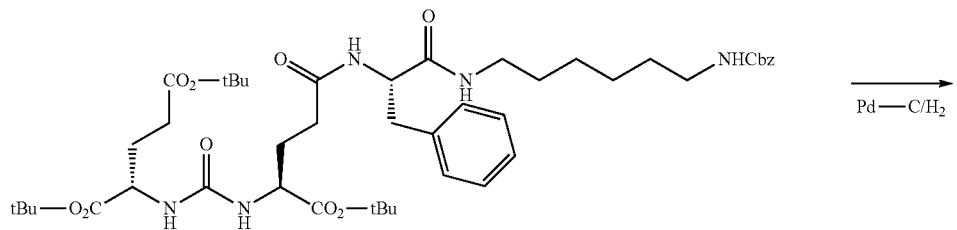
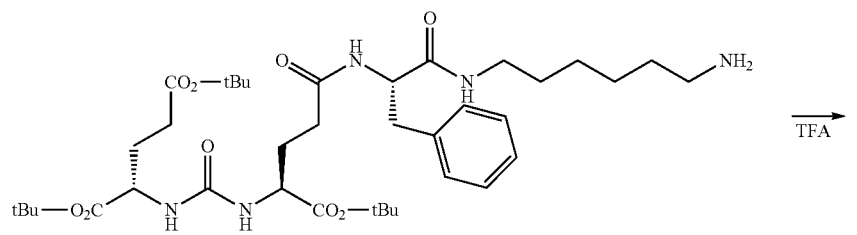
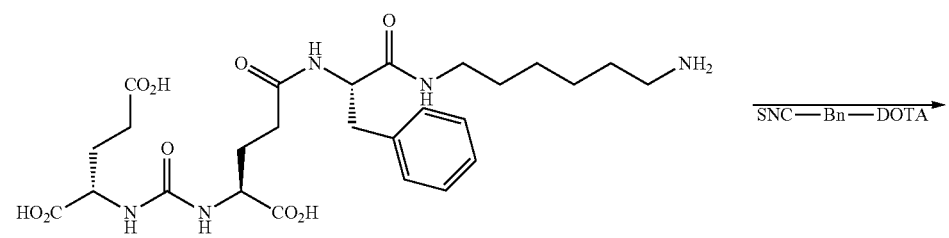
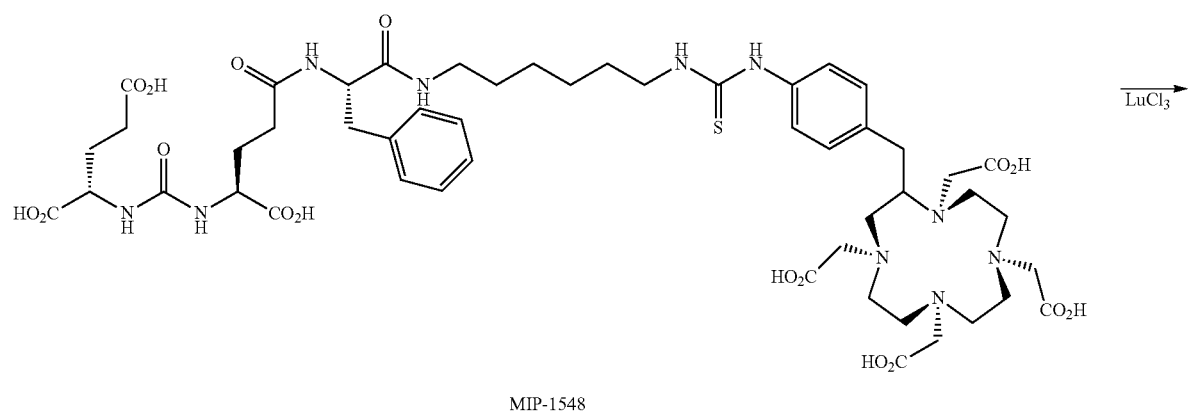
MIP-1548
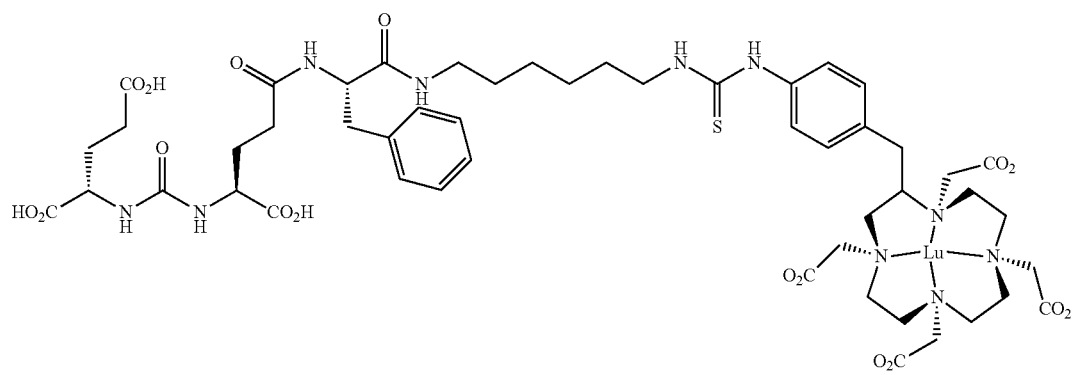
Lu-MIP-1548

The protocol illustrated in Scheme 9 above was used to synthesize (11S,16S,20S)-11-benzyl-10,13,18-trioxo-1-((4-((1,4,7,10-tetrakis(carboxymethyl)-1,4,7,10-tetraazacyclododecan-2-yl)methyl)phenyl)amino)-1-thioxo-2,9,12,17,19-pentaazadocosane-16,20,22-tricarboxylic acid and its lutetium complex.

Scheme 10 provides an exemplary route for conjugating a 2,2'((1Z,11Z)-2,5,8,11-tetraazadodeca-1,11-diene-1,12-diyl)diphenol chelator group to a GUL-linker or GUG-linker moiety to obtain a Formula I or Formula II compound.

Scheme 10

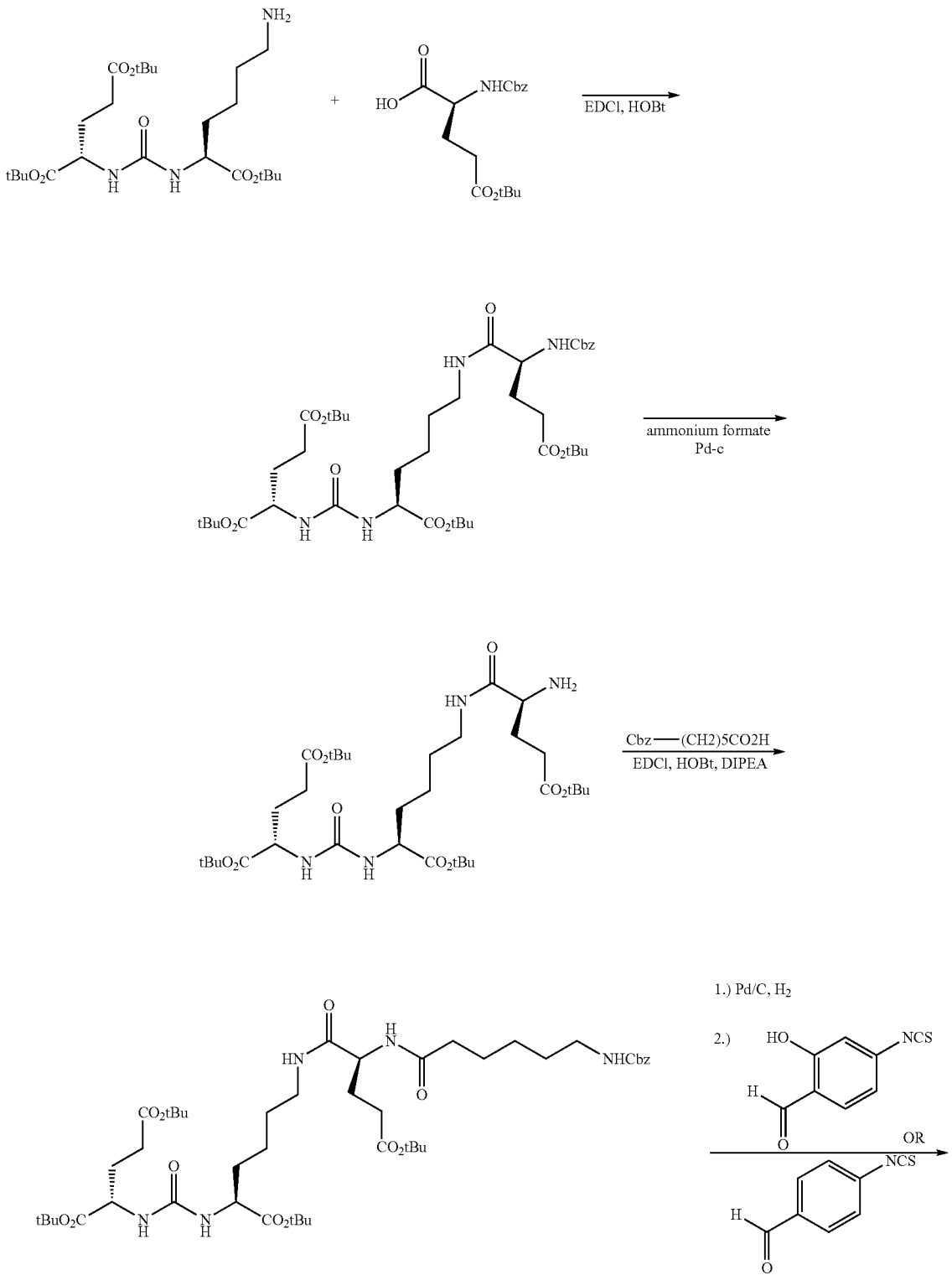

109

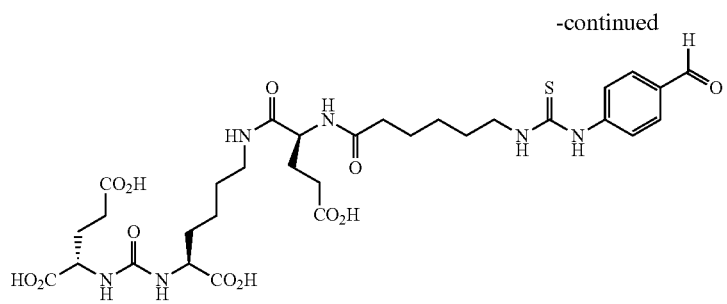

110

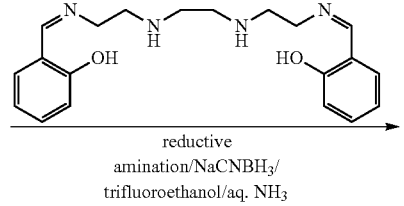

reductive amination/NaCNBH$_3$/ trifluoroethanol/aq. NH$_3$

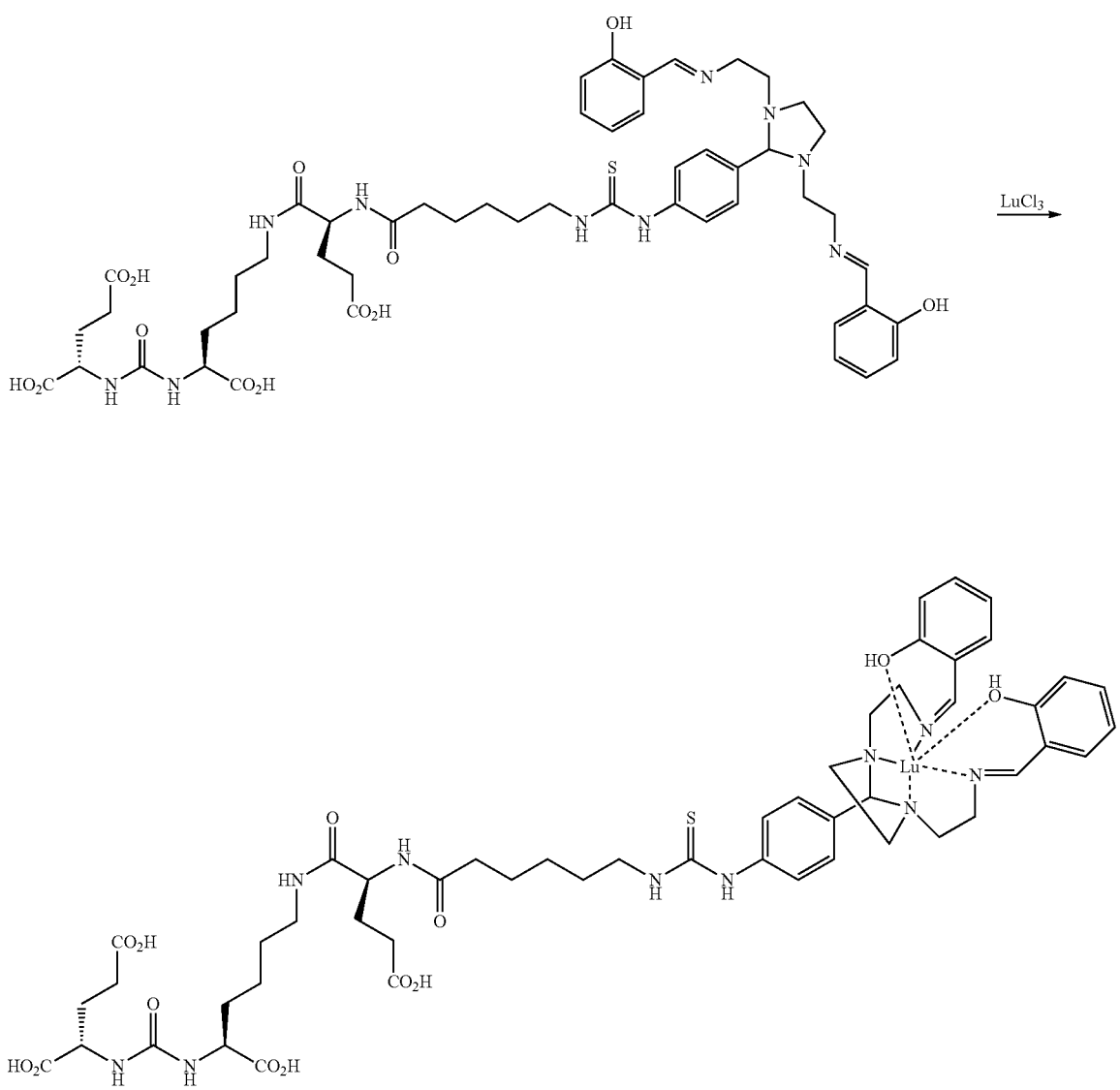

Briefly, a 4-isocyanatobenzaldehyde will be contacted with a GUL-linker or GUG-linker conjugate to provide the corresponding 4-formylphenyl-1-thiourea. This moiety will then be contacted with the chelator to obtain the desired Formula I-chelator or Formula II-chelator compounds. The conjugation of the chelator group to a GUL-linker or GUG-linker moiety can be performed under reductive amination conditions.

Synthetic protocols schematically illustrated above were used to manufacture other Formula I and Formula II compounds as further described below.

Synthesis and Characterization

Example 1

(14S,18S)-1-(1-(2-(bis(carboxymethy)amino)-2-oxoethyl)-1H-imidazol-2-yl)-8,16-dioxo-2-(4-((1-(3-(2-(4,7,10-tris(carboxymethyl)-1,4,7,10-tetraazacyclododecan-1-yl)acetamido)propyl)-1H-1,2,3-triazol-4-yl)methoxy)benzyl)-2,9,15,17-tetraazaicosane-14,18,20-tricarboxylic acid Indium complex (MIP-1445)

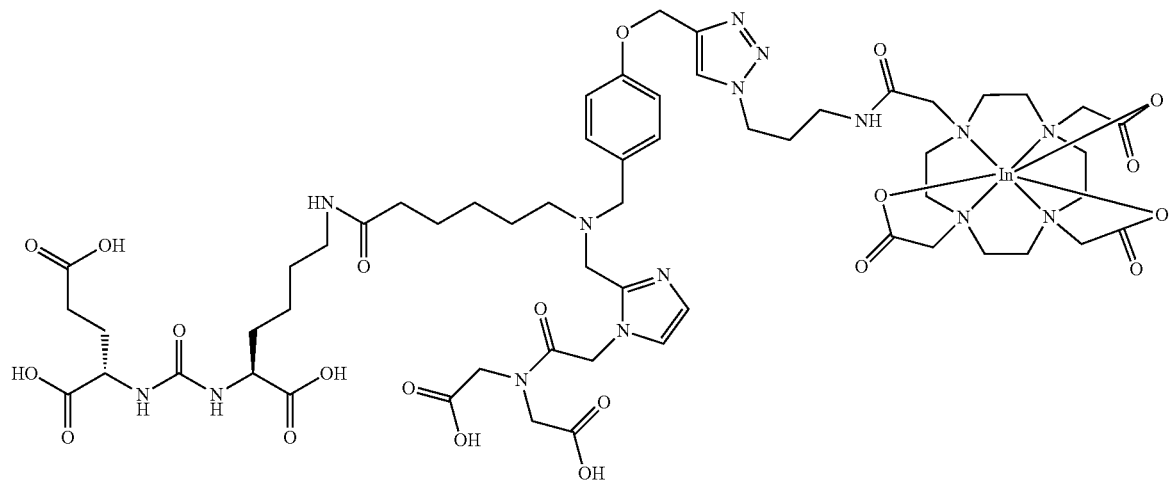

Step 1. 6-((4-(prop-2-yn-1-yloxy)benzyl)amino)hexanoic acid

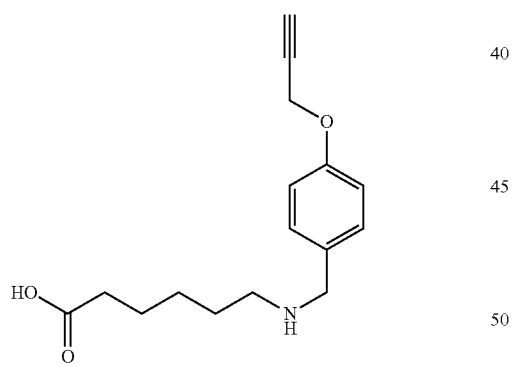

A solution of 6-aminohexanoic acid (2.62 g, 20 mmol), 4-(prop-2-yn-1-yloxy)benzaldehyde (0.80 g, 5.0 mmol) and acetic acid (0.50 mL) in DCE (50 mL) was heated at 80° C. for 60 min. The reaction mixture was cooled to 0° C., and treated with NaBH(OAc)$_3$ (2.11 g, 10 mmol). The reaction was stirred at room temperature for 12 hours and decomposed with water and then extracted with DCM. The organic layer was dried and concentrated under reduced pressure to give a residue, which was purified using a Biotage SP4 and gradient elution of 5-50% methanol in DCM. The yield of the target compound 6-((4-(prop-2-yn-1-yloxy)benzyl)amino)hexanoic acid was 62% (0.856 g). $^1$H NMR (400 MHz, DMSO-d$_6$): δ 7.19 (d, J=8.4 Hz, 2H), 6.86 (d, J=8.4 Hz, 2H), 4.71 (s, 2H), 3.56 (s, 2H), 3.49 (s, 1H), 2.39 (t, J=7.0 Hz, 2H), 2.00 (t, J=7.2 Hz, 2H), 1.41-1.19 (m, 6H); MS (ESI), 276.1 (M+H)$^+$.

Step 2. 6-(((1-(2-(bis(2-(tert-butoxy)-2-oxoethyl)amino)-2-oxoethyl)-1H-imidazol-2-yl)methyl)(4-(prop-2-yn-1-yloxy)benzyl)amino)hexanoic acid

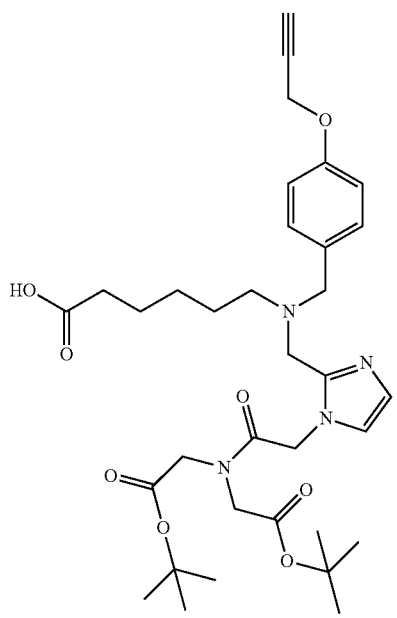 [SMILES: C#CCOc1ccc(CN(CCCCCC(=O)O)Cc2nccn2CC(=O)N(CC(=O)OC(C)(C)C)CC(=O)OC(C)(C)C)cc1]

A solution of 6-((4-(prop-2-yn-1-yloxy)benzyl)amino)hexanoic acid (0.715 g, 2.60 mmol), tert-butyl 2,2'-(2-(2-formyl-1H-imidazol-1-yl)acetylazanediyl)diacetate (0.99 g, 2.60 mmol) and acetic acid (0.10 mL) in DCE (80 mL) at 0° C. was treated with NaBH(OAc)$_3$ (1.05 g, 5.0 mmol). The reaction mixture was stirred at 0° C. for 30 min and at room temperature overnight and decomposed with water and methanol. The reaction mixture was concentrated under reduced pressure to give a residue, and purified via Biotage SP4 silica gel column to afford 6-(((1-(2-(bis(2-(tert-butoxy)-2-oxoethyl)amino)-2-oxoethyl)-1H-imidazol-2-yl)methyl)(4-(prop-2-yn-1-yloxy)benzyl)amino)hexanoic acid (0.3313 g, 20%). $^1$H NMR (400 MHz, DMSO-d$_6$): δ 11.90 (s, 1H), 7.17 (d, J=8.4 Hz, 2H), 6.94 (s, 1H), 6.87 (d, J=8.4 Hz, 2H), 6.74 (s, 1H), 5.02 (s, 2H), 4.72 (d, J=2.4 Hz, 2H), 4.24 (s, 2H), 3.94 (s, 2H), 3.48 (s, 2H), 3.51 (s, 1H), 3.40 (s, 2H), 2.21 (t, J=7.2 Hz, 2H), 2.10 (t, J=7.4 Hz, 2H), 1.45-1.35 (m, 22H), 1.11-1.06 (m, 2H); MS (ESI), 641.3 (M+H)$^+$.

Step 3. (14S,18S)-tri-tert-butyl 1-(1-(2-(bis(2-(tert-butoxy)-2-oxoethyl)amino)-2-oxoethyl)-1H-imidazol-2-yl)-8,16-dioxo-2-(4-(prop-2-yn-1-yloxy)benzyl)-2,9,15,17-tetraazaicosane-14,18,20-tricarboxylate

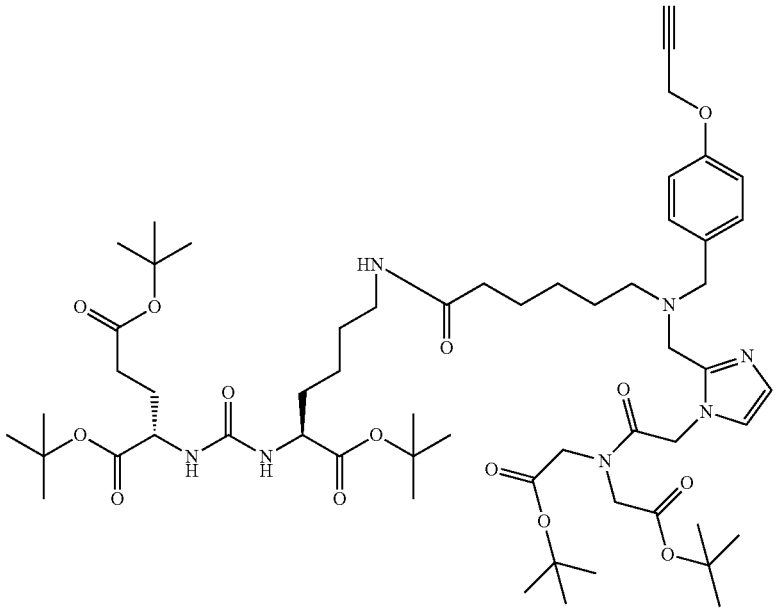 [SMILES: C#CCOc1ccc(CN(CCCCCC(=O)NCCCC[C@H](NC(=O)N[C@@H](CCC(=O)OC(C)(C)C)C(=O)OC(C)(C)C)C(=O)OC(C)(C)C)Cc2nccn2CC(=O)N(CC(=O)OC(C)(C)C)CC(=O)OC(C)(C)C)cc1]

A solution of (S)-di-tert-butyl 2-(3-((S)-6-amino-1-(tert-butoxy)-1-oxohexan-2-yl)ureido)pentanedioate (0.742 g, 1.52 mmol), 6-(((1-(2-(bis(2-(tert-butoxy)-2-oxoethyl)amino)-2-oxoethyl)-1H-imidazol-2-yl)methyl)(4-(prop-2-yn-1-yloxy)benzyl)amino)hexanoic acid (0.244 g, 0.38 mmol), EDCI (0.290 g, 1.52 mmol), HOBt (0.051 g, 0.38 mmol) and DIPEA (0.40 mL) in DCE (5.0 mL) was stirred at room temperature for 4 h. The solvent was evaporated to give a residue, which was purified by Biotage SP4 eluting with DCM/MeOH to give (14S,18S)-tri-tert-butyl 1-(1-(2-(bis(2-(tert-butoxy)-2-oxoethyl)amino)-2-oxoethyl)-1H-imidazol-2-yl)-8,16-dioxo-2-(4-(prop-2-yn-1-yloxy)benzyl)-2,9,15,17-tetraazaicosane-14,18,20-tricarboxylate (0.3237 g, 77%) as a white solid. $^1$H NMR (400 MHz, DMSO-d$_6$): δ 7.64 (t, J=5.4 Hz, 1H), 7.17 (d, J=8.4 Hz, 2H), 6.93 (s, 1H), 6.87 (d, J=8.8 Hz, 2H), 6.74 (s, 1H), 6.26 (d, J=8.4 Hz, 1H), 6.22 (d, J=8.0 Hz, 1H), 5.02 (s, 2H), 4.72 (d, J=2.0 Hz, 2H), 4.24 (s, 2H), 4.03-3.89 (m, 4H), 3.51 (t, J=2.0 Hz, 1H), 3.48 (s, 2H), 3.39 (s, 2H), 2.95 (q, J=6.3 Hz, 2H), 2.22-2.15 (m, 4H), 1.94 (t, J=7.4 Hz, 2H), 1.85-1.04 (m, 34H); MS (ESI), 1111.6 (M+H)$^+$.

Step 4. (14S,18S)-tri-tert-butyl 2-(4-((1-(3-amino-propyl)-1H-1,2,3-triazol-4-yl)methoxy)benzyl)-1-(1-(2-(bis(2-(tert-butoxy)-2-oxoethyl)amino)-2-oxoethyl)-1H-imidazol-2-yl)-8,16-dioxo-2,9,15,17-tetraazaicosane-14,18,20-tricarboxylate

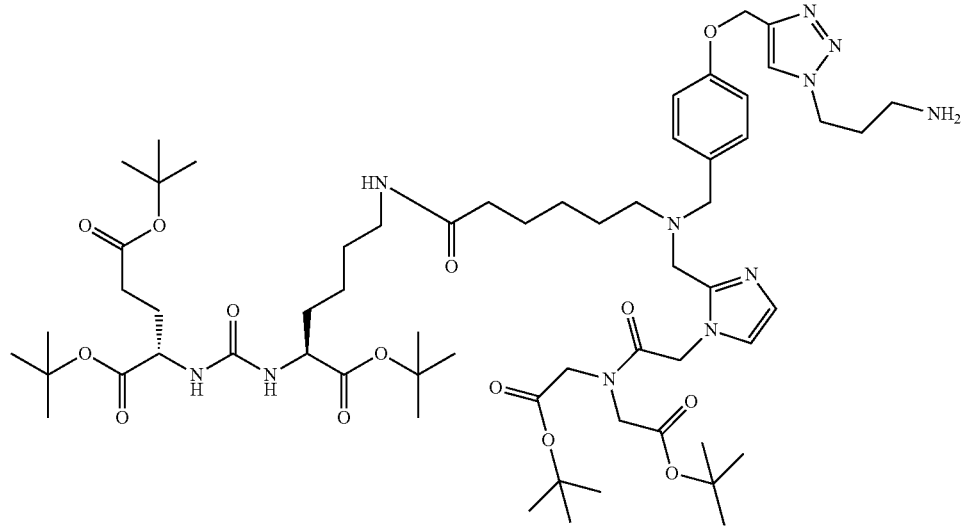 [SMILES: CC(C)(C)OC(=O)CC[C@H](NC(=O)N[C@@H](CCCCNC(=O)CCCCCN(Cc1ccc(OCc2cn(CCCN)nn2)cc1)Cc1nccn1CC(=O)N(CC(=O)OC(C)(C)C)CC(=O)OC(C)(C)C)C(=O)OC(C)(C)C)C(=O)OC(C)(C)C]

To a solution of (14S,18S)-tri-tert-butyl 1-(1-(2-(bis(2-(tert-butoxy)-2-oxoethyl)amino)-2-oxoethyl)-1H-imidazol-2-yl)-8,16-dioxo-2-(4-(prop-2-yn-1-yloxy)benzyl)-2,9,15,17-tetraazaicosane-14,18,20-tricarboxylate (65 mg, 0.0586 mmol) and 3-azidopropan-1-amine (200 mg, 2.0 mmol) in THF (2.0 mL) and water (0.5 mL) was added copper powder (10 mg) and 1 N CuSO$_4$ (0.05 mL). The mixture was stirred at room temperature for 2 h under nitrogen, diluted with DCM and washed with an aqueous saturated solution of EDTA. The solvent was evaporated under reduce pressure to afford a residue, which was purified by Biotage SP4 to afford (14S,18S)-tri-tert-butyl 2-(4-((1-(3-aminopropyl)-1H-1,2,3-triazol-4-yl)methoxy)benzyl)-1-(1-(2-(bis(2-(tert-butoxy)-2-oxoethyl)amino)-2-oxoethyl)-1H-imidazol-2-yl)-8,16-dioxo-2,9,15,17-tetraazaicosane-14,18,20-tricarboxylate (17.5 mg, 25%). MS (ESI), 605.8 (M/2+H)'.

Step 5. ((14S,18S)-1-(1-(2-(bis(carboxymethyl)amino)-2-oxoethyl)-1H-imidazol-2-yl)-8,16-dioxo-2-(4-((1-(3-(2-(4,7,10-tris(carboxymethyl)-1,4,7,10-tetraazacyclododecan-1-yl)acetamido)propyl)-1H-1,2,3-triazol-4-yl)methoxy)benzyl)-2,9,15,17-tetraazaicosane-14,18,20-tricarboxylic acid (MIP-1459)

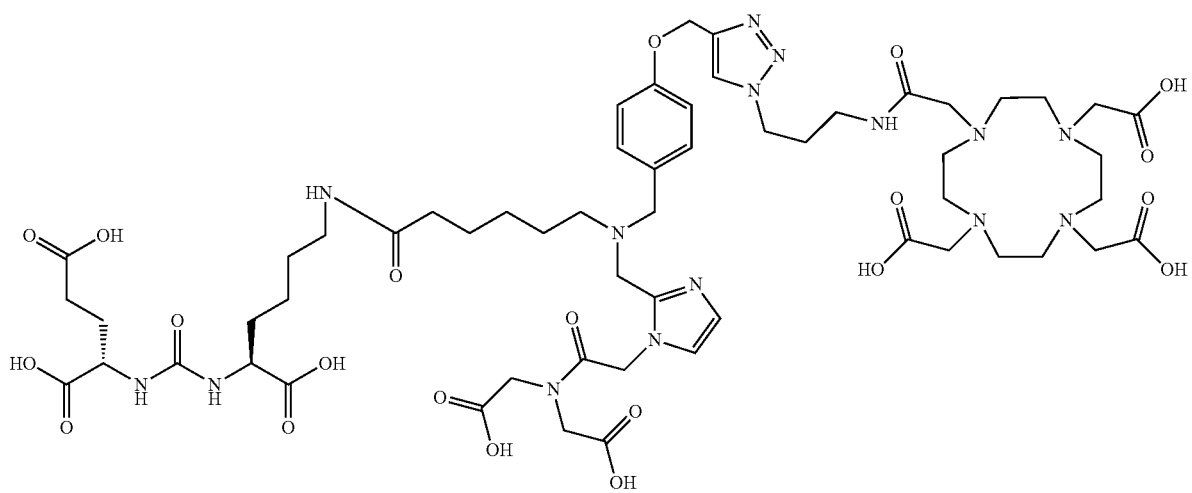 [SMILES: O=C(O)CC[C@H](NC(=O)N[C@@H](CCCCNC(=O)CCCCCN(Cc1ccc(OCc2cn(CCCNC(=O)CN3CCN(CC(=O)O)CCN(CC(=O)O)CCN(CC(=O)O)CC3)nn2)cc1)Cc1nccn1CC(=O)N(CC(=O)O)CC(=O)O)C(=O)O)C(=O)O]

A solution of (14S,18S)-tri-tert-butyl 2-(4-((1-(3-amino-propyl)-1H-1,2,3-triazol-4-yl)methoxy)benzyl)-1-(1-(2-(bis(2-(tert-butoxy)-2-oxoethyl)amino)-2-oxoethyl)-1H-imidazol-2-yl)-8,16-dioxo-2,9,15,17-tetraazaicosane-14,18,20-tricarboxylate (17.5 mg, 0.0145 mmol), 2,2',2''-(10-(2-((2,5-dioxo-2,5-dihydro-1H-pyrrol-1-yl)oxy)-2-oxoethyl)-1,4,7,10-tetraazacyclododecane-1,4,7-triyl)triacetic acid (30 mg, 0.60 mmol) and DIPEA (0.20 mL) in DMF (0.50 mL) was stirred at room temperature for 2 h. The solvent was evaporated to give a residue, to which was added TFA (0.50 mL) and DCM (0.50 mL). The mixture was stirred at rt for 4 h. The solvent was removed under a stream of nitrogen to give a residue, which was purified by HPLC to yield MIP-1459 (10 mg). MS (ESI), 659.0 (M/2+H)$^+$.

Step 6. Synthesis of ((14S,18S)-tri-tert-butyl 1-(1-(2-(bis(2-(tert-butoxy)-2-oxoethyl)amino)-2-oxoethyl)-1H-imidazol-2-yl)-8,16-dioxo-2-(4-((1-(3-(2-(4,7,10-tris(2-(tert-butoxy)-2-oxoethyl)-1,4,7,10-tetraazacyclododecan-1-yl)acetamido)propyl)-1H-1,2,3-triazol-4-yl)methoxy)benzyl)-2,9,15,17-tetraazaicosane-14,18,20-tricarboxylate (MIP-1459 t-butyl estert)

rated under reduce pressure to afford a residue, which was purified by Biotage SP4 to afford ((14S,18S)-tri-tert-butyl 1-(1-(2-(bis(2-(tert-butoxy)-2-oxoethyl)amino)-2-oxoethyl)-1H-imidazol-2-yl)-8,16-dioxo-2-(4-((1-(3-(2-(4,7,10-tris(2-(tert-butoxy)-2-oxoethyl)-1,4,7,10-tetraazacyclododecan-1-yl)acetamido)propyl)-1H-1,2,3-triazol-4-yl)methoxy)benzyl)-2,9,15,17-tetraazaicosane-14,18,20-tricarboxylate (21.8 mg). MS (ESI), 883.2 (M/2+H)'.

Step 7. (14S,18S)-1-(1-(2-(bis(carboxymethyl)amino)-2-oxoethyl)-1H-imidazol-2-yl)-8,16-dioxo-2-(4-((1-(3-(2-(4,7,10-tris(carboxymethyl)-1,4,7,10-tetraazacyclododecan-1-yl)acetamido)propyl)-1H-1,2,3-triazol-4-yl)methoxy)benzyl)-2,9,15,17-tetraazaicosane-14,18,20-tricarboxylic acid Indium complex (MIP-1445)

A solution of ((14S,18S)-tri-tert-butyl 1-(1-(2-(bis(2-(tert-butoxy)-2-oxoethyl)amino)-2-oxoethyl)-1H-imidazol-2-yl)-8,16-dioxo-2-(4-((1-(3-(2-(4,7,10-tris(2-(tert-butoxy)-2-oxoethyl)-1,4,7,10-tetraazacyclododecan-1-yl)acetamido)propyl)-1H-1,2,3-triazol-4-yl)methoxy)benzyl)-2,9,15,17-tetraazaicosane-14,18,20-tricarboxylate (21 mg, 0.012 mmol) in TFA (2.0 mL) and DCM (2.0 mL) was stirred at rt

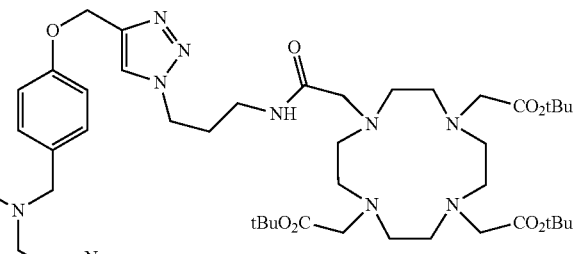
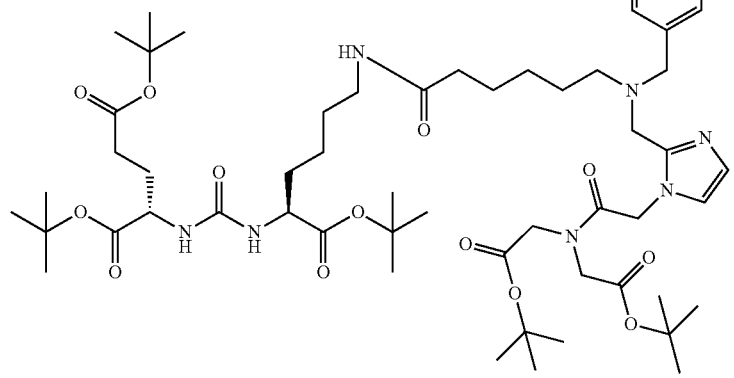

To a solution of (14S,18S)-tri-tert-butyl 1-(1-(2-(bis(2-(tert-butoxy)-2-oxoethyl)amino)-2-oxoethyl)-1H-imidazol-2-yl)-8,16-dioxo-2-(4-(prop-2-yn-1-yloxy)benzyl)-2,9,15,17-tetraazaicosane-14,18,20-tricarboxylate (145 mg, 0.13 mmol), tri-tert-butyl 2,2',2''-(10-(2-((3-azidopropyl)amino)-2-oxoethyl)-1,4,7,10-tetraazacyclododecane-1,4,7-triyl)triacetate (59 mg, 0.090 mmol) in THF (5.0 mL) and water (1.0 mL) was added copper powder (6.4 mg) and 1 N CuSO$_4$ (0.01 mL). The mixture was stirred at room temperature for overnight under nitrogen, diluted with EtOAc, washed with an aqueous saturated solution of EDTA. The solvent was evapoovernight. The solvent was removed under a stream of nitrogen to give a crude ((14S,18S)-1-(1-(2-(bis(carboxymethyl)amino)-2-oxoethyl)-1H-imidazol-2-yl)-8,16-dioxo-2-(4-((1-(3-(2-(4,7,10-tris(carboxymethyl)-1,4,7,10-tetraazacyclododecan-1-yl)acetamido)propyl)-1H-1,2,3-triazol-4-yl)methoxy)benzyl)-2,9,15,17-tetraazaicosane-14,18,20-tricarboxylic acid, (MIP-1459), which was dissolved in ammonium acetate (0.30 mL, 0.50 N) solution in water (0.50 mL) with InCl$_3$ (10 mg). The reaction mixture was heated at 95° C. for 1 h and was purified by HPLC to give the product (MIP-1445, (1 mg)). MS (ESI), 714.9 (M/2+H)$^+$.

Example 2

(14S,18S)-1-(1-(carboxymethyl)-1H-imidazol-2-yl)-8,16-dioxo-2-(4-((1-(3-(2-(4,7,10-tris(carboxymethyl)-1,4,7,10-tetraazacyclododecan-1-yl)acetamido)propyl)-1H-1,2,3-triazol-4-yl)methoxy)benzyl)-2,9,15,17-tetraazaicosane-14,18,20-tricarboxylic acid Indium complex (MIP-1470)

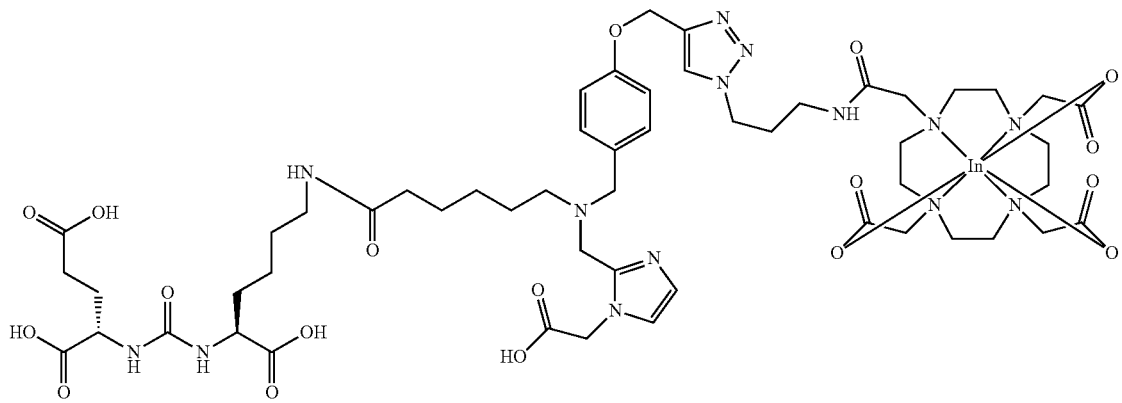

Step 1. 6-(((1-(2-(tert-butoxy)-2-oxoethyl)-1H-imidazol-2-yl)methyl)(4-(prop-2-yn-1-yloxy)benzyl)amino)hexanoic acid Step 2. (14S,18S)-tri-tert-butyl 1-(1-(2-(tert-butoxy)-2-oxoethyl)-1H-imidazol-2-yl)-8,16-dioxo-2-(4-(prop-2-yn-1-yloxy)benzyl)-2,9,15,17-tetraazaicosane-14,18,20-tricarboxylate

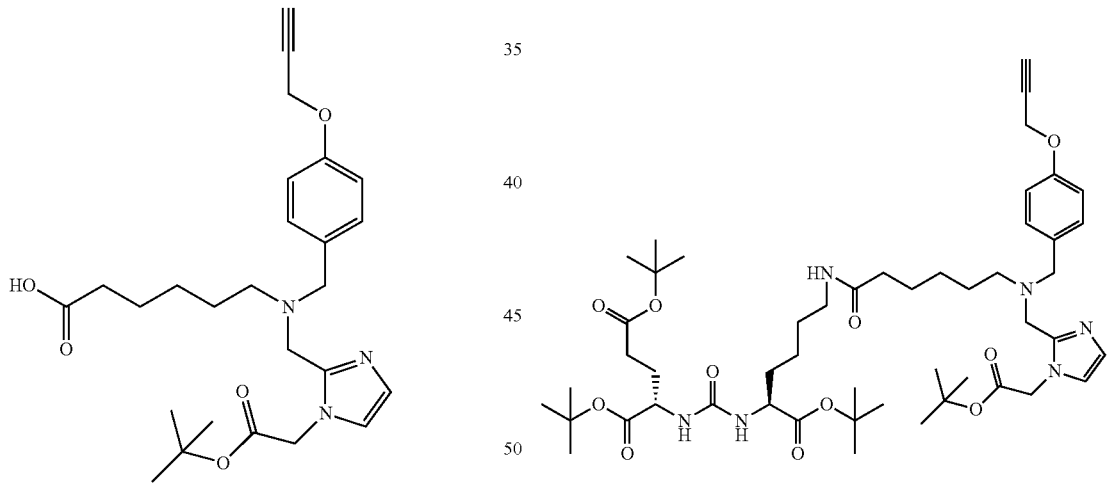

A solution of 6-((4-(prop-2-yn-1-yloxy)benzyl)amino)hexanoic acid (0.4125 g, 1.50 mmol), tert-butyl 2-(2-formyl-1H-imidazol-1-yl)acetate (0.315 g, 1.50 mmol) and AcOH (0.05 mL) in DCE (40 mL) at 0° C. was treated with NaBH(OAc)₃ (0.636 g, 3.0 mmol). The reaction mixture was stirred at 0° C. for 30 min and at room temperature for overnight and decomposed with water and methanol. The reaction mixture was concentrated under reduced pressure to give a residue, which was purified by Biotage SP4 over silica gel to afford 6-(((1-(2-(tert-butoxy)-2-oxoethyl)-1H-imidazol-2-yl)methyl)(4-(prop-2-yn-1-yloxy)benzyl)amino)hexanoic acid (0.268 g, 38%). MS (ESI), 470.3 (M+H)⁺.

A solution of (S)-di-tert-butyl 2-(3-((S)-6-amino-1-(tert-butoxy)-1-oxohexan-2-yl)ureido)pentanedioate (0.480 g, 1.0 mmol), 6-(((1-(2-(tert-butoxy)-2-oxoethyl)-1H-imidazol-2-yl)methyl)(4-(prop-2-yn-1-yloxy)benzyl)amino)hexanoic acid (0.220 g, 0.468 mmol), EDCI (0.191 g, 1.0 mmol), HOBt (0.135 g, 1.0 mmol) and DIPEA (0.40 mL) in DCE (10.0 mL) was stirred at room temperature for 3 h. The solvent was evaporated to give a residue, which was purified by Biotage eluting with DCM/MeOH to give (14S,18S)-tri-tert-butyl 1-(1-(2-(tert-butoxy)-2-oxoethyl)-1H-imidazol-2-yl)-8,16-dioxo-2-(4-(prop-2-yn-1-yloxy)benzyl)-2,9,15,17-tetraazaicosane-14,18,20-tricarboxylate (0.251 g, 57%). MS (ESI), 939.5 (M+H)⁺.

Step 3. (14S,18S)-tri-tert-butyl 2-(4-((1-(3-amino-propyl)-1H-1,2,3-triazol-4-yl)methoxy)benzyl)-1-(1-(2-(tert-butoxy)-2-oxoethyl)-1H-imidazol-2-yl)-8,16-dioxo-2,9,15,17-tetraazaicosane-14,18,20-tricarboxylate

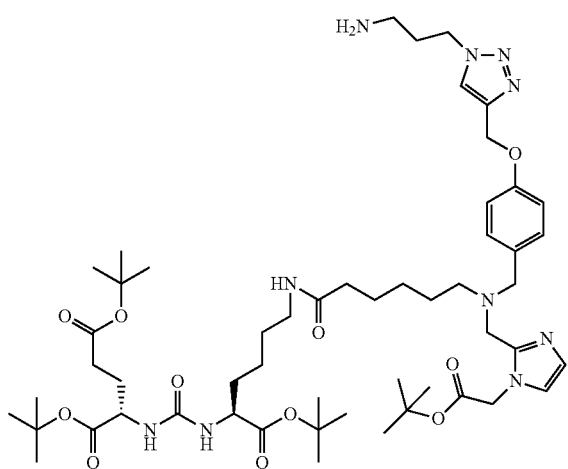 [SMILES: CC(C)(C)OC(=O)CC[C@H](NC(=O)N[C@@H](CCCCNC(=O)CCCCCN(Cc1ccc(OCc2cn(CCCN)nn2)cc1)Cc1nccn1CC(=O)OC(C)(C)C)C(=O)OC(C)(C)C)C(=O)OC(C)(C)C]

To a solution of (14S,18S)-tri-tert-butyl 1-(1-(2-(tert-butoxy)-2-oxoethyl)-1H-imidazol-2-yl)-8,16-dioxo-2-(4-(prop-2-yn-1-yloxy)benzyl)-2,9,15,17-tetraazaicosane-14,18,20-tricarboxylate (250 mg, 0.266 mmol) and 3-azidopropan-1-amine (200 mg, 2.0 mmol) in THF (5.0 mL) and water (1.0 mL) was added copper powder (17 mg) and 1 N CuSO₄ (0.05 mL). The mixture was stirred at room temperature for 6 hrs under nitrogen, diluted with DCM, washed with aqueous saturated solution of EDTA. The solvent was evaporated under reduce pressure to afford a residue, which was purified by Biotage SP4 to afford (14S,18S)-tri-tert-butyl 2-(4-((1-(3-aminopropyl)-1H-1,2,3-triazol-4-yl)methoxy)benzyl)-1-(1-(2-(tert-butoxy)-2-oxoethyl)-1H-imidazol-2-yl)-8,16-dioxo-2,9,15,17-tetraazaicosane-14,18,20-tricarboxylate (158 mg, 57%) as a yellow oil. MS (ESI), 520.4 (M/2+H)⁺.

Step 4. (14S,18S)-1-(1-(carboxymethyl)-1H-imidazol-2-yl)-8,16-dioxo-2-(4-((1-(3-(2-(4,7,10-tris(carboxymethyl)-1,4,7,10-tetraazacyclododecan-1-yl)acetamido)propyl)-1H-1,2,3-triazol-4-yl)methoxy)benzyl)-2,9,15,17-tetraazaicosane-14,18,20-tricarboxylic acid (MIP-1469)

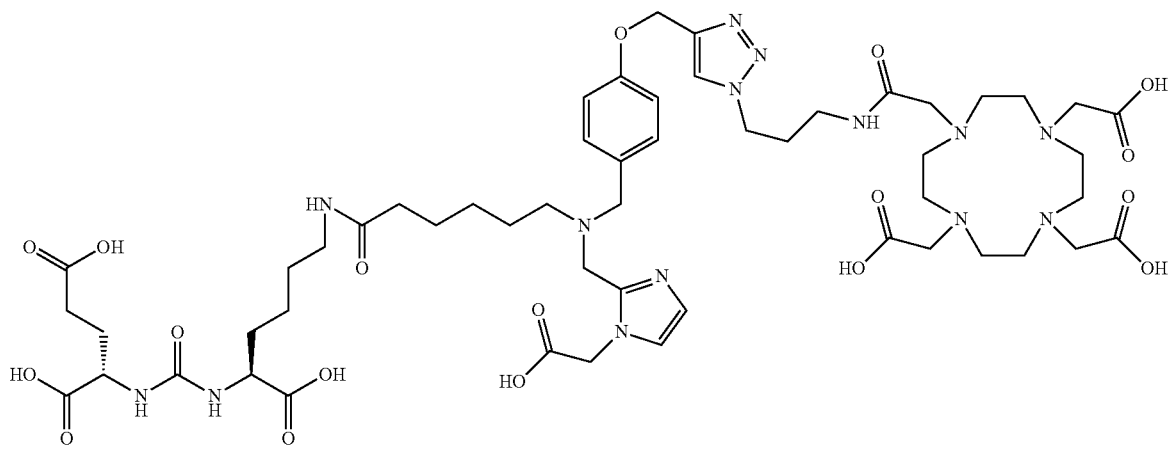 [SMILES: O=C(O)CC[C@H](NC(=O)N[C@@H](CCCCNC(=O)CCCCCN(Cc1ccc(OCc2cn(CCCNC(=O)CN3CCN(CC(=O)O)CCN(CC(=O)O)CCN(CC(=O)O)CC3)nn2)cc1)Cc1nccn1CC(=O)O)C(=O)O)C(=O)O]

A solution of (14S,18S)-tri-tert-butyl 2-(4-((1-(3-aminopropyl)-1H-1,2,3-triazol-4-yl)methoxy)benzyl)-1-(1-(2-(tert-butoxy)-2-oxoethyl)-1H-imidazol-2-yl)-8,16-dioxo-2,9,15,17-tetraazaicosane-14,18,20-tricarboxylate (148 mg, 0.143 mmol), 2,2',2''-(10-(2-((2,5-dioxo-2,5-dihydro-1H-pyrrol-1-yl)oxy)-2-oxoethyl)-1,4,7,10-tetraazacyclododecane-1,4,7-triyl)triacetic acid (71 mg, 0.143 mmol) and DIPEA (0.30 mL) in DMF (3.0 mL) was stirred at room temperature for overnight. The solvent was evaporated to give a residue, which was added TFA (3.0 mL) and DCM (3.0 mL). The mixture was stirred at rt overnight. The solvent was removed under a stream of nitrogen to give a residue, which was purified by HPLC to give MIP-1467 (33.4 mg) as a white solid. MS (ESI), 601.4 (M/2+H)⁺.

Step 5. (14S,18S)-1-(1-(carboxymethyl)-1H-imidazol-2-yl)-8,16-dioxo-2-(4-((1-(3-(2-(4,7,10-tris(carboxymethyl)-1,4,7,10-tetraazacyclododecan-1-yl)acetamido)propyl)-1H-1,2,3-triazol-4-yl)methoxy)benzyl)-2,9,15,17-tetraazaicosane-14,18,20-tricarboxylic acid Indium complex (MIP-1470)

To a solution of (14S,18S)-1-(1-(carboxymethyl)-1H-imidazol-2-yl)-8,16-dioxo-2-(4-((1-(3-(2-(4,7,10-tris(carboxymethyl)-1,4,7,10-tetraazacyclododecan-1-yl)acetamido)propyl)-1H-1,2,3-triazol-4-yl)methoxy)benzyl)-2,9,15,17-tetraazaicosane-14,18,20-tricarboxylic acid (14.3 mg, 0.0119) and ammonium acetate (1.0 mL, 0.50 N) in water (2.0 mL) was added InCl₃ (9 mg). The reaction mixture was heated at 100° C. for 45 min and was purified by HPLC to give MIP-1470 (2.9 mg). MS (ESI), 657.2 (M/2+H)⁺.

Example 3

(8S,15S,19S)-8-amino-2,9,17-trioxo-1-(4,7,10-tris(carboxymethyl)-1,4,7,10-tetraazacyclododecan-1-yl)-3,10,16,18-tetraazahenicosane-15,19,21-tricarboxylic acid Indium complex (MIP-1458)

A solution of (S)-di-tert-butyl 2-(3-((S)-6-amino-1-(tert-butoxy)-1-oxohexan-2-yl)ureido)pentanedioate (0.048 g, 0.10 mmol), (S)-2-(((((9H-fluoren-9-yl)methoxy)carbonyl)amino)-6-(2-(4,7,10-tris(2-(tert-butoxy)-2-oxoethyl)-1,4,7,10-tetraazacyclododecan-1-yl)acetamido)hexanoic acid (56 mg, 0.0607 mmol), EDCI (19 mg, 0.10 mmol), HOBt (13.5 mg, 0.10 mmol) and DIPEA (0.10 mL) in DCM (5.0 mL) was stirred at room temperature for 2 hrs. The solvent was evaporated to give a residue, which was purified by Biotage eluting with DCM to 10% MeOH in DCM to give (5S,12S,16S)-tri-tert-butyl 1-(9H-fluoren-9-yl)-3,6,14-trioxo-5-(4-(2-(4,7,10-tris(2-(tert-butoxy)-2-oxo ethyl)-1,4,7,10-tetraazacyclododecan-1-yl)acetamido)butyl)-2-oxa-4,7,13,15-tetraazaoctadecane-12,16,18-tricarboxylate (115 mg) containing some impurity. MS (ESI), 697.0 (M+H)⁺.

To a solution of (5S,12S,16S)-tri-tert-butyl 1-(9H-fluoren-9-yl)-3,6,14-trioxo-5-(4-(2-(4,7,10-tris(2-(tert-butoxy)-2-oxoethyl)-1,4,7,10-tetraazacyclododecan-1-yl)acetamido)butyl)-2-oxa-4,7,13,15-tetraazaoctadecane-12,16,18-tricarboxylate (115 mg) containing some impurity in DMF (0.30 mL) and piperidine (0.30 mL) was stirred at rt for 1 hr. Solvents were evaporated under reduced pressure to give a residue, which was purified by Biotage eluting with DCM to 10% MeOH in DCM to give (8S,15S,19S)-tri-tert-butyl 8-amino-2,9,17-trioxo-1-(4,7,10-tris(2-(tert-butoxy)-2-oxoethyl)-1,4,7,10-tetraazacyclododecan-1-yl)-3,10,16,18-tetraazahenicosane-15,19,21-tricarboxylate (64 mg, 90%) as a colorless oil. MS (ESI), 1171.6 (M+H)⁺.

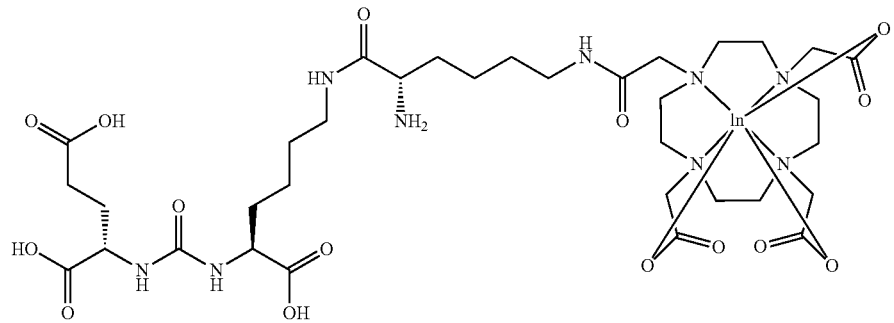

Step 1. (8S,15S,19S)-tri-tert-butyl 8-amino-2,9,17-trioxo-1-(4,7,10-tris(2-(tert-butoxy)-2-oxoethyl)-1,4,7,10-tetraazacyclododecan-1-yl)-3,10,16,18-tetraazahenicosane-15,19,21-tricarboxylate

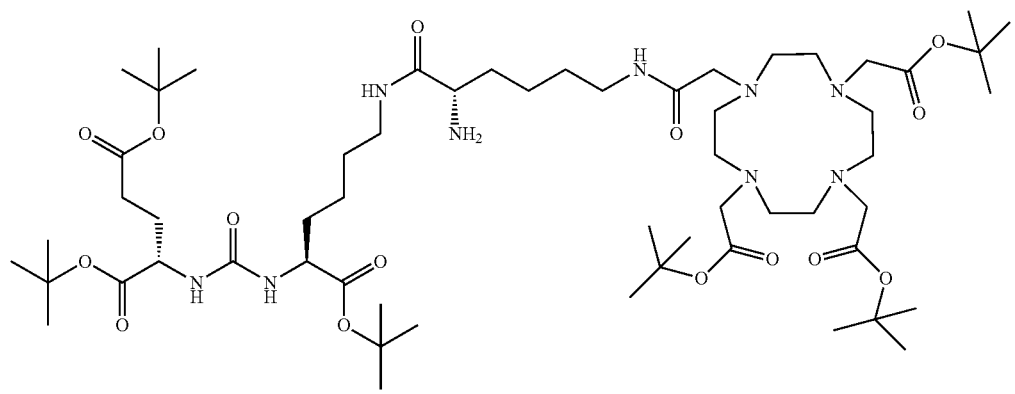 [SMILES: CC(C)(C)OC(=O)CC[C@H](NC(=O)N[C@@H](CCCCNC(=O)[C@@H](N)CCCCNC(=O)CN1CCN(CC(=O)OC(C)(C)C)CCN(CC(=O)OC(C)(C)C)CCN(CC(=O)OC(C)(C)C)CC1)C(=O)OC(C)(C)C)C(=O)OC(C)(C)C]

Step 2. (8S,15S,19S)-8-amino-2,9,17-trioxo-1-(4,7,10-tris(carboxymethyl)-1,4,7,10-tetraazacyclododecan-1-yl)-3,10,16,18-tetraazahenicosane-15,19,21-tricarboxylic acid (MIP-1457)

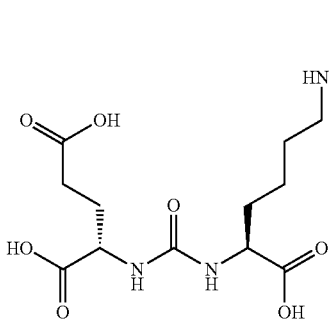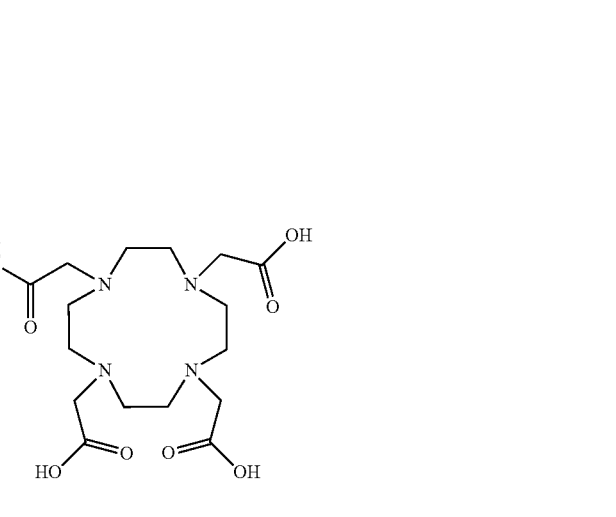

A solution of ((8R,15S,19S)-tri-tert-butyl 8-amino-2,9,17-trioxo-1-(4,7,10-tris(2-(tert-butoxy)-2-oxoethyl)-1,4,7,10-tetraazacyclododecan-1-yl)-3,10,16,18-tetraazahenicosane-15,19,21-tricarboxylate (64 mg) in TFA (1.0 mL) and DCM (1.0 mL) was stirred at rt for overnight. The solvent was removed under a stream of nitrogen to give crude (8S,15S,19S)-8-amino-2,9,17-trioxo-1-(4,7,10-tris(carboxymethyl)-1,4,7,10-tetraazacyclododecan-1-yl)-3,10,16,18-tetraazahenicosane-15,19,21-tricarboxylic acid (57.9 mg). A small amount (9 mg) crude product was purified by HPLC to give pure (8S,15S,19S)-8-amino-2,9,17-trioxo-1-(4,7,10-tris(carboxymethyl)-1,4,7,10-tetraazacyclododecan-1-yl)-3,10,16,18-tetraazahenicosane-15,19,21-tricarboxylic acid (MIP-1457, (2.7 mg)) as a white solid. MS (ESI), 832.2 (M−H)⁻.

Step 3. (8S,15S,19S)-8-amino-2,9,17-trioxo-1-(4,7,10-tris(carboxymethyl)-1,4,7,10-tetraazacyclododecan-1-yl)-3,10,16,18-tetraazahenicosane-15,19,21-tricarboxylic acid Indium complex (MIP-1458)

To a solution of (8S,15S,19S)-8-amino-2,9,17-trioxo-1-(4,7,10-tris(carboxymethyl)-1,4,7,10-tetraazacyclododecan-1-yl)-3,10,16,18-tetraazahenicosane-15,19,21-tricarboxylic acid (18 mg) and ammonium acetate (0.50 mL, 0.50 N) in water (2.0 mL) was added InCl₃ (9 mg). The reaction mixture was heated at 100° C. for 45 min and was purified by HPLC to give the titled product (MIP-1458, (4.0 mg)). MS (ESI), 946.4 (M+H)⁺.

Example 4

Synthesis of (16S,20S)-10,18-dioxo-1-((4-((1,4,7,10-tetrakis(carboxymethyl)-1,4,7,10-tetraazacyclododecan-2-yl)methyl)phenyl)amino)-1-thioxo-2,11,17,19-tetraazadocosane-16,20,22-tricarboxylic acid (MIP-1512)

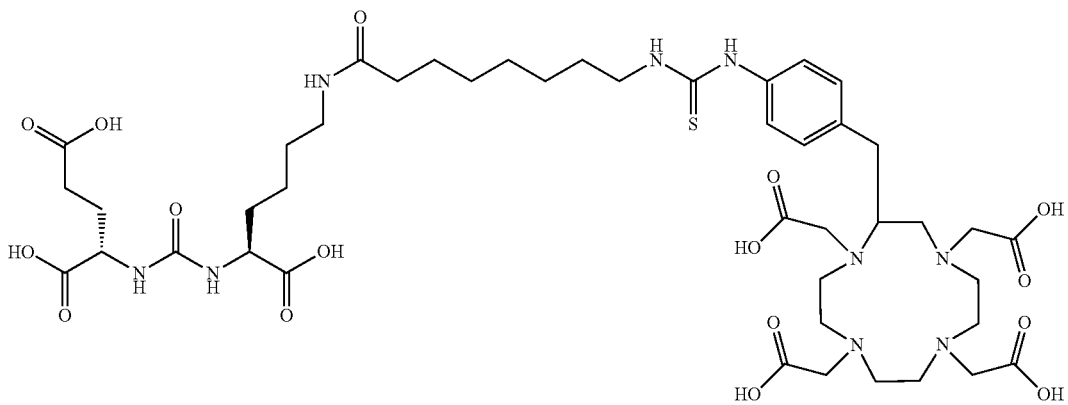 [SMILES: O=C(O)CC[C@H](NC(=O)N[C@@H](CCCCNC(=O)CCCCCCCNC(=S)Nc1ccc(CC2CN(CC(=O)O)CCN(CC(=O)O)CCN(CC(=O)O)CCN2CC(=O)O)cc1)C(=O)O)C(=O)O]

Electrospray ionisation mass spectral analysis: [MS (ESI)]: (M+H)⁺=1013.

Example 5

Synthesis of (16S,20S)-10,18-dioxo-1-((4-((1,4,7,10-tetrakis(carboxymethyl)-1,4,7,10-tetraazacyclododecan-2-yl)methyl)phenyl)amino)-1-thioxo-2,11,17,19-tetraazadocosane-16,20,22-tricarboxylate Lu complex (Lu-MIP-1512)

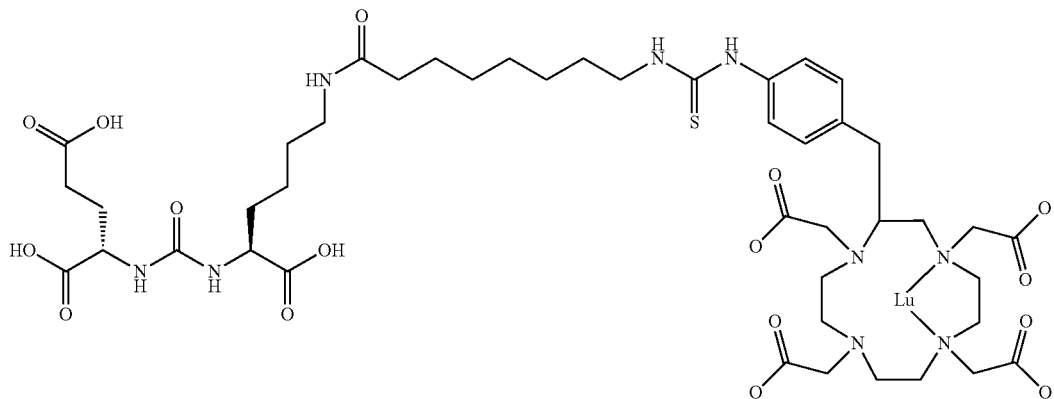

Electrospray ionisation mass spectral analysis: [MS (ESI)]: $(M+H)^+ = 1182$.

Example 6

Synthesis of (10S,17S,21S)-10-(2-carboxyethyl)-8,11,19-trioxo-1-((4-((1,4,7,10-tetrakis(carboxymethyl)-1,4,7,10-tetraazacyclododecan-2-yl)methyl)phenyl)amino)-1-thioxo-2,9,12,18,20-pentaazatricosane-17,21,23-tricarboxylic acid (MIP-1523) was carried out as illustrated in Scheme 5 above

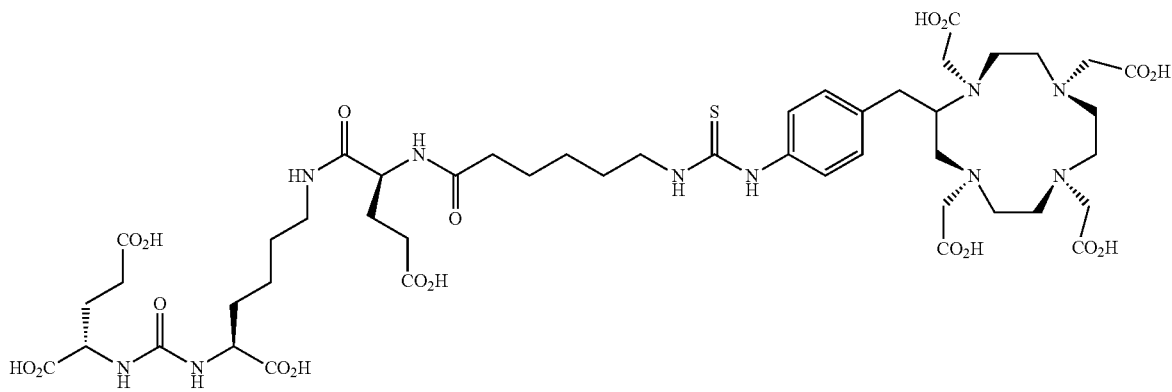

[MS (ESI)]: $(M+H)^+ = 1114$.

Example 7

Synthesis of (10S,17S,21S)-10-(2-carboxyethyl)-8,11,19-trioxo-1-((4-((1,4,7,10-tetrakis(carboxymethyl)-1,4,7,10-tetraazacyclododecan-2-yl)methyl)phenyl)amino)-1-thioxo-2,9,12,18,20-pentaazatricosane-17,21,23-tricarboxylate Lu complex (Lu-MIP-1523) was carried out as illustrated in Scheme 5 above

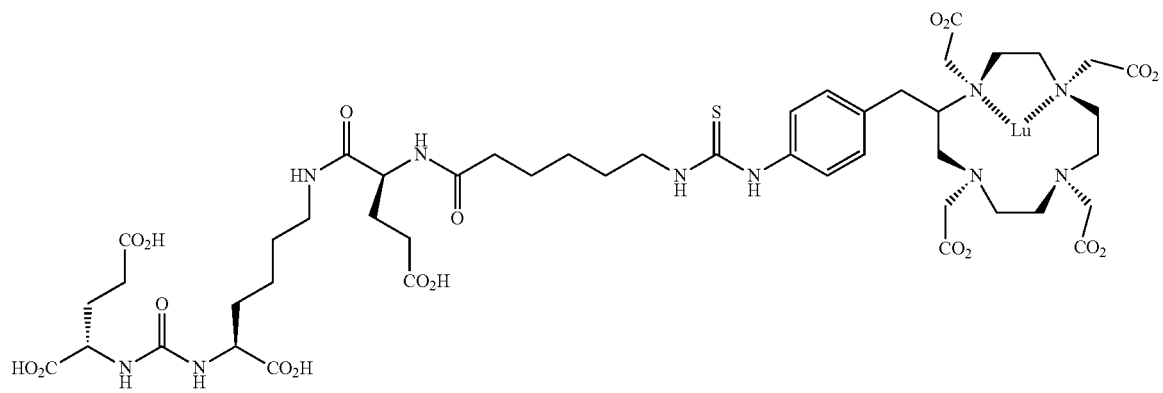

[MS (ESI)]: (M+H)⁺=1285.

Example 8

Synthesis of (10S,17S,21S)-10-benzyl-8,11,19-trioxo-1-((4-((1,4,7,10-tetrakis(carboxymethyl)-1,4,7,10-tetraazacyclododecan-2-yl)methyl)phenyl)amino)-1-thioxo-2,9,12,18,20-pentaazatricosane-17,21,23-tricarboxylic acid (MIP-1530)

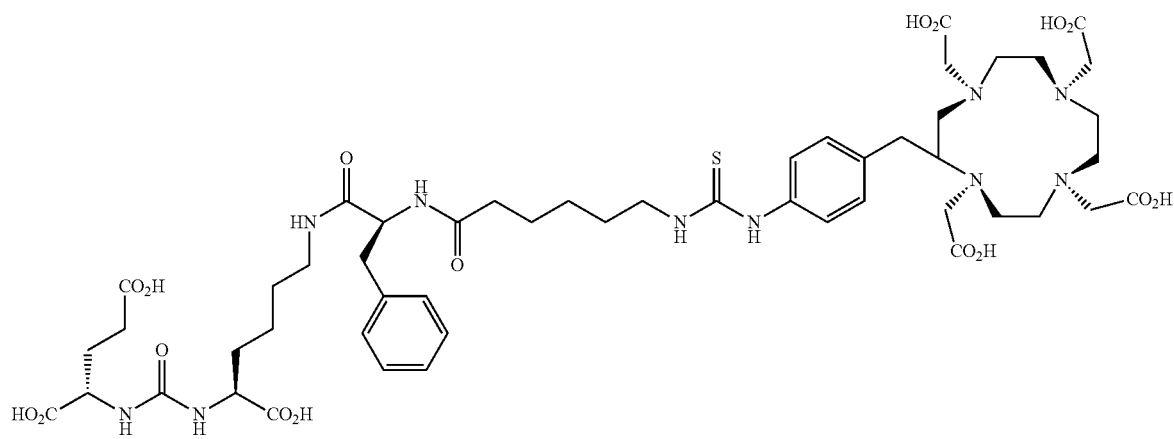

[MS (ESI)]: (M+H)⁺=1132.

Example 9

Synthesis of (10S,17S,21S)-10-benzyl-8,11,19-trioxo-1-((4-(((1,4,7,10-tetrakis(carboxymethyl)-1,4,7,10-tetraazacyclododecan-2-yl)methyl)phenyl)amino)-1-thioxo-2,9,12,18,20-pentaazatricosane-17,21,23-tricarboxylate-Lu complex (Lu-MIP-1530)

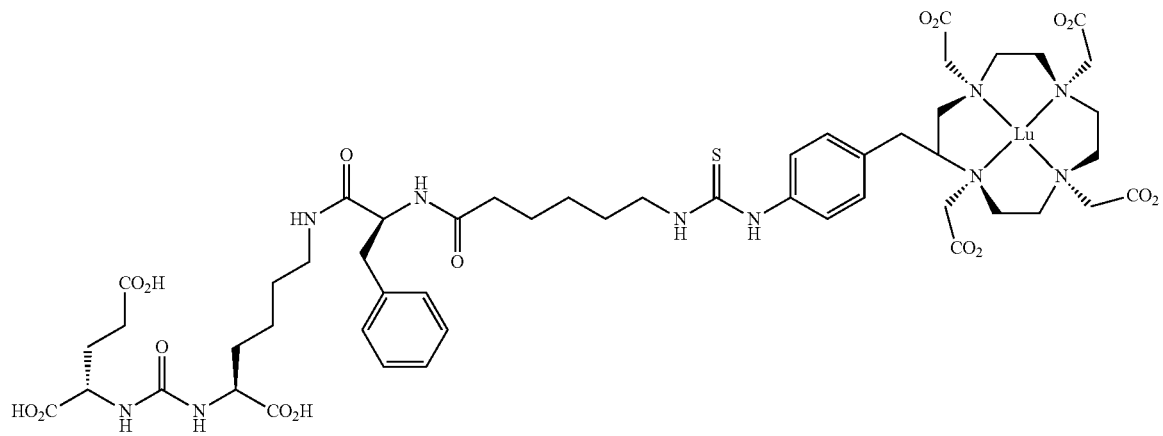

[MS (ESI)]: (M+H)$^+$=1303 (M+H)$^+$.

Example 10

Synthesis of (3S,7S,14S,17S)-14-benzyl-5,13,16-trioxo-17-(6-(3-(4-(((S)-1,4,7,10-tetrakis(carboxymethyl)-1,4,7,10-tetraazacyclododecan-2-yl)methyl)phenyl)thioureido)hexanamido)-4,6,12,15-tetraazanonadecane-1,3,7,19-tetracarboxylic acid (MIP-1531)

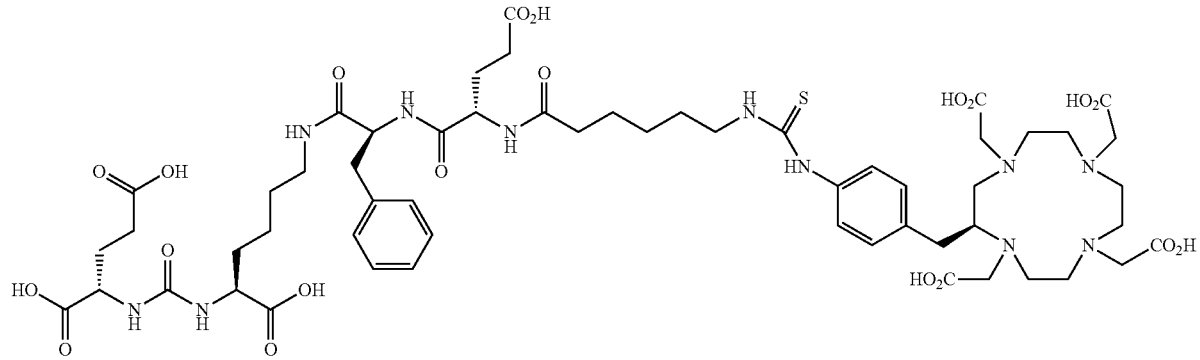 [SMILES: O=C(O)CC[C@H](NC(=O)N[C@@H](CCCCNC(=O)[C@H](Cc1ccccc1)NC(=O)[C@H](CCC(=O)O)NC(=O)CCCCCNC(=S)Nc1ccc(C[C@H]2CN(CC(=O)O)CCN(CC(=O)O)CCN(CC(=O)O)CCN2CC(=O)O)cc1)C(=O)O)C(=O)O]

[MS (ESI)]: (M+H)$^+$=1261.

Example 11

Synthesis of (3S,7S,14S,17S)-14-benzyl-5,13,16-trioxo-17-(6-(3-(4-(((S)-1,4,7,10-tetrakis(carboxymethyl)-1,4,7,10-tetraazacyclododecan-2-yl)methyl)phenyl)thioureido)hexanamido)-4,6,12,15-tetraazanonadecane-1,3,7,19-tetracarboxylate Lu complex (Lu-MIP-1531)

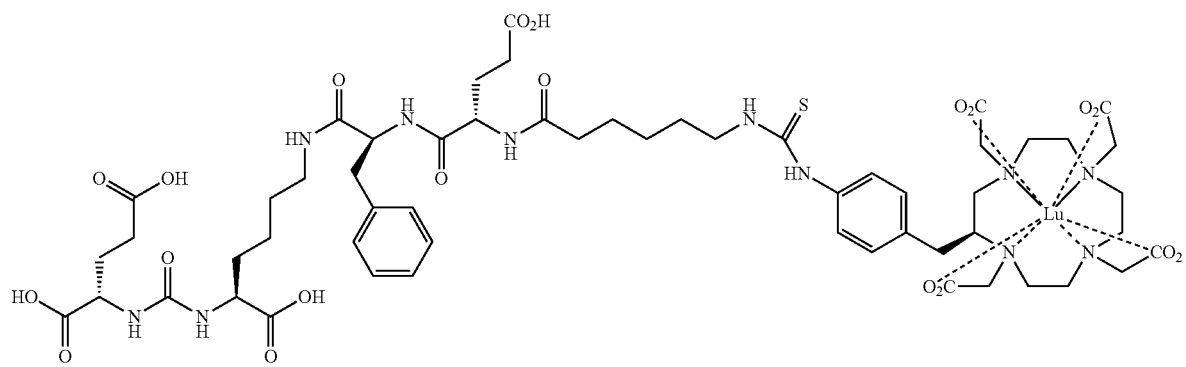

[MS (ESI)]: (M+H)$^+$=1432.

Example 12

Synthesis of (10S,17S,21S)-10-(4-fluorobenzyl)-8,11,19-trioxo-1-((4-((1,4,7,10-tetrakis(carboxymethyl)-1,4,7,10-tetraazacyclododecan-2-yl)methyl)phenyl)amino)-1-thioxo-2,9,12,18,20-pentaazatricosane-17,21,23-tricarboxylic acid (MIP-1546) was carried out as illustrated in Scheme 6 above.

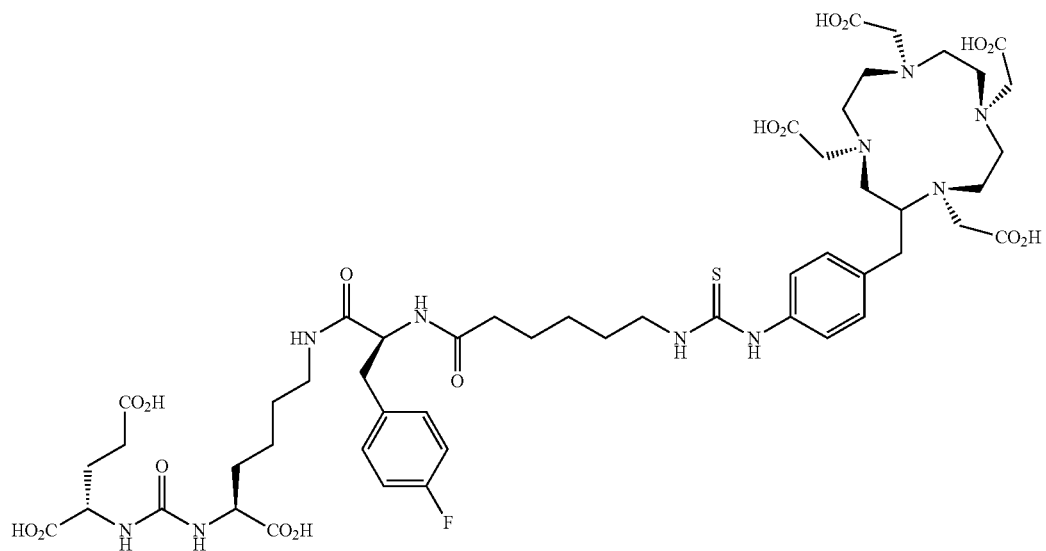

[MS (ESI)]: (M+H)$^+$=1150.

Example 13

Synthesis of (10S,17S,21S)-10-(4-fluorobenzyl)-8,11,19-trioxo-1-((4-((1,4,7,10-tetrakis(carboxymethyl)-1,4,7,10-tetraazacyclododecan-2-yl)methyl)phenyl)amino)-1-thioxo-2,9,12,18,20-pentaazatricosane-17,21,23-tricarboxylate Lu complex (Lu-MIP-1546) was carried out as illustrated in Scheme 6 above

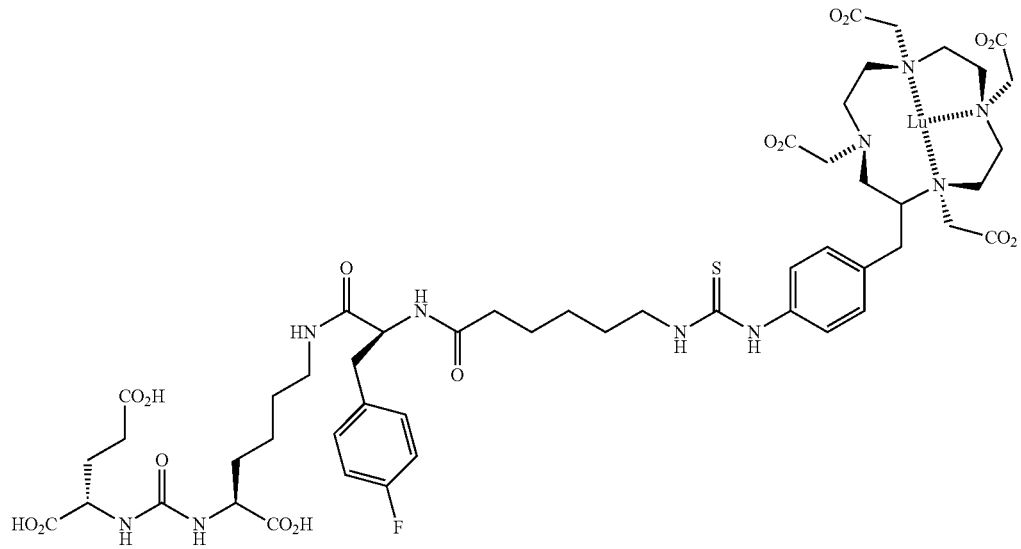

[MS (ESI)]: (M+H)$^+$=1321.

Example 14

Synthesis of (10S,17S,21S)-10-(naphthalen-2-ylmethyl)-8,11,19-trioxo-1-((4-((1,4,7,10-tetrakis(carboxymethyl)-1,4,7,10-tetraazacyclododecan-2-yl)methyl)phenyl)amino)-1-thioxo-2,9,12,18,20-pentaazatricosane-17,21,23-tricarboxylic acid (MIP-1545)

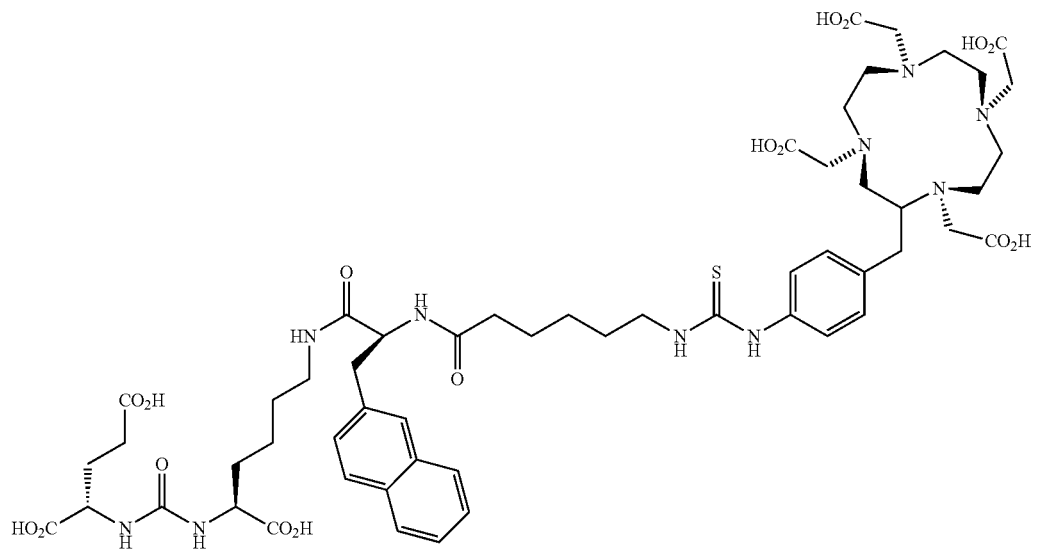

[MS (ESI)]: (M+H)$^+$=1182.

Example 15

Synthesis of (10S,17S,21S)-10-(naphthalen-2-ylmethyl)-8,11,19-trioxo-1-((4-((1,4,7,10-tetrakis(carboxymethyl)-1,4,7,10-tetraazacyclododecan-2-yl)methyl)phenyl)amino)-1-thioxo-2,9,12,18,20-pentaazatricosane-17,21,23-tricarboxylate Lu complex (Lu-MIP-1545)

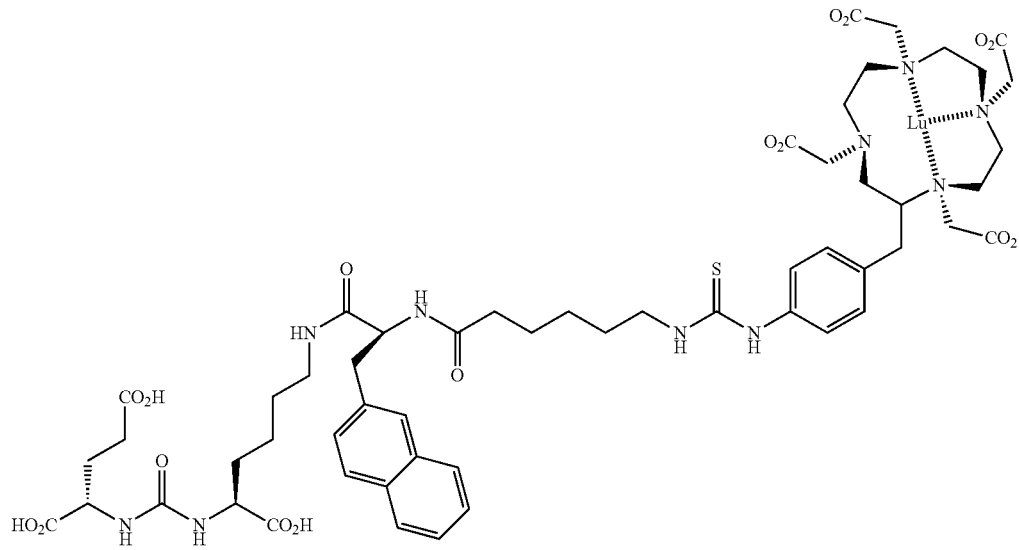

[MS (ESI)]: (M+H)$^+$=1352.

Example 16

Synthesis of (10S,13S,20S,24S)-13-(2-carboxyethyl)-10-(4-fluorobenzyl)-8,11,14,22-tetraoxo-1-((4-((1,4,7,10-tetrakis(carboxymethyl)-1,4,7,10-tetraazacyclododecan-2-yl)methyl)phenyl)amino)-1-thioxo-2,9,12,15,21,23-hexaazahexacosane-20,24,26-tricarboxylic acid (MIP-1550) was carried out as illustrated in Scheme 7 above.

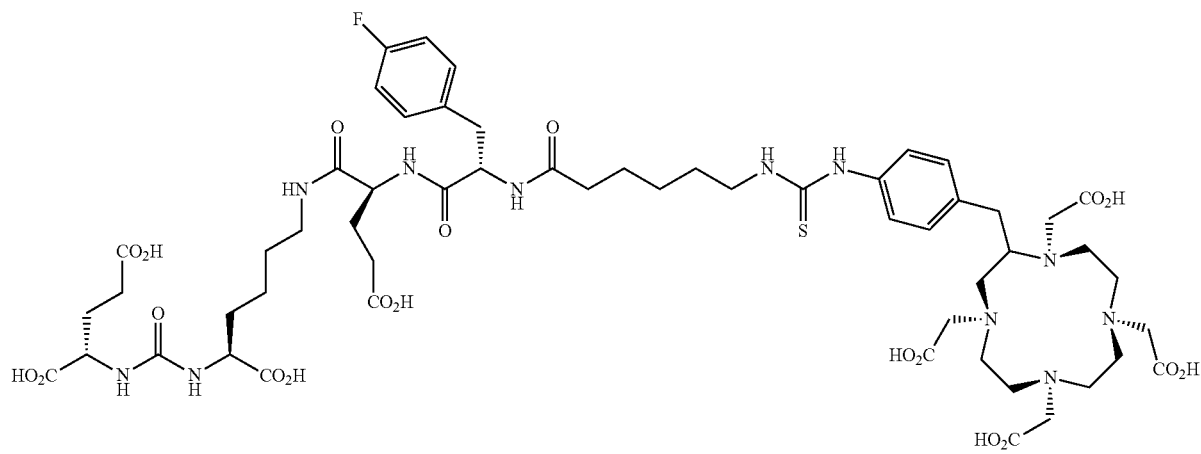

[MS (ESI)]: (M+H)$^+$=1279.

Example 17

Synthesis of (10S,13S,20S,24S)-13-(2-carboxyethyl)-10-(4-fluorobenzyl)-8,11,14,22-tetraoxo-1-((4-(((1,4,7,10-tetrakis(carboxymethyl)-1,4,7,10-tetraazacyclododecan-2-yl)methyl)phenyl)amino)-1-thioxo-2,9,12,15,21,23-hexaazahexacosane-20,24,26-tricarboxylate Lu complex (Lu-MIP-1550) was carried out as illustrated in Scheme 7 above

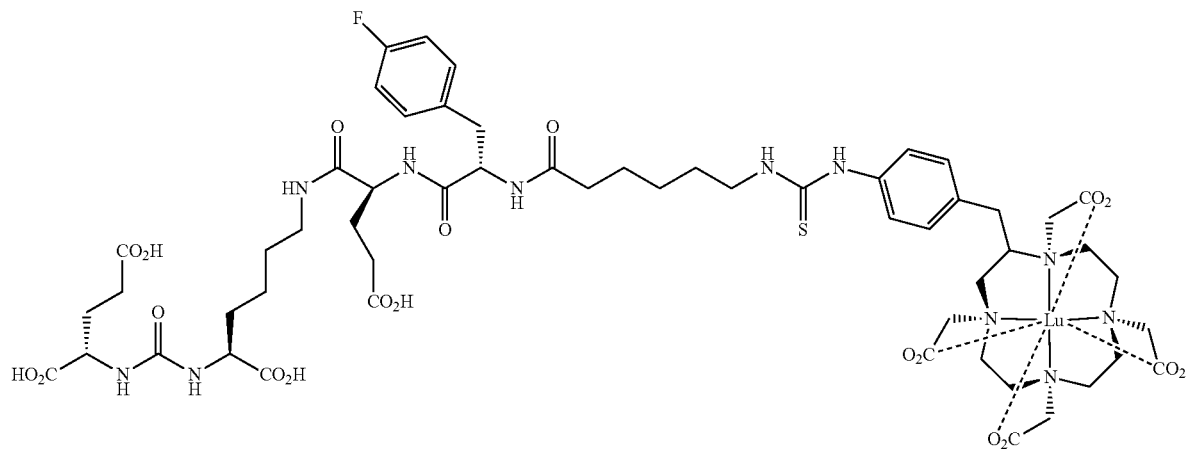

[MS (ESI)]: $(M+H)^+ = 1450$.

Example 18

Synthesis of (11S,16S,20S)-11-(2-carboxyethyl)-10,13,18-trioxo-1-((4-(((1,4,7,10-tetrakis(carboxymethyl)-1,4,7,10-tetraazacyclododecan-2-yl)methyl)phenyl)amino)-1-thioxo-2,9,12,17,19-pentaazadocosane-16,20,22-tricarboxylic acid (MIP-1519)

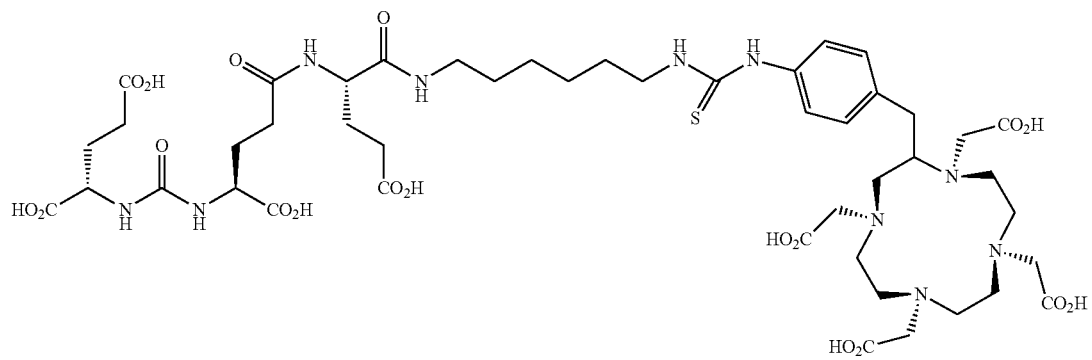

[MS (ESI)]: $(M+H)^+ = 1100$.

Example 19

Synthesis of (11S,16S,20S)-11-(2-carboxyethyl)-10,13,18-trioxo-1-((4-((1,4,7,10-tetrakis(carboxymethyl)-1,4,7,10-tetraazacyclododecan-2-yl)methyl)phenyl)amino)-1-thioxo-2,9,12,17,19-pentaazadocosane-16,20,22-tricarboxylate Lu complex (Lu-MIP-1519)

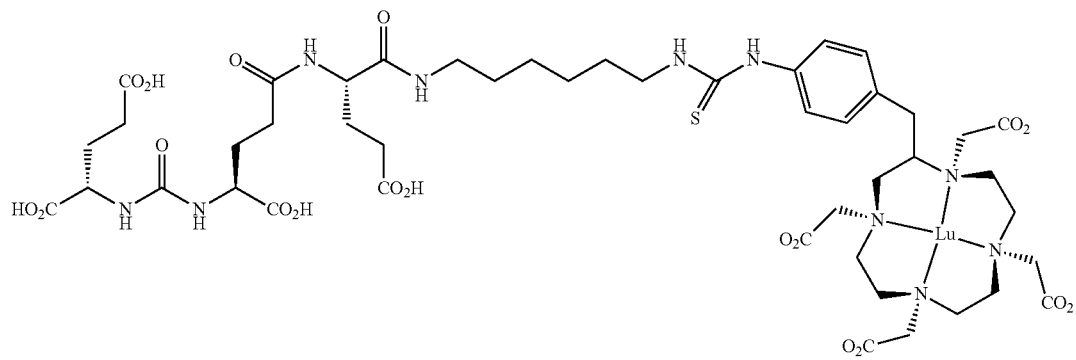

[MS (ESI)]: (M+H)$^+$=1271.

Example 20

Synthesis of (13S,17S)-10,15-dioxo-1-((4-((1,4,7,10-tetrakis(carboxymethyl)-1,4,7,10-tetraazacyclododecan-2-yl)methyl)phenyl)amino)-1-thioxo-2,9,14,16-tetraazanonadecane-13,17,19-tricarboxylic acid (MIP-1526)

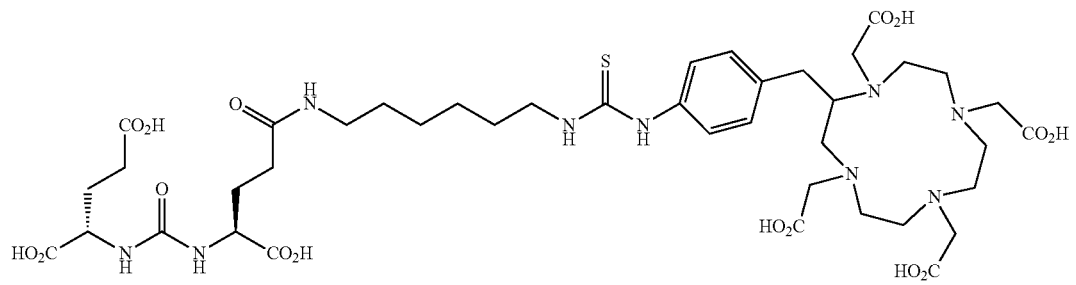 [SMILES: O=C(O)CC[C@H](NC(=O)N[C@@H](CCC(=O)NCCCCCCNC(=S)Nc1ccc(CC2CN(CC(=O)O)CCN(CC(=O)O)CCN(CC(=O)O)CCN2CC(=O)O)cc1)C(=O)O)C(=O)O]

[MS (ESI)]: (M+H)$^+$=970.

Example 21
Synthesis of (13S,17S)-10,15-dioxo-1-((4-((1,4,7,10-tetrakis(carboxymethyl)-1,4,7,10-tetraazacyclododecan-2-yl)methyl)phenyl)amino)-1-thioxo-2,9,14,16-tetraazanonadecane-13,17,19-tricarboxylate Lu complex (Lu-MIP-1526)
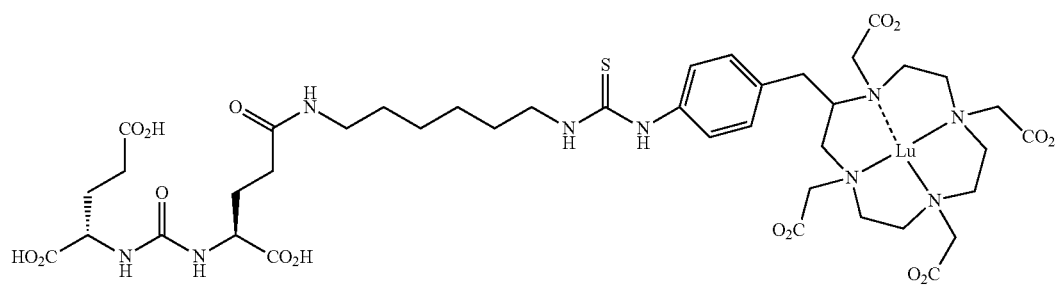
[MS (ESI)]: $(M+H)^+ = 1142$.
Example 22
Synthesis of (11S,16S,20S)-11-benzyl-10,13,18-trioxo-1-((4-((1,4,7,10-tetrakis(carboxymethyl)-1,4,7,10-tetraazacyclododecan-2-yl)methyl)phenyl)amino)-1-thioxo-2,9,12,17,19-pentaazadocosane-16,20,22-tricarboxylic acid (MIP-1548)
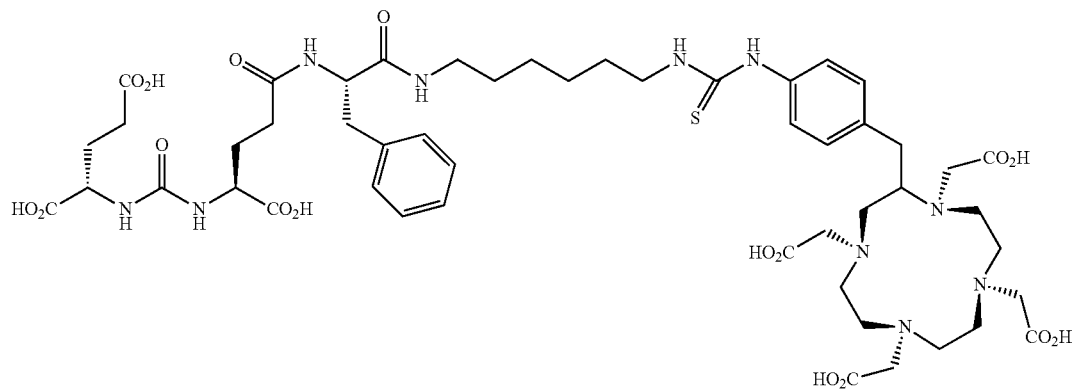
[MS (ESI)]: $(M+H)^+ = 1118$.

Example 23

Synthesis of (11S,16S,20S)-11-benzyl-10,13,18-trioxo-1-((4-(1,4,7,10-tetrakis(carboxymethyl)-1,4,7,10-tetraazacyclododecan-2-yl)methyl)phenyl)amino)-1-thioxo-2,9,12,17,19-pentaazadocosane-16,20,22-tricarboxylate Lu complex (Lu-MIP-1548)

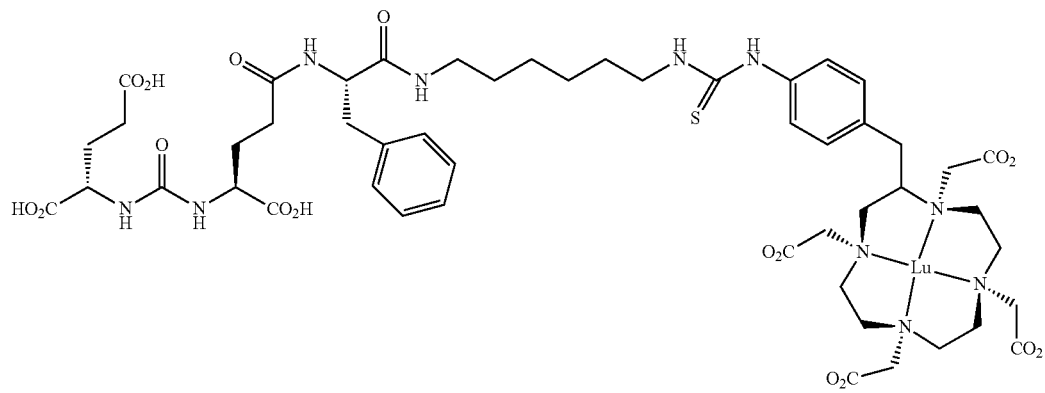

[MS (ESI)]: (M+H)$^+$=1289.

Synthetic protocols described above will be used to synthesize Formula I and Formula II compounds in which the chelator is a moiety selected from

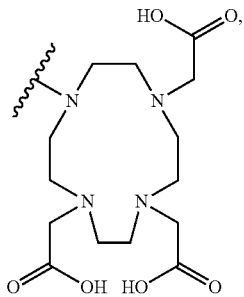

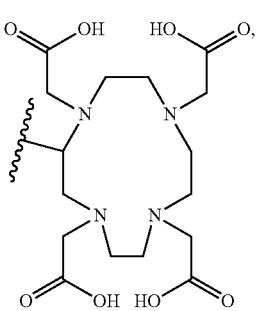

-continued

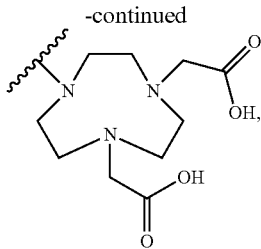

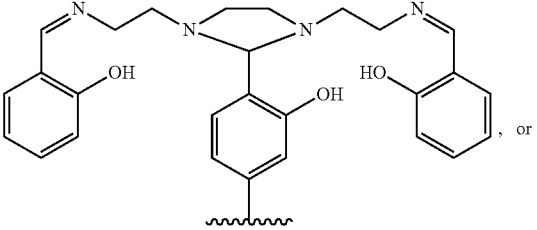

, or

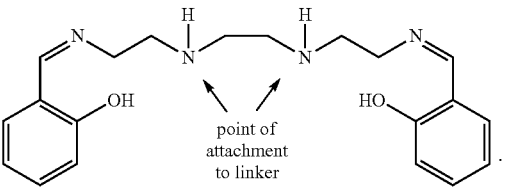

Formula I or Formula II compounds thus obtained may then be complexed with an appropriate radionuclide to give a radiopharmaceutical that is suitable for diagnostic imaging or for use as a therapeutic for treating cell proliferative diseases. Illustrative compounds having the above illustrated chelator groups include but are not limited to:

147              148
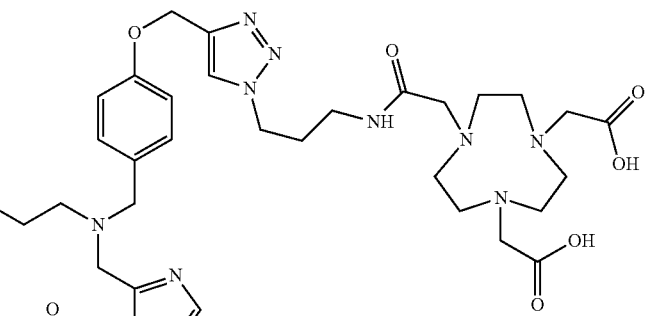
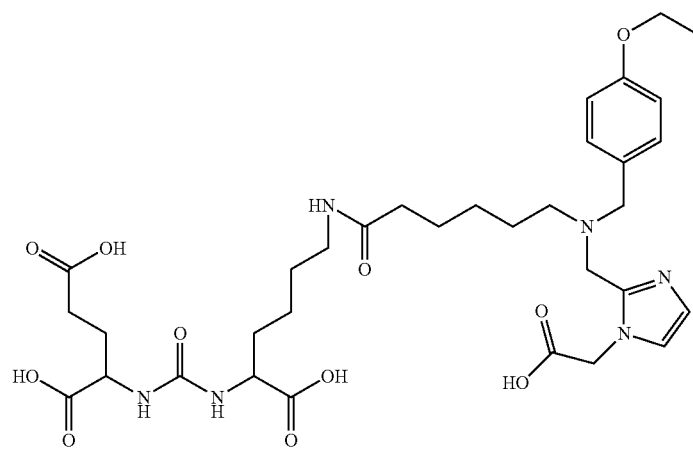
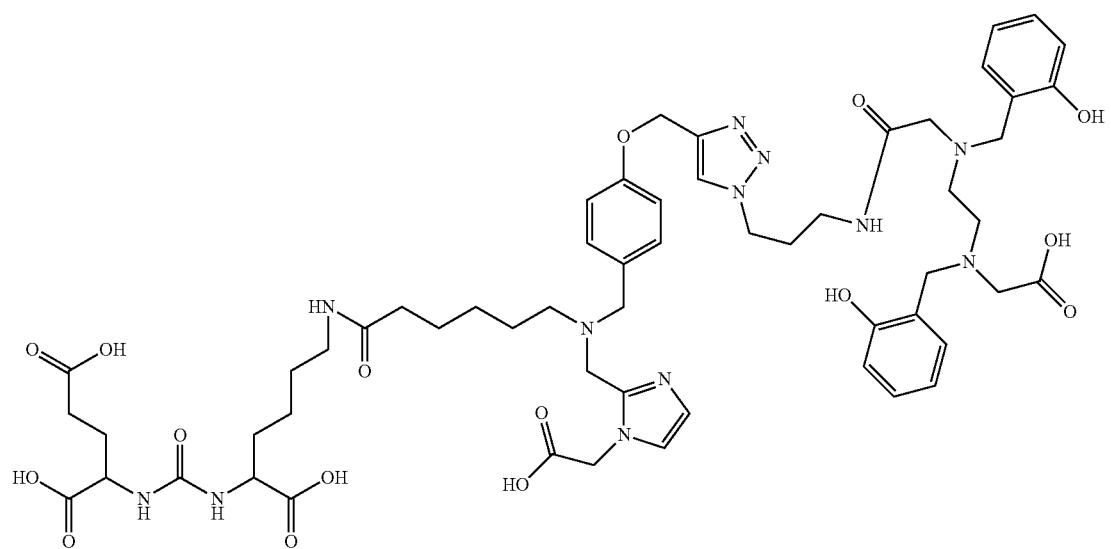
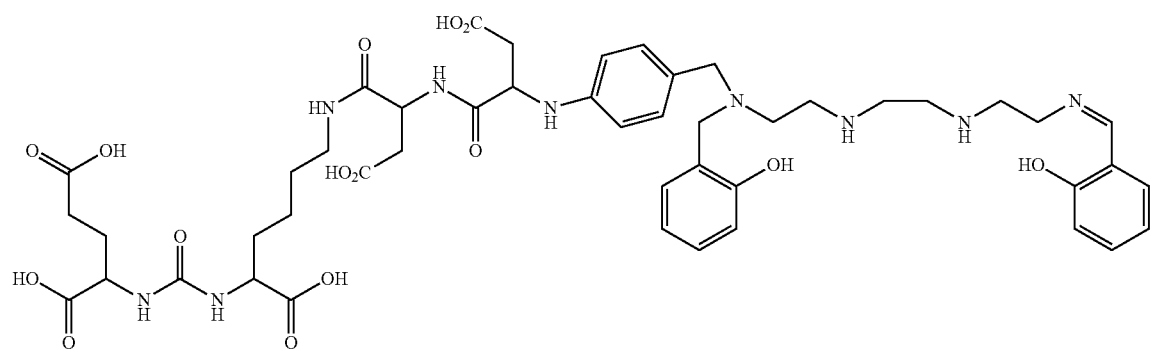

149 150
-continued
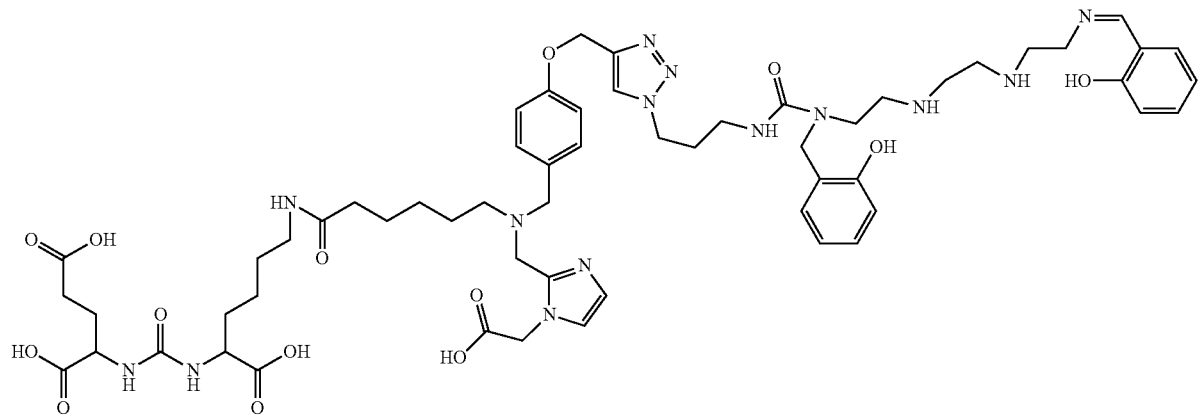
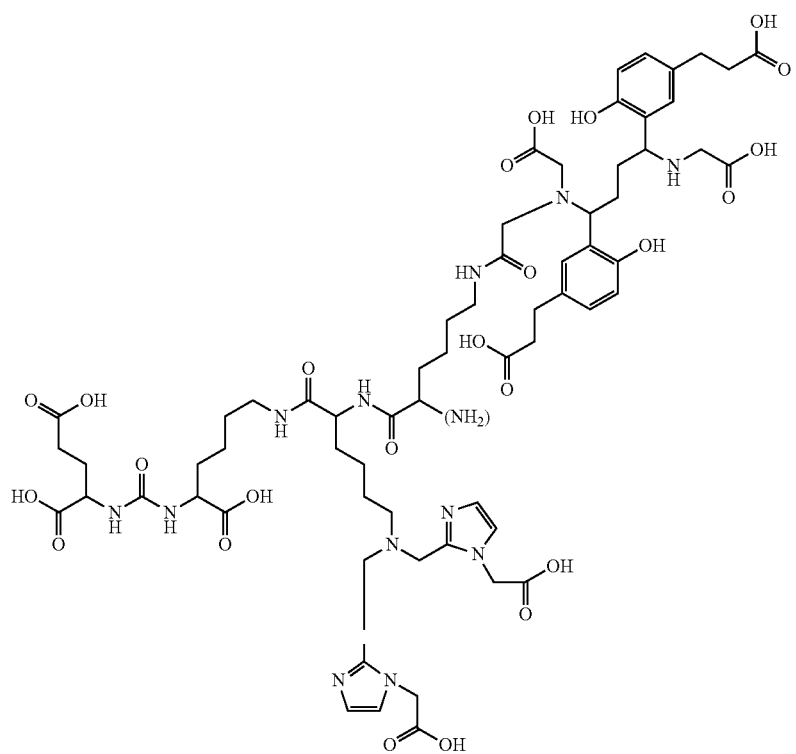
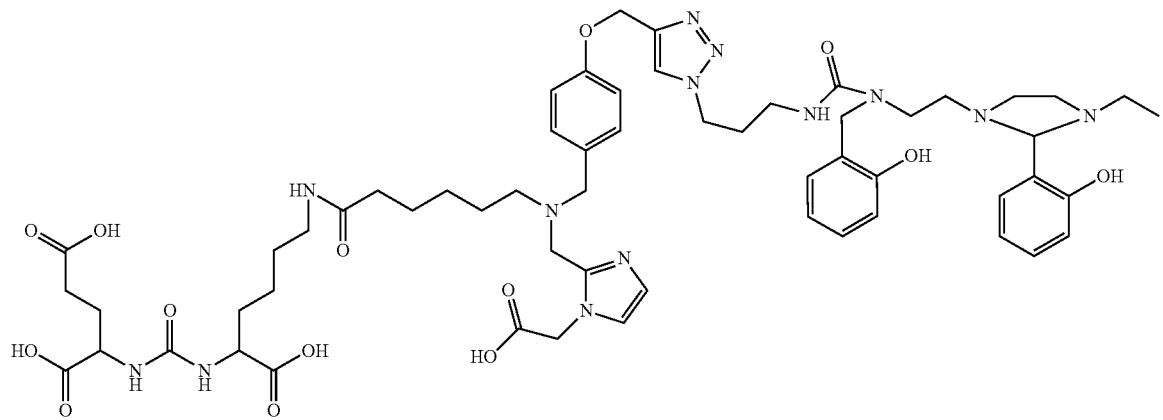

-continued

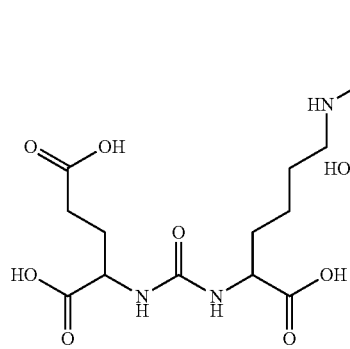
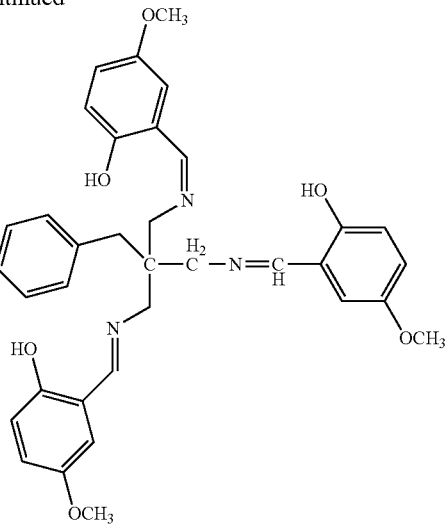

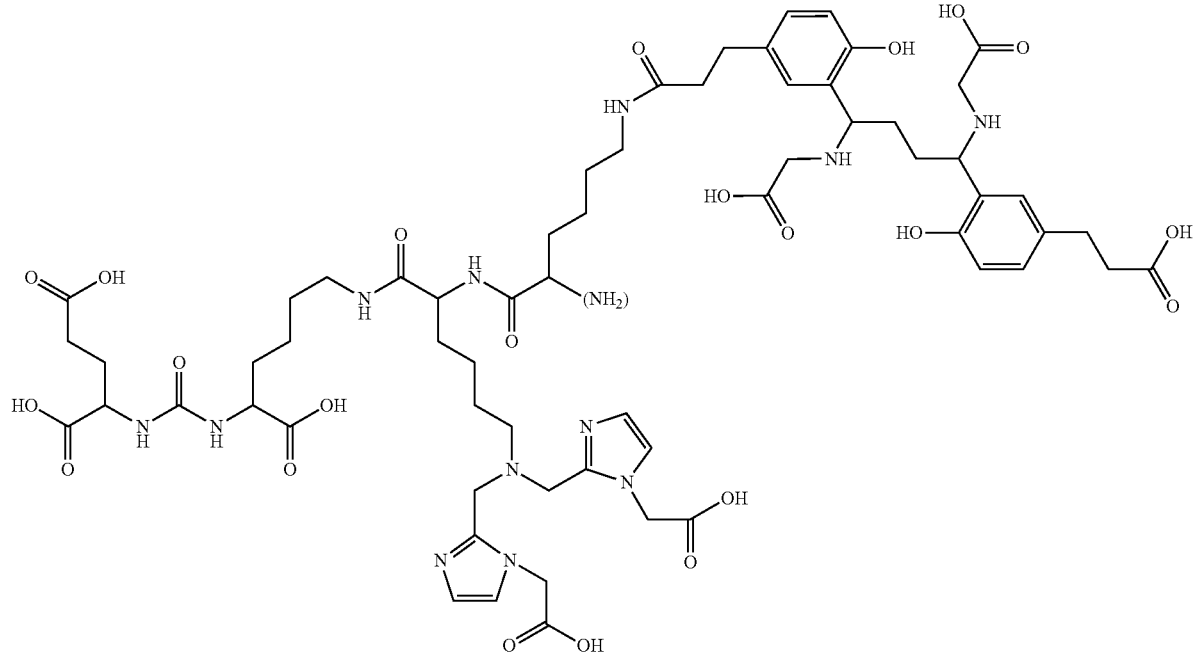

EQUIVALENTS

While certain embodiments have been illustrated and described, it should be understood that changes and modifications can be made therein in accordance with ordinary skill in the art without departing from the technology in its broader aspects as defined in the following claims.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member, including the first and last number listed for the range.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims.

What is claimed is:

1. A compound represented by formula I

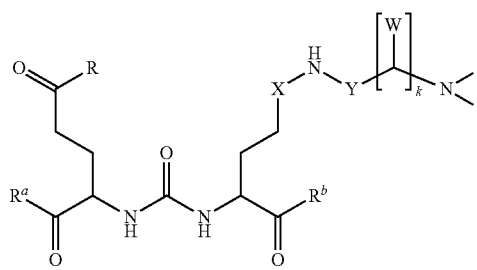

I wherein:
X and Y are each independently $(CHR^1)_m$ or $C(O)$;
W is H or $-(CH_2)_p-U$;
L is $-C(O)-(C_1-C_{10})$alkylene, $-[C(O)-(CH(Z)_d)-NH]_jNR^2R^3$, $-C(O)-(CHR^1)-(CH_2)_p-U-$, $-(C_5-C_{14})$aryl-$(C_1-C_{10})$alkylene, $R^6O$-benzylene, $-(C_5-C_{14})$heteroaryl-$(C_1-C_{10})$alkylene, $-C(O)-[(CH_2)_p-V]_n-(CH_2)_q-C(O)-U$ or $[C(O)-CH(Z)_d-NH]_t-C(O)-(CHR^1)_m-(CH_2)_p-U$;
T is selected from the group consisting of: H, $-(C_1-C_{10})$alkylene, $RC(O)-(C_1-C_{10})$alkylene, $NR^2R^3-(C_1-C_{10})$alkylene, $-(C_5-C_{14})$heteroaryl-$(C_1-C_{10})$alkylene and $-(C_5-C_{14})$aryl-$(C_1-C_{10})$alkylene;
U is selected from the group consisting of: $-OR$, $-COR$ and $-NR^4R^5$;
V is selected from the group consisting of $U-NH-$, $-NR^2-$ and $-NR^2R^3$;
Z is $-(CH_2)_p-COOH$ or $-(CH_2)_p-NR^2R^3$;
R, $R^a$ and $R^b$ are each independently $-H$, $-OH$, $-(C_1-C_{10})$alkyl, $-O(C_1-C_{10})$alkyl, or $NHR^2$;
$R^1$ and $R'''$ are each independently $-H$ or $-NH_2$;
$R^2$, $R^3$, $R^4$ and $R^5$ are each independently H, bond, $(C_1-C_{10})$alkylene, F, Cl, Br, I, $C(O)$, $C(S)$, $-C(S)-NH$-benzyl-, $-C(O)-NH$-benzyl-, $-C(O)-(C_1-C_{10})$alkylene, $-(CH_2)_p-NH-C(O)-(CH_2)_p-$, $-(CH_2-CH_2)_t-NH-C(O)-(CH_2)_p-$, $-(CH_2)_p-COR$, $-(CH_2)_p-C(O)NH-C[(CH_2)_p-COR]_3$, $-C[(CH_2)_p-COR]_3$, or $-(CH_2)_p-(C_5-C_{14})$heteroaryl;
$R^6$ is $-O(CH_2)_p-(C_5-C_{14})$heteroaryl-$(CH_2)_p-U$;

D is

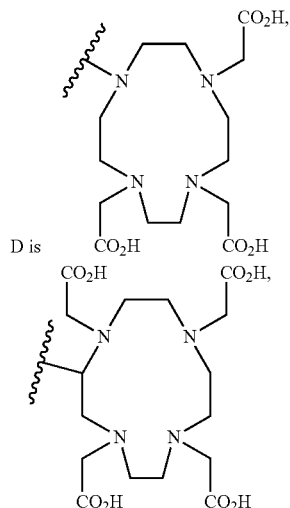

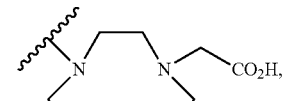

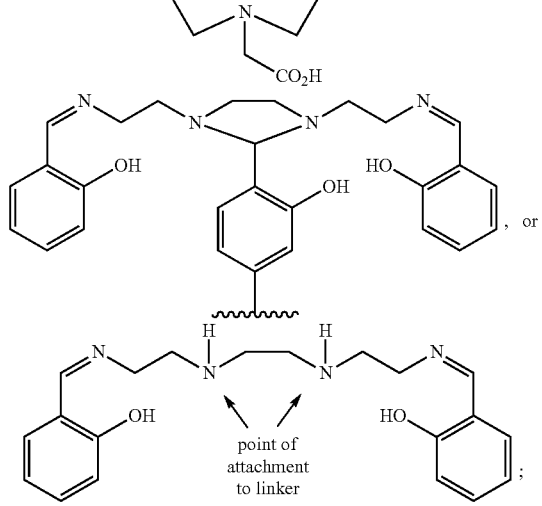

d, j, k, m, n, p and t are each independently 0, 1, 2, 3, 4, 5, or 6; and
with the proviso that where W is $-(CH_2)_5-$ or $-CH(NH_2)-(CH_2)_4-$, L is not a $-C(O)CH_2-$.

2. The compound of claim 1, wherein X is $(CHR^1)_m$, Y is $C(O)$, W is hydrogen and k is 5.

3. The compound of claim 1, wherein L is $-C(O)CH_2-$ and T is hydrogen.

4. The compound of claim 1, wherein $R^1$ is hydrogen and m is 2.

5. The compound of claim 1, wherein L is $-C(O)-[(CH_2)_p-V]_n-(CH_2)_q-C(O)-U$ or $-C(O)-(C_1-C_{10})$alkylene.

6. The compound of claim 5, wherein L is $-C(O)$methylene.

7. The compound of claim 5, wherein L is $-C(O)-[(CH_2)_p-V]_n-(CH_2)_q-C(O)-U$ and T is hydrogen.

8. The compound of claim 7, wherein V is $NR^2$, n is 2 and q is 1.

9. The compound of claim 7, wherein U is $NR^2R^3$.

10. The compound of claim 9, wherein $R^2$ is hydrogen and $R^3$ is —$(CH_2)_2$—NH—C(O)—$(CH_2)$—.

11. The compound of claim 1, wherein L is $OR^6$-benzylene and T is —$(C_5$-$C_{14})$heteroaryl-$(C_1$-$C_{10})$alkylene.

12. The compound of claim 11, wherein the heteroaryl is an imidazole, further substituted with the group —$(C_1$-$C_{10})$alkylene-C(O)—U.

13. The compound of claim 11, wherein T is selected from the group consisting of

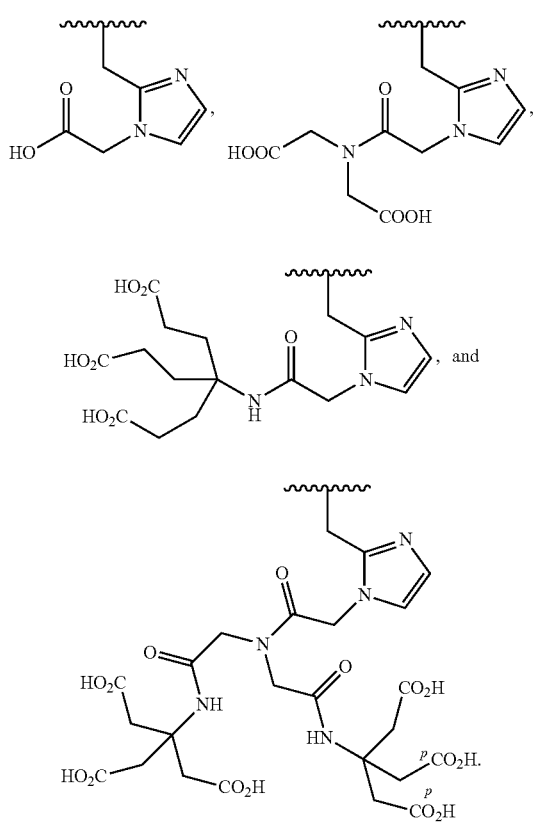

14. The compound of claim 1, wherein T is.

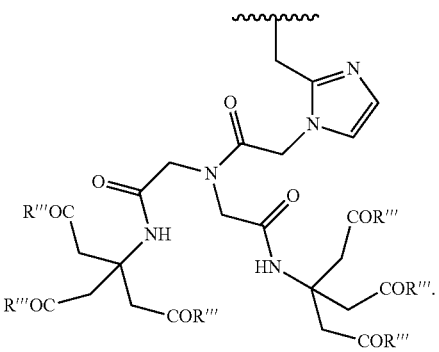

15. The compound of claim 14, wherein each R''' is independently

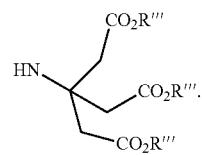

16. The compound of claim 4, wherein W is —$(CH_2)$—COOH, k is 1, L is —$[C(O)$—$(CH(Z)_d)$—$NH]_j$—$NR^2R^3$ and T is hydrogen.

17. The compound of claim 16, wherein $R^2$ is hydrogen, $R^3$ is —$C(O)CH_2$— and j is 4.

18. The compound of claim 4, wherein W and T are hydrogen, k is 5, and L is $[C(O)$—$CH(Z)_d$—$NH]_t$—$C(O)$—$(CHR^1)_m$—$(CH_2)_p$—U.

19. The compound of claim 18, wherein Z is —$(CH_2)_4$—$NR^2R^3$ and U is —$NR^4R^5$.

20. The compound of claim 18, wherein m and t are 1, p is 4 and $R^1$ is —$NH_2$.

21. The compound of claim 19, wherein $R^4$ is hydrogen and $R^5$ is C(O)methylene.

22. The compound of claim 19, wherein $R^2$ and $R^3$ are each independently —$(CH_2)_p$—$(C_5$-$C_{14})$heteroaryl.

23. The compound of claim 18, wherein p is 1 and the heteroaryl is an imidazole, further substituted with the group —$(C_1$-$C_{10})$alkylene-C(O)—U.

24. The compound of claim 1, which is:

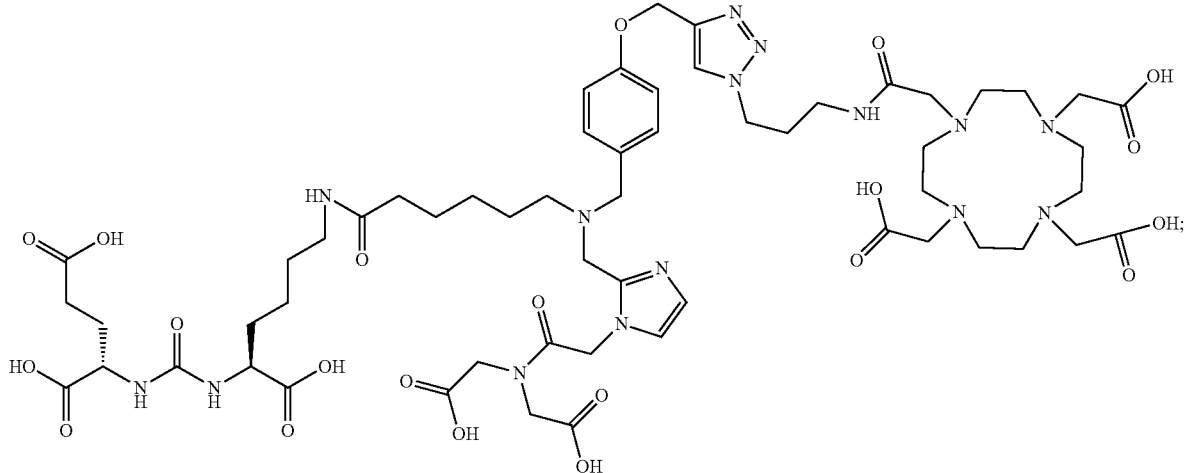

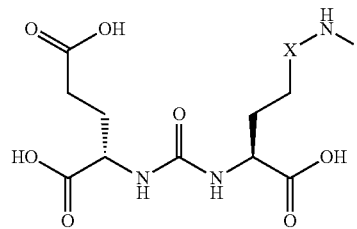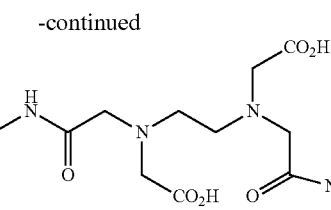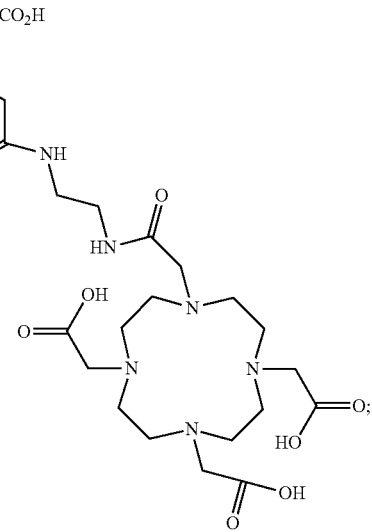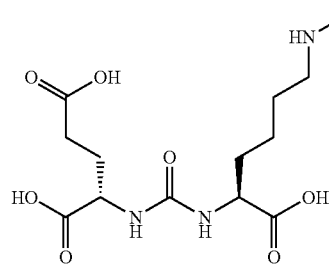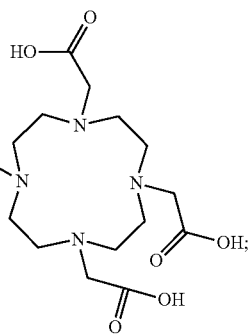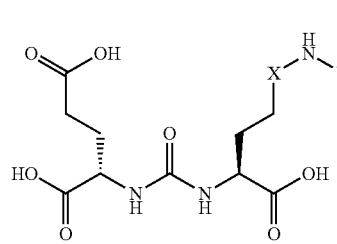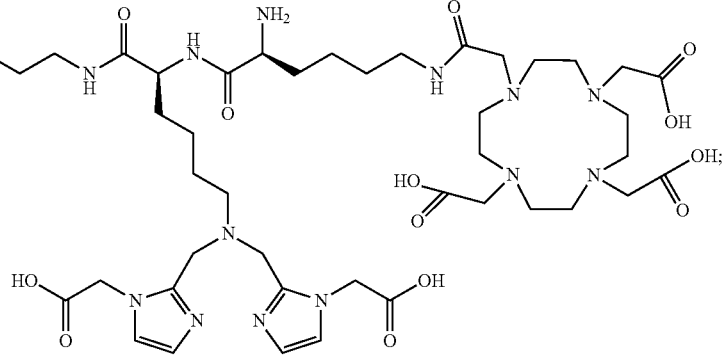

159
-continued
160
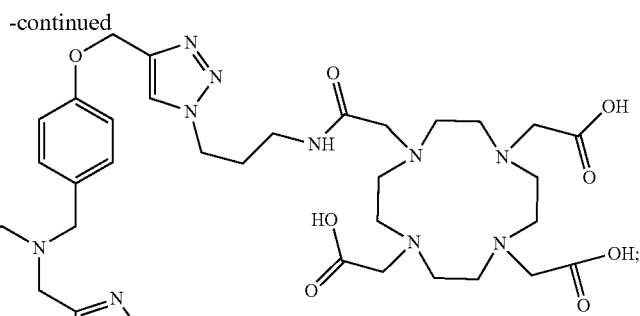
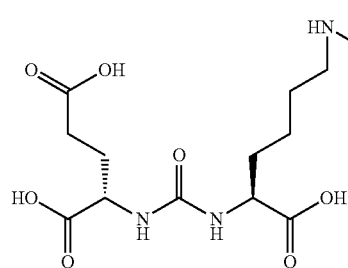 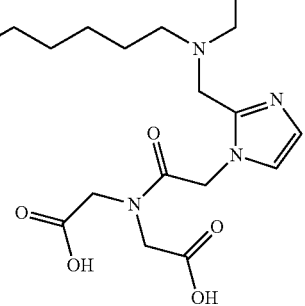
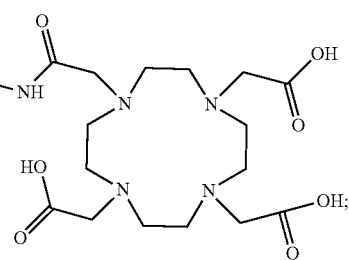
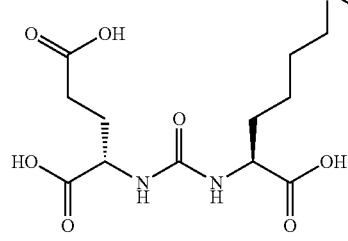 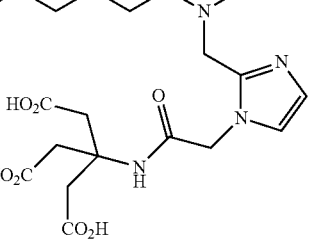
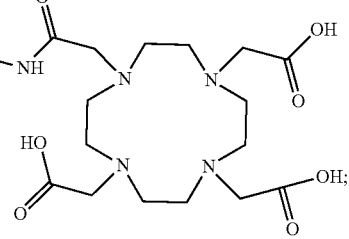
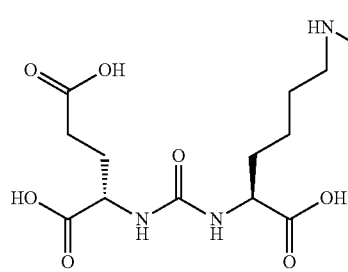 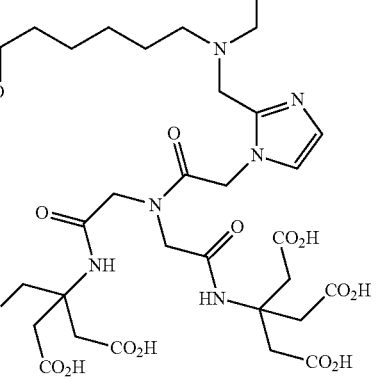

161
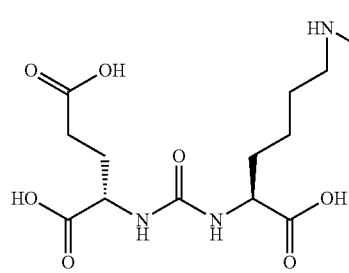
162
-continued
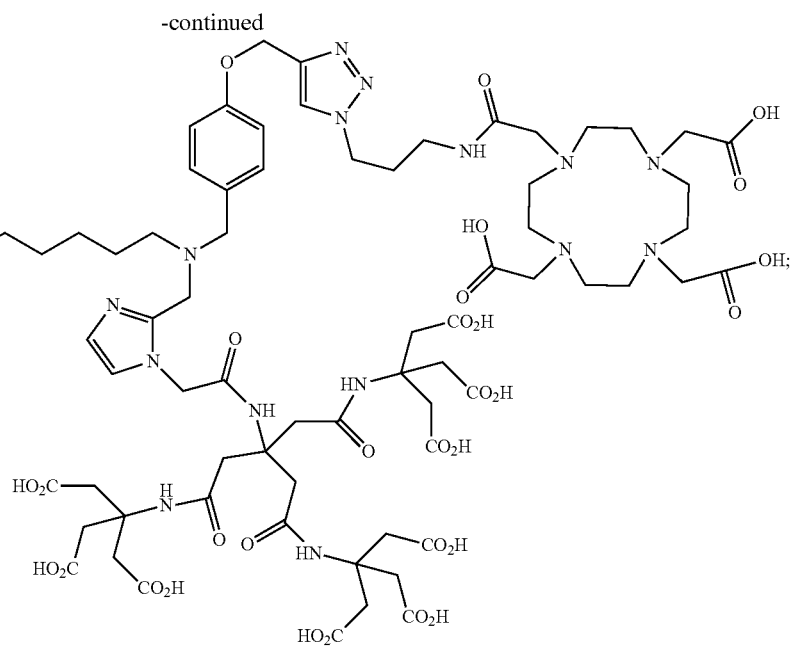
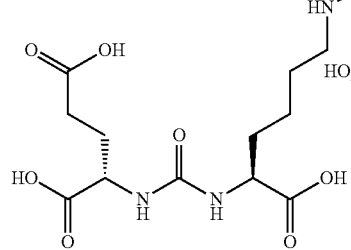
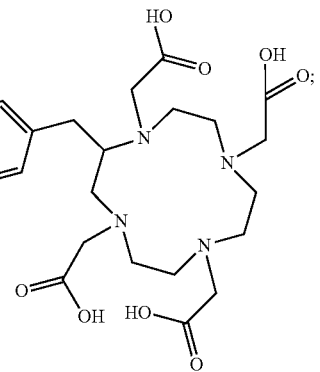
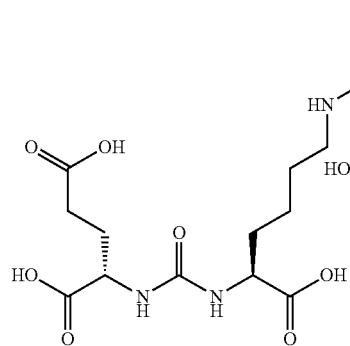
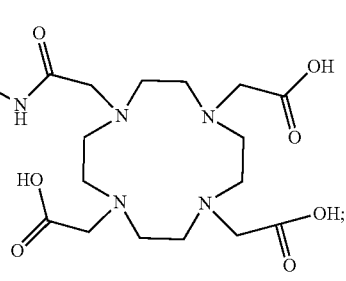

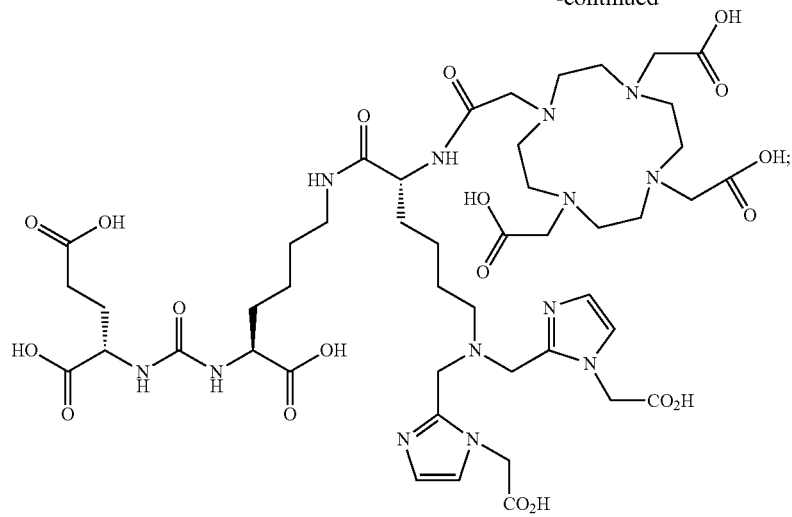
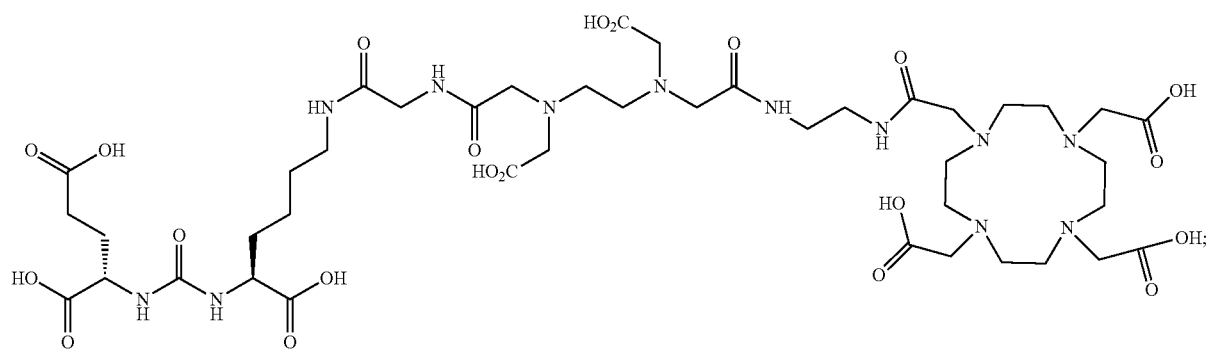
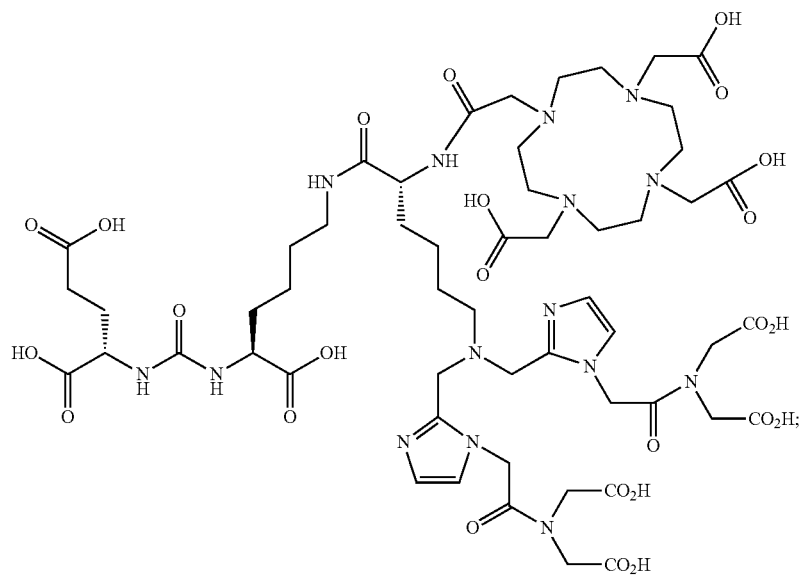

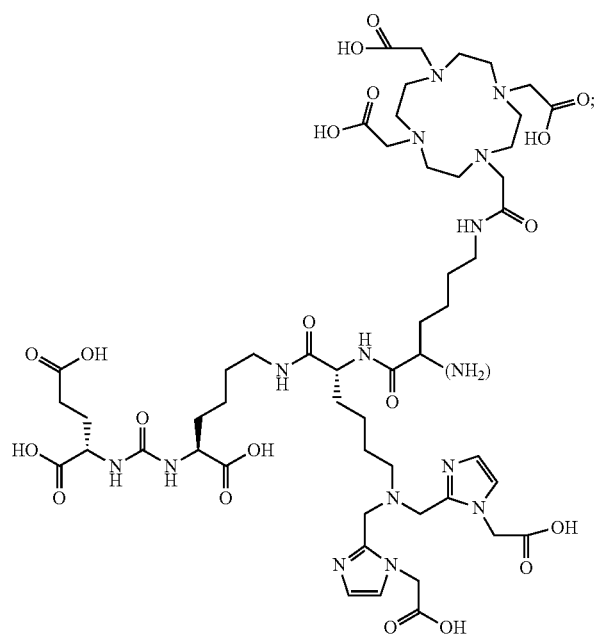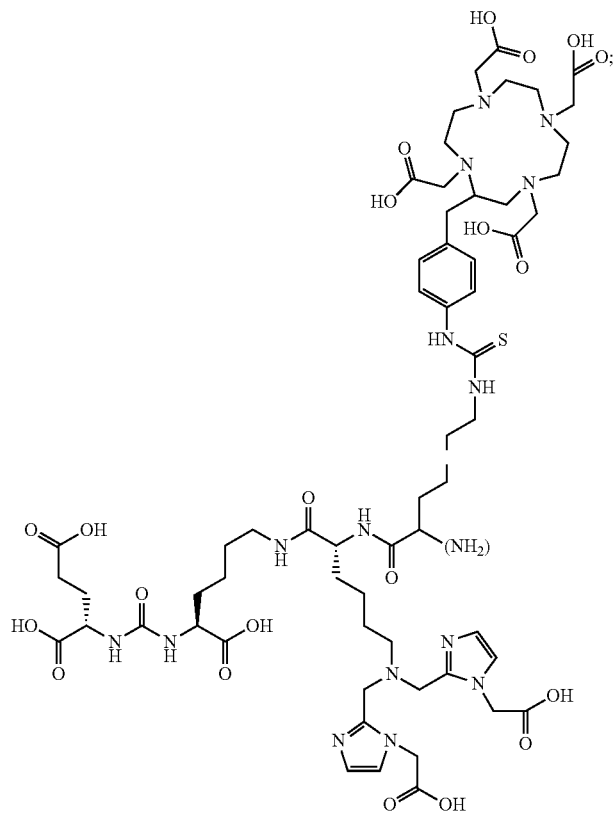

-continued
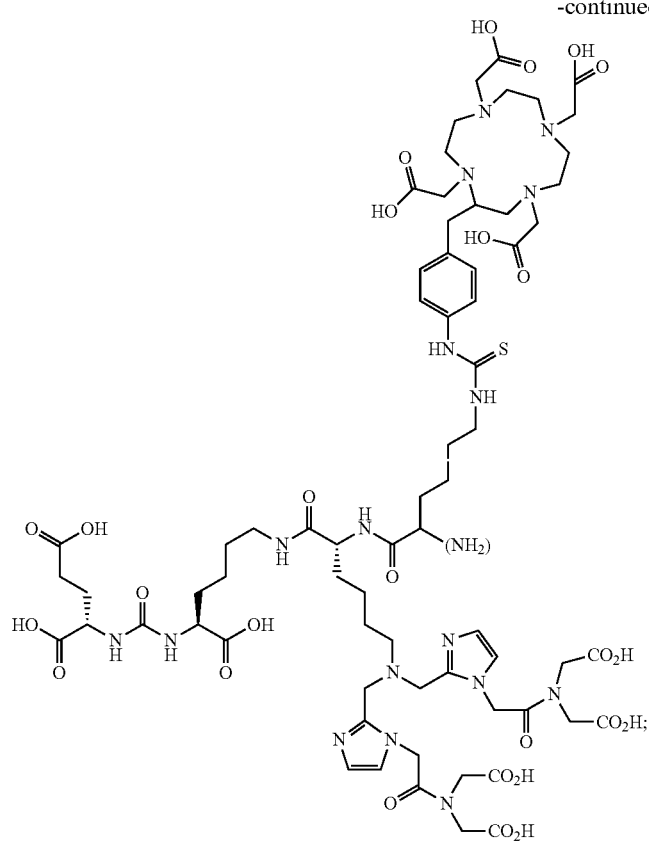
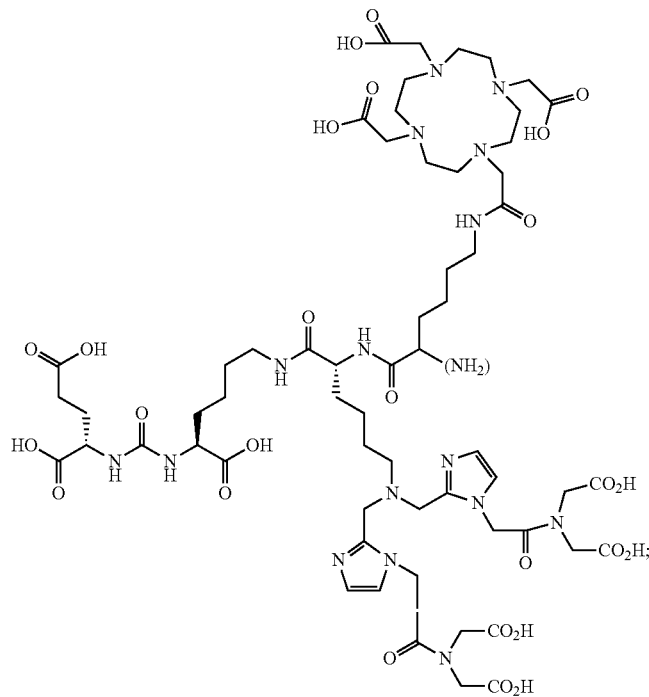
or a pharmaceutically acceptable salt, or ester thereof.
25. A metal complex comprising a radionuclide and the compound of claim 1.
26. The metal complex of claim 25, wherein the radionuclide is selected from the group consisting of $^{111}$In, $^{90}$Y, $^{68}$Ga, $^{64}$Cu $^{153}$Gd, $^{155}$Gd, $^{157}$Gd, $^{157}$Fe and $^{177}$Lu.

27. The metal complex of claim 25, which is:
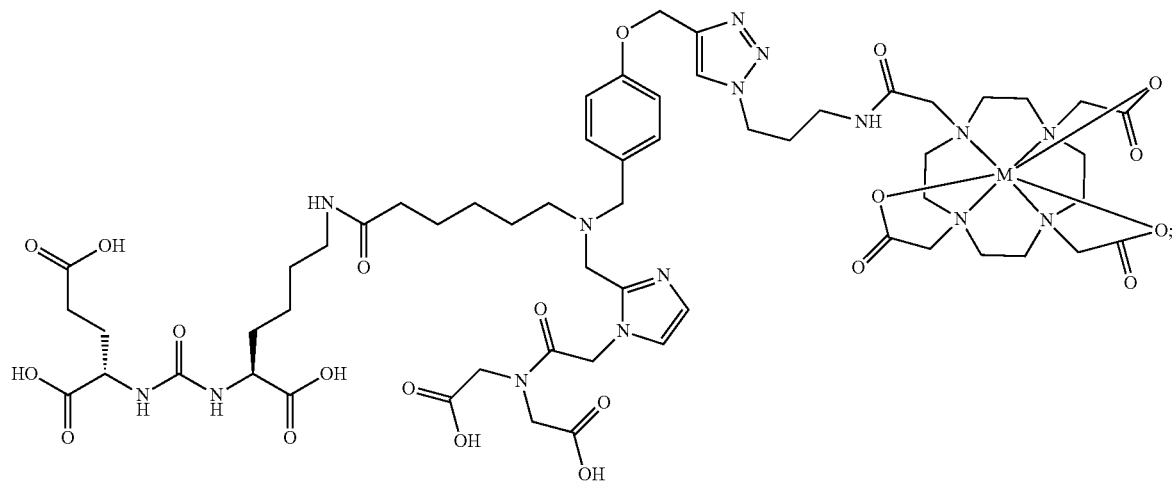
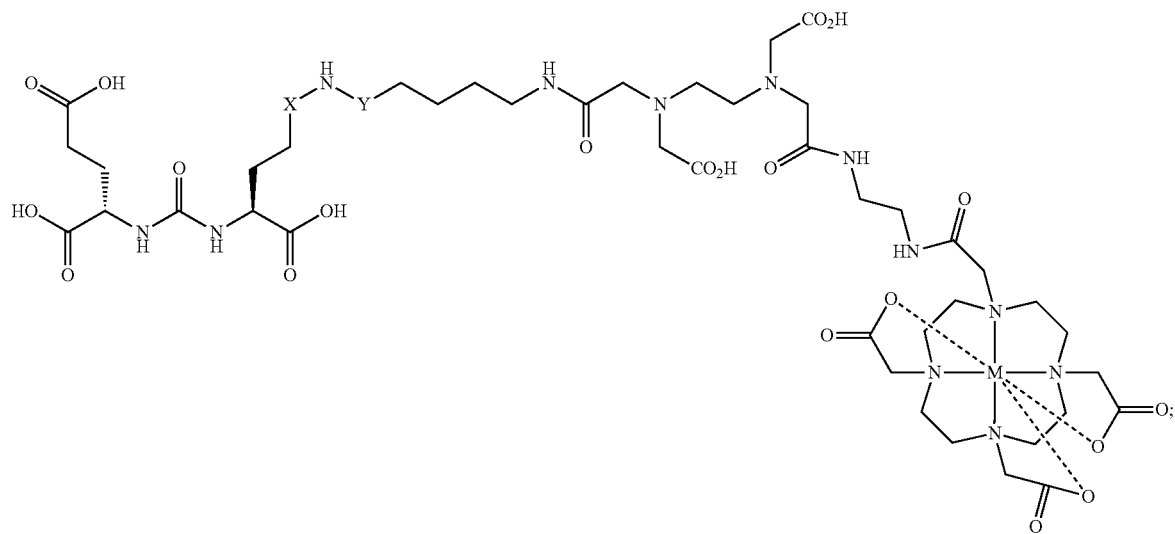
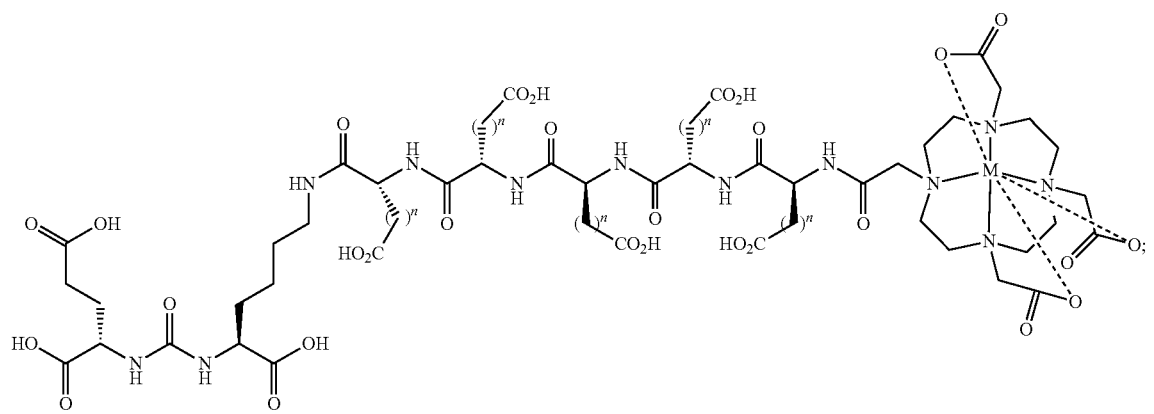

171
-continued
172
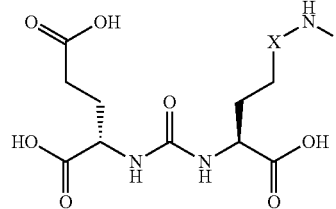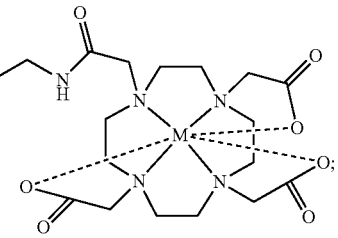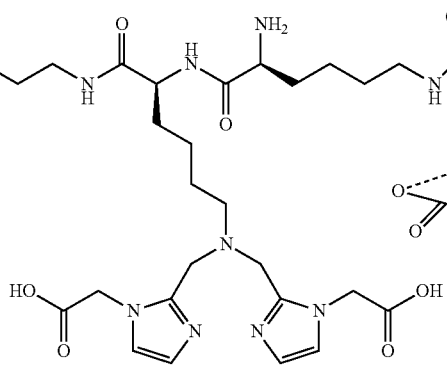
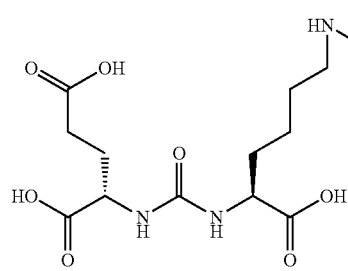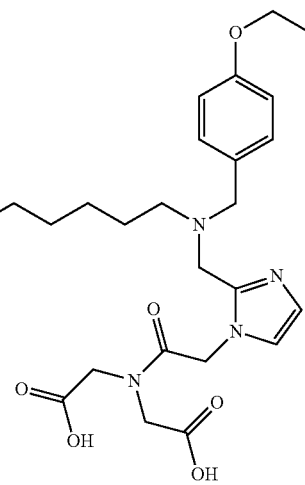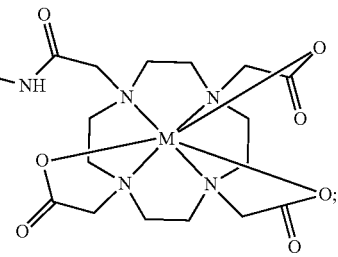
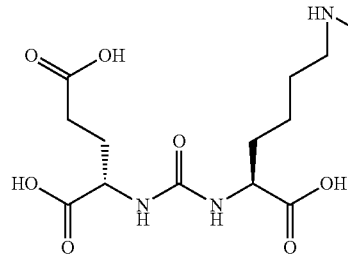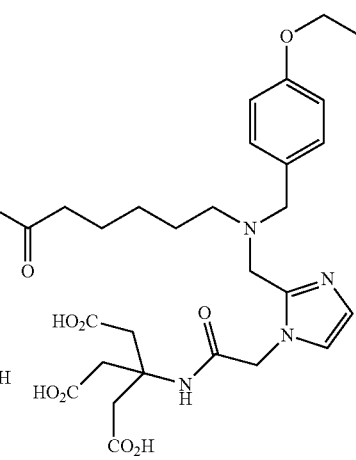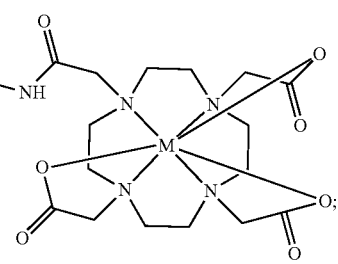

-continued
173
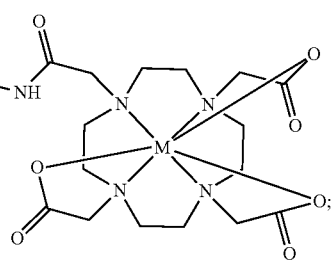
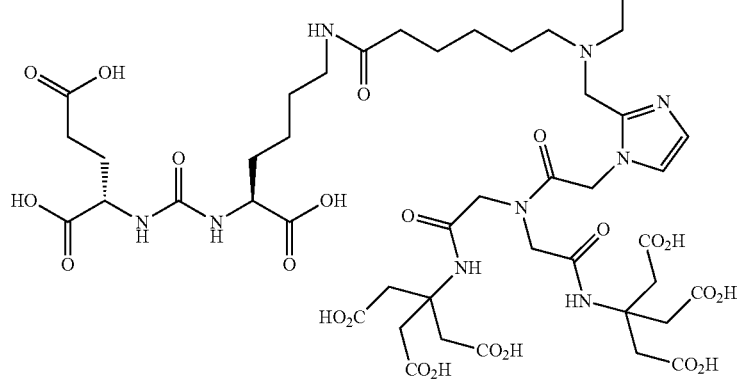
174
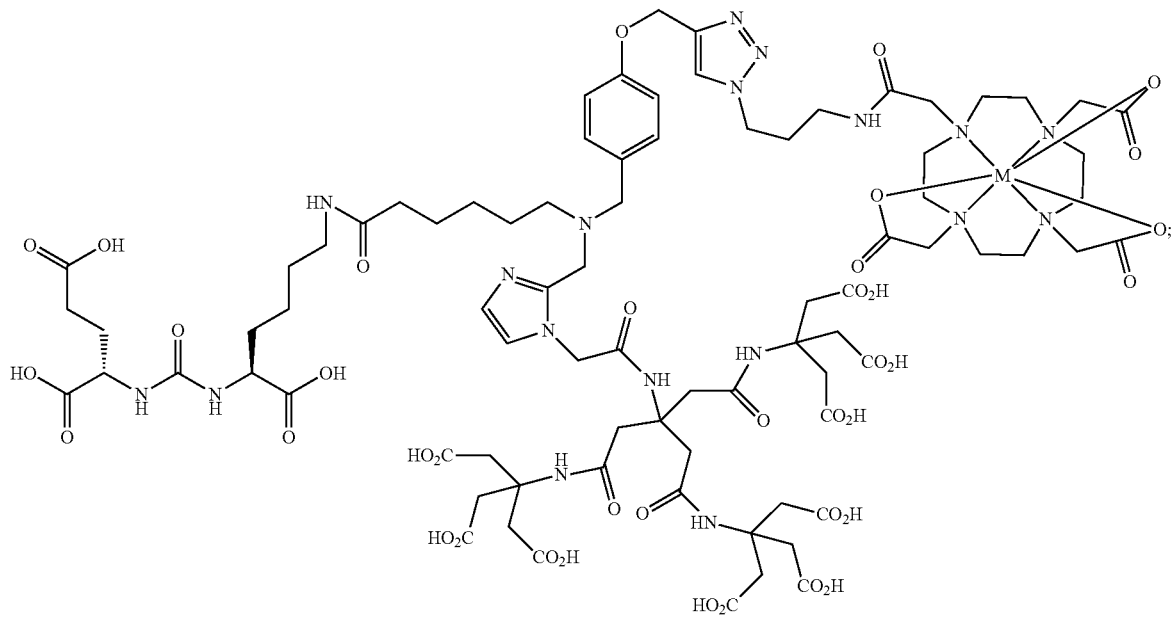
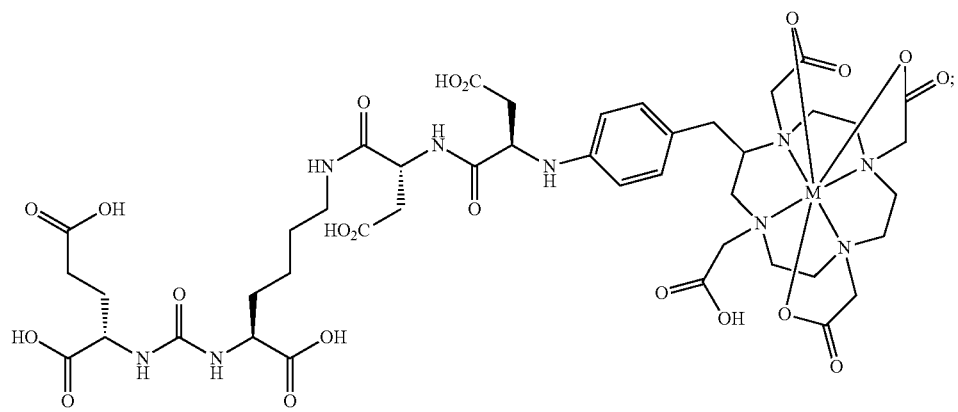

175
176
-continued
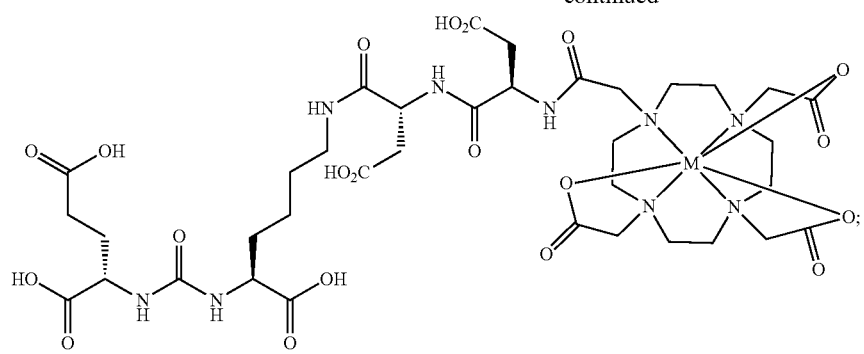
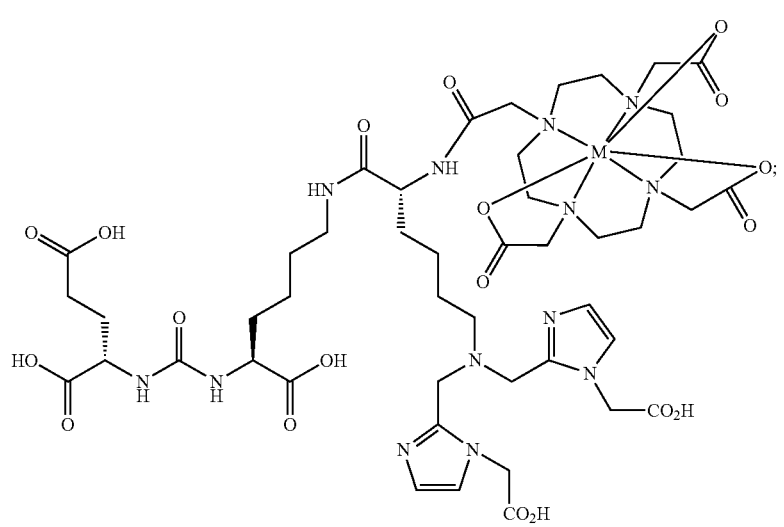
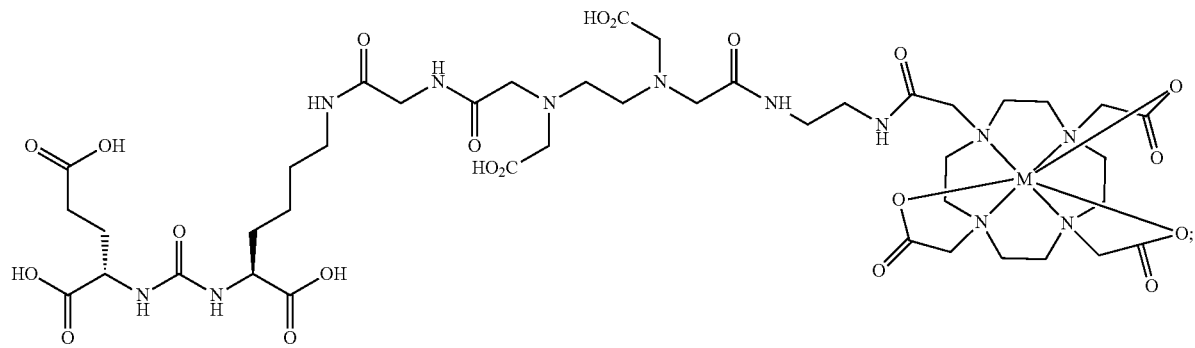

-continued
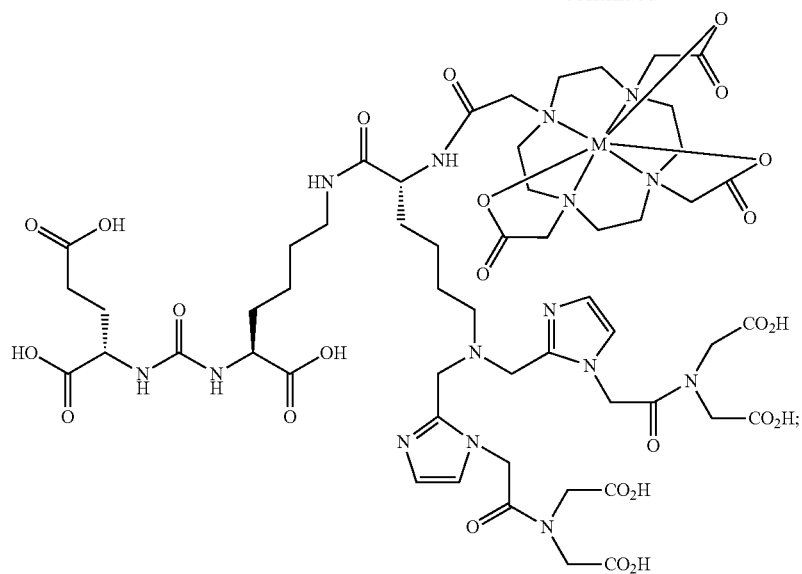
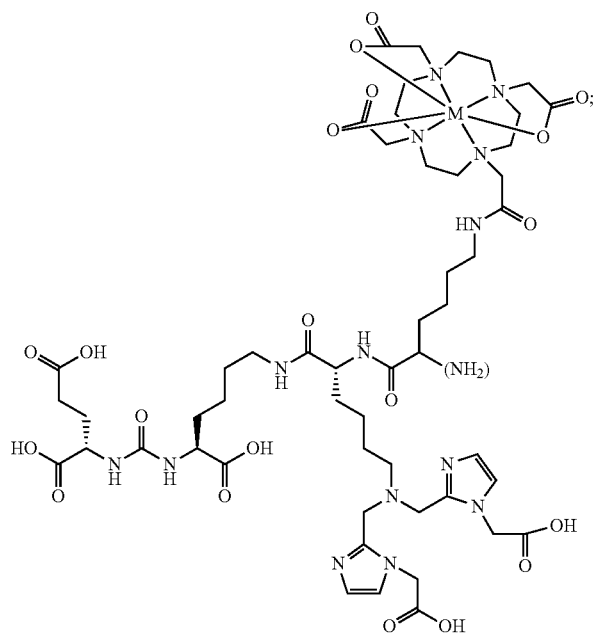

-continued
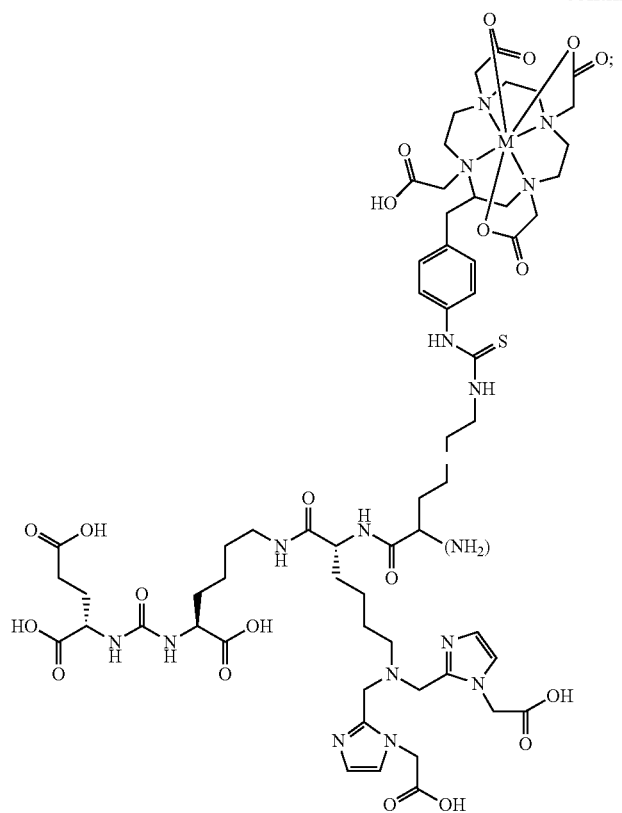
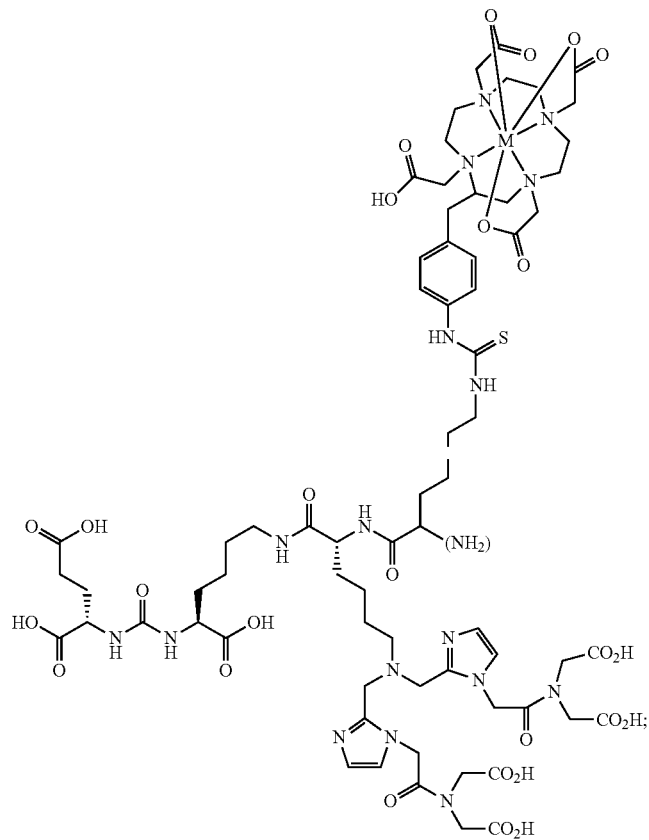

-continued

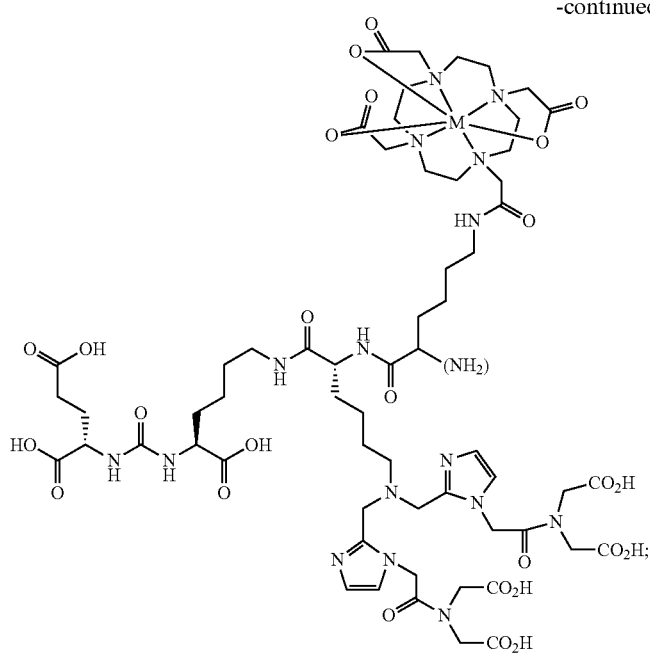

or a pharmaceutically acceptable salt thereof;
wherein M is $^{111}$In, $^{90}$Y, $^{68}$Ga, $^{64}$Cu, or $^{177}$Lu.

28. A pharmaceutical composition comprising the compound of claim 1, or a pharmaceutically acceptable salt or ester thereof; and a pharmaceutically acceptable carrier.

29. A pharmaceutical composition comprising the metal complex of claim 25, or a pharmaceutically acceptable salt or ester thereof; and a pharmaceutically acceptable carrier.

* * * * *